(12) United States Patent
Kita et al.

(10) Patent No.: US 7,751,988 B2
(45) Date of Patent: Jul. 6, 2010

(54) LEAD MOLECULE CROSS-REACTION PREDICTION AND OPTIMIZATION SYSTEM

(75) Inventors: David Kita, Milpitas, CA (US); Eniko Fodor, Fremont, CA (US); Adityo Prakash, Fremont, CA (US)

(73) Assignee: Verseon, Milpitas, CA (US)

( * ) Notice: Subject to any disclaimer, the term of this patent is extended or adjusted under 35 U.S.C. 154(b) by 591 days.

(21) Appl. No.: 10/966,341

(22) Filed: Oct. 14, 2004

(65) Prior Publication Data

US 2005/0170379 A1 Aug. 4, 2005

Related U.S. Application Data

(60) Provisional application No. 60/511,474, filed on Oct. 14, 2003.

(51) Int. Cl.
G06F 19/00 (2006.01)
G11C 17/00 (2006.01)
(52) U.S. Cl. .......................................... 702/27; 365/94
(58) Field of Classification Search ....................... None
See application file for complete search history.

(56) References Cited

U.S. PATENT DOCUMENTS

| 6,427,141 | B1 * | 7/2002 | Barnhill ...................... 706/16 |
| 6,519,611 | B1 | 2/2003 | Zong |
| 2003/0125315 | A1 * | 7/2003 | Mjalli et al. ........... 514/210.01 |
| 2003/0131015 | A1 | 7/2003 | Chen |

OTHER PUBLICATIONS

Sheridan et al. Why do we need so many chemical similarity search methods? Drug Discovery Today. vol. 7, pp. 903-910 (2002).*
Rockey et al. Progress Toward Virtual Screening for Drug Side Effects. Proteins. vol. 48, pp. 664-671 (2002).*
LeTrong et al. 1.3 angstrom Resolution Structure of Human Glutathione S-Transferase with S-Hexyl Glutathione Bound Reveals Possible Extended Ligandin Binding Site. Proteins. vol. 48, pp. 618-627 (2002).*
Kitchen et al. Docking and Scoring in Virtual Screening for Drug Discovery: Methods and Applications Nature Reviews Drug Discovery vol. 3 pp. 935-949 (2004).*
Bingham, Jonathan et al.; "Visualizing large hierarchical clusters in hyperbolic space"; 2000, Bioinformatics, vol. 16, No. 7, pp. 660-661.
Chen, Yu Zong et al. "Computational Method for Drug Target Search and Application in Drug Discovery." *Journal of Theoretical and Computational Chemistry*, vol. 1, No. 1, pp. 213-224. 2002. Printed from http://www.worldscinet.com/jtcc/01/sample/S0219633602000166.pdf on Sep. 26, 2003.
Chen, Yu Zong et al. "Computer Automated Prediction of Potential Therapeutic and Toxicity Protein Targets of Bioactive Compounds from Chinese Medicinal Plants." *Am. J. of Chin. Med.*, vol. 30, No. 1, pp. 139-154. 2002.
Chen, Yu Zong et al. "Prediction of Potential Toxicity and Side Effect Protein Targets of a Small Molecule by a Ligand-Protein Inverse Docking Approach." *J. Mol. Graph. Model.*, vol. 20, No. 3, pp. 199-218. 2001.
Chen, Yu Zong et al. "Ligand-Protein Inverse Docking and Its Potential Use in the Computer Search of Protein Targets of a Small Molecule." *Proteins*, vol. 43, No. 2, pp. 217-226. May 1, 2001.
Chen, X. et al. "TTD: Therapeutic Target Database." *Nucleic Acids Res.*, vol. 30, No. 1, pp. 412-415. Jan. 1, 2002. Printed from http://nar.oupjournals.org/cgi/content/full/30/1/412.
Elder, Benjamin. "Molecular Docking and Its Applications to Treating Type 2 Diabetes." Printed from http://bioinfo.mbb.yale.edu/mbb452a/2002/projects-2002/elder.pdf on Sep. 26, 2003.
Liu, M. et al. "MCDOCK: a Monte Carlo Simulation Approach to the Molecular Docking Problem." *J. Comput. Aided Mol Des.*, vol. 13, No. 5, pp. 435-451. Sep. 1999.
Jones, G. et al. "Development and Validation of a Genetic Algorithm for Flexible Docking." *J. Mol. Biol.*, vol. 267, No. 3, pp. 727-748. Apr. 4, 1997.
Supplementary European Search Report dated Dec. 28, 2009 from European Patent Application No. 04795308.8, 5 pages.
Carlin, R.J. et al.; "Characterization of monoclonal anti-furosemide antibodies and molecular modeling studies of cross-reactive compounds"; 1994, *Molecular Immunology*, vol. 31, No. 2, pp. 153-164.
Bartlett, A. et al.; "Prediction of potential cross-reactivity between [beta]-lactam antibodies and anti-benzylpenicillin surum antibodies"; 1996, *Pharmaceutical Sciences*, vol. 2, No. 1, pp. 65-68.
Kauvar, L.M. et al.; "Predicting Ligand Binding to Proteins by Affinity Fingerprinting"; 1995, *Chemistry and Biology*, vol. 2, No. 2, pp. 107-118.
Podesta, A. et al.; "Specificity in protein-ligand interactions: a model from estrone-antiserum binding"; 1994, *Biochimica et Biophysica Acta*, vol. 1200, No. 3, pp. 291-206.
Ramsland, Paul A. et al.; "Immunoglobulin cross-reactivity examined by library screening, crystallography and docking studies"; 2001, *Combinatorial Chemistry and High Throughput Screening*, vol. 4, No. 5, pp. 397-408.
Soma, L.R. et al.; "Predicting Cross-Reactivity of Drug Monoclonal Antibodies Using Molecular Modeling"; 1991, *FASEB Journal*, vol. 5, No. 4, pp. A463.

* cited by examiner

*Primary Examiner*—John S Brusca
(74) *Attorney, Agent, or Firm*—Townsend and Townsend and Crew LLP

(57) ABSTRACT

A method for the prediction of adverse cross-reactions between lead candidate biomolecules and potential reactant molecules, often biopolymers, is described. In a computational system, reactions are modeled within a suitable environment, in order to determine a reaction profile between a lead candidate molecule and a potential reactant molecule. A risk assessment is then generated for each lead based on a plurality of reaction profiles for the lead with respect to a plurality of potential reactant molecules. The method includes provisions for redesign and optimization of the lead candidate, possibly iterative in nature, in order to avoid predicted adverse cross-reactions.

75 Claims, 25 Drawing Sheets

Figure 10B:
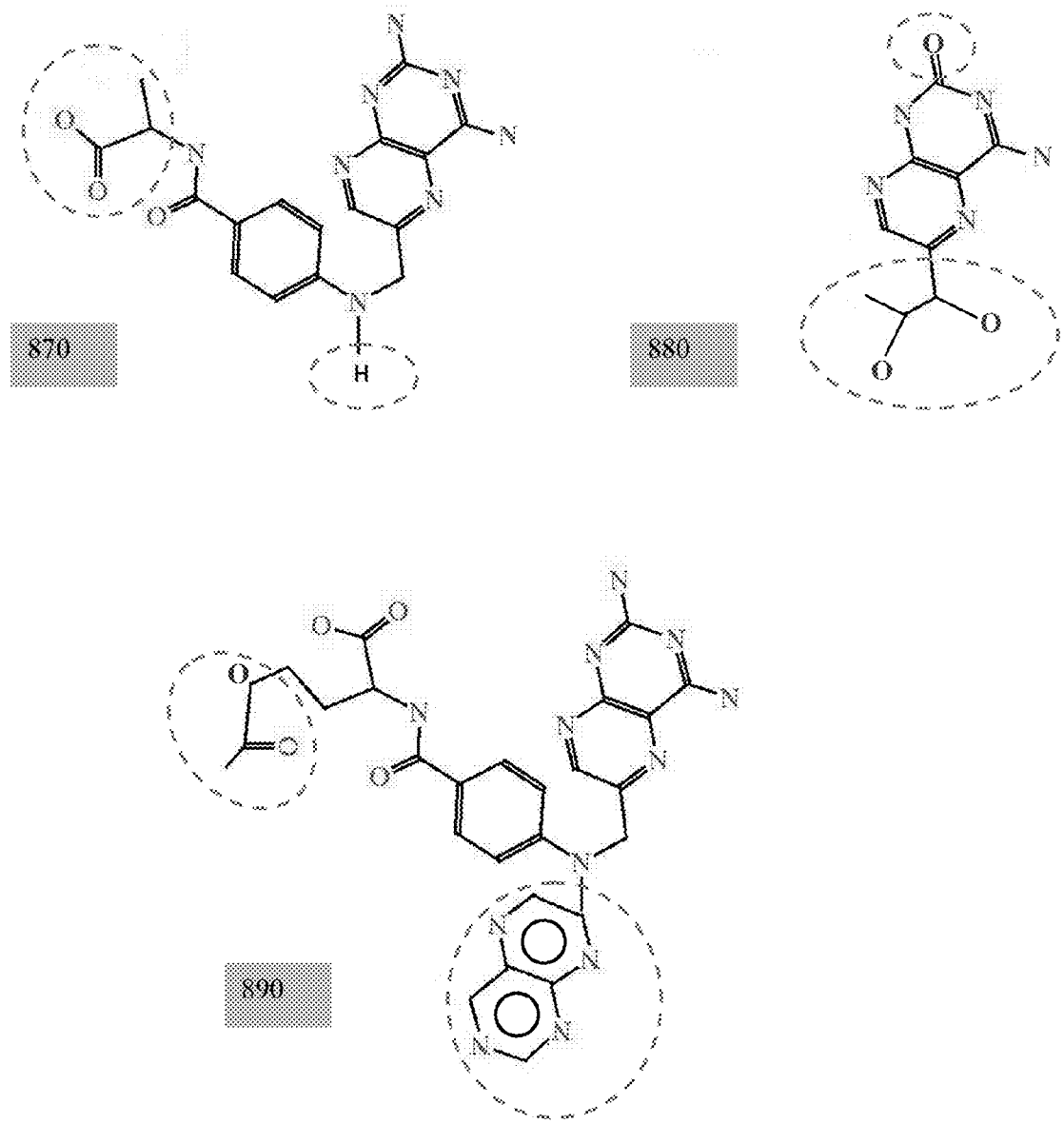

MET ILE SER LEU ILE ALA ALA LEU ALA VAL ASP ARG VAL
ILE GLY MET GLU ASN ALA MET PRO TRP ASN LEU PRO ALA
ASP LEU ALA TRP PHE LYS ARG ASN THR LEU ASP LYS PRO
VAL ILE MET GLY ARG HIS THR TRP GLU SER ILE GLY ARG
PRO LEU PRO GLY ARG LYS ASN ILE ILE LEU SER SER GLN
PRO GLY THR ASP ASP ARG VAL THR TRP VAL LYS SER VAL
ASP GLU ALA ILE ALA ALA CYS GLY ASP VAL PRO GLU ILE
MET VAL ILE GLY GLY GLY ARG VAL TYR GLU GLN PHE LEU
PRO LYS ALA GLN LYS LEU TYR LEU THR HIS ILE ASP ALA
GLU VAL GLU GLY ASP THR HIS PHE PRO ASP TYR GLU PRO
ASP ASP TRP GLU SER VAL PHE SER GLU PHE HIS ASP ALA
ASP ALA GLN ASN SER HIS SER TYR CYS PHE LYS ILE LEU
GLU ARG ARG

110

Fig 1A: Amino acid sequence for dihydrofolate reductase

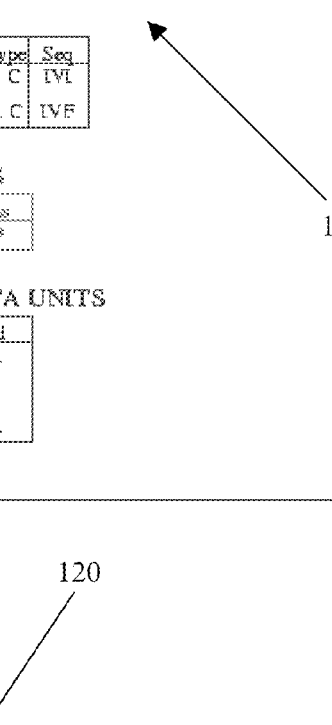
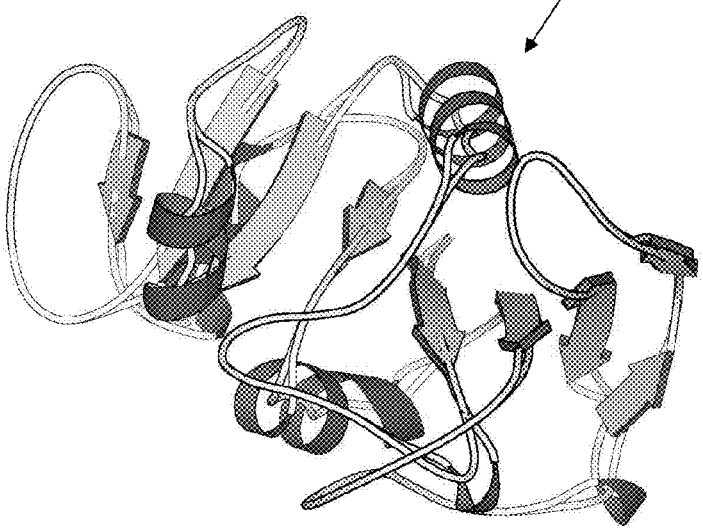
Fig 1B: Secondary structure for dihydrofolate reductase

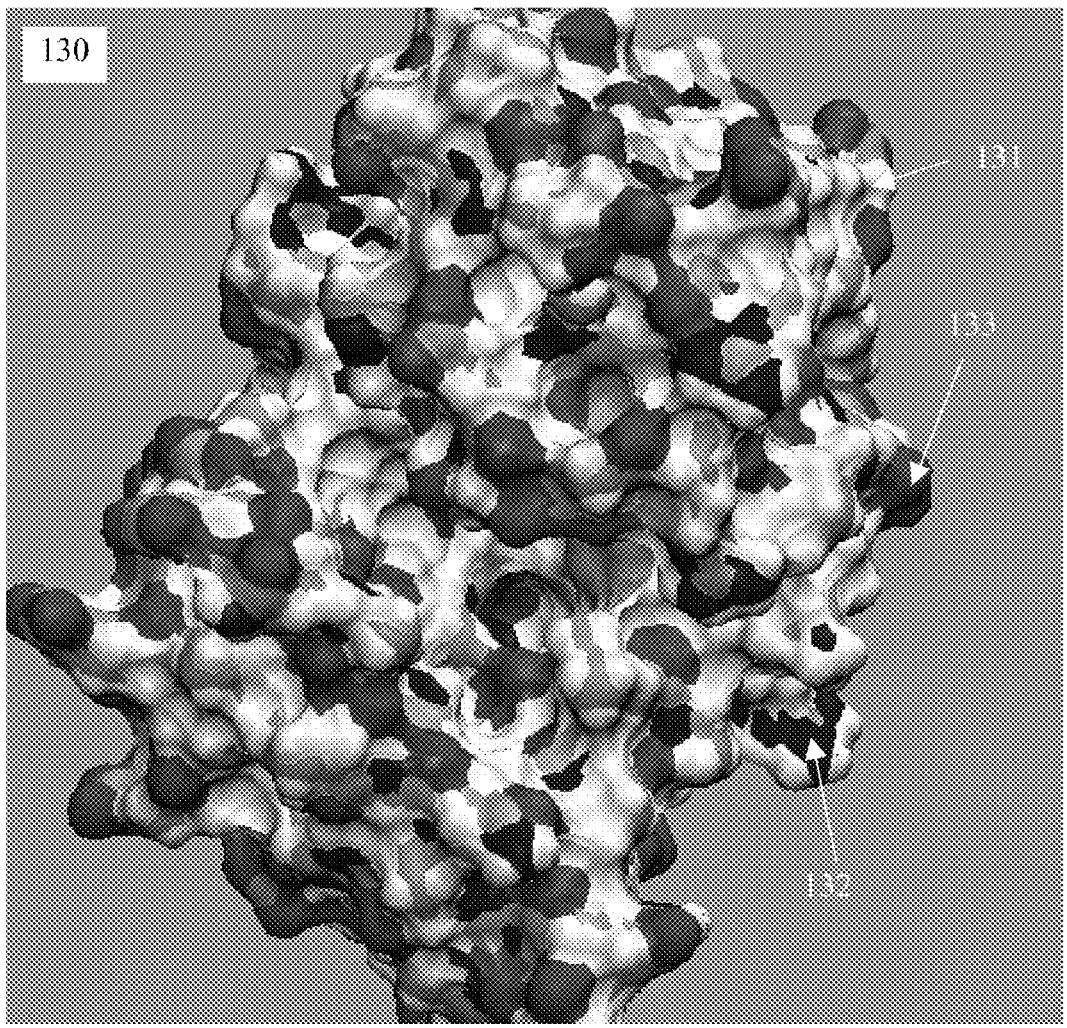
Fig 1C: Solvent Accessible surface for dihydrofolate reductase

```
HEADER     OXIDO-REDUCTASE 4DFR
COMPND     DIHYDROFOLATE REDUCTASE (E.C.1.5.1.3) COMPLEX WITH
METHOTREXATE
SOURCE     (ESCHERICHIA $COLI B), STRAIN /MB1428$,
REMARK      RESOLUTION. 1.7 ANGSTROMS.
SEQRES    1 A  159  MET ILE SER LEU ILE ALA ALA LEU ALA VAL ASP ARG VAL
...
SEQRES    9 A  159  ILE GLY MET GLU ASN ALA MET PRO TRP ASN LEU PRO ALA
HELIX     1 HBA LEU A   24  THR A   35  1
HELIX     2 HCA GLY A   43  ILE A   50  1
...
HELIX     8 HFB GLY B   96  LEU B  104  1
SHEET     1 S1A 8 THR A   73  VAL A   75  0
SHEET     2 S1A 8 LYS A   58  SER A   63  1  O  ASN A   59    N  THR A   73
...
SHEET     8 S1B 8 ASP B  132  HIS B  141 -1  N  GLU B  134    O  GLU B  157
ATOM      1   N    MET A   1      24.293  59.579   4.215  1.00 39.20
ATOM      2   CA   MET A   1      25.127  58.554   4.958  1.00 37.00
ATOM      3   C    MET A   1      24.186  58.457   6.297  1.00 35.50
ATOM      4   O    MET A   1      23.827  59.402   6.804  1.00 34.50
ATOM      5   CB   MET A   1      26.311  59.103   5.385  1.00 40.80
ATOM      6   CG   MET A   1      27.346  58.263   5.966  1.00 46.90
ATOM      7   SD   MET A   1      28.097  59.208   7.157  1.00 52.50
ATOM      8   CE   MET A   1      28.875  60.685   6.576  1.00 53.80
ATOM      9   N    ILE A   2      23.920  57.222   6.665  1.00 32.60
ATOM     10   CA   ILE A   2      23.091  56.867   7.886  1.00 30.00
...
ATOM   1269   N    ARG A 159      33.592  49.480   7.054  1.00 49.80    1
ATOM   1270   CA   ARG A 159      34.659  49.036   6.032  1.00 58.70    1
ATOM   1271   C    ARG A 159      33.951  47.793   5.282  1.00 62.30    1
ATOM   1272   O    ARG A 159      33.704  48.253   3.980  1.00 67.20    1
ATOM   1273   CB   ARG A 159      35.899  48.487   6.547  1.00 57.00    1
ATOM   1274   CG   ARG A 159      36.216  47.712   7.812  1.00 58.60    1
ATOM   1280   OXT  ARG A 159      33.513  46.695   5.892  1.00 64.50    1
TER    1281        ARG A 159
...
HETATM 1315  CL    CL A   2      11.750  52.951  20.523  1.00 28.60
HETATM 1316  O    HOH A 402      14.724  49.464  22.590   .99 25.30
HETATM 1317  O    HOH A 403      22.932  59.466  28.571  1.02 39.50
...
TER
CONECT    1    2
CONECT    2    1    3    5
CONECT    3    2    4    9
CONECT    4    3
CONECT    5    2    6
CONECT    6    5    7
CONECT    7    6    8
CONECT    8    7
CONECT    9    3   10
CONECT   10    9   11   13
...
CONECT 1250 1249
CONECT 1251 1249
CONECT 1252 1243 1253
CONECT 1253 1252 1254 1256
CONECT 1254 1253 1255 1258
CONECT 1255 1254
CONECT 1256 1253 1257
CONECT 1257 1256
CONECT 1258 1254
...
```

Fig 1D: PDB file for entry 4dfr featuring dihydrofolate reductase

C20 H22 N8 O5
210
CN(Cc1cnc2nc(N)nc(N)c2n1)c3ccc(cc3)C(=O)N[C@@H](CCC(O)=O)C(O)=O
215
Fig 2A: Chemical formula and stereo smile for Methotrexate
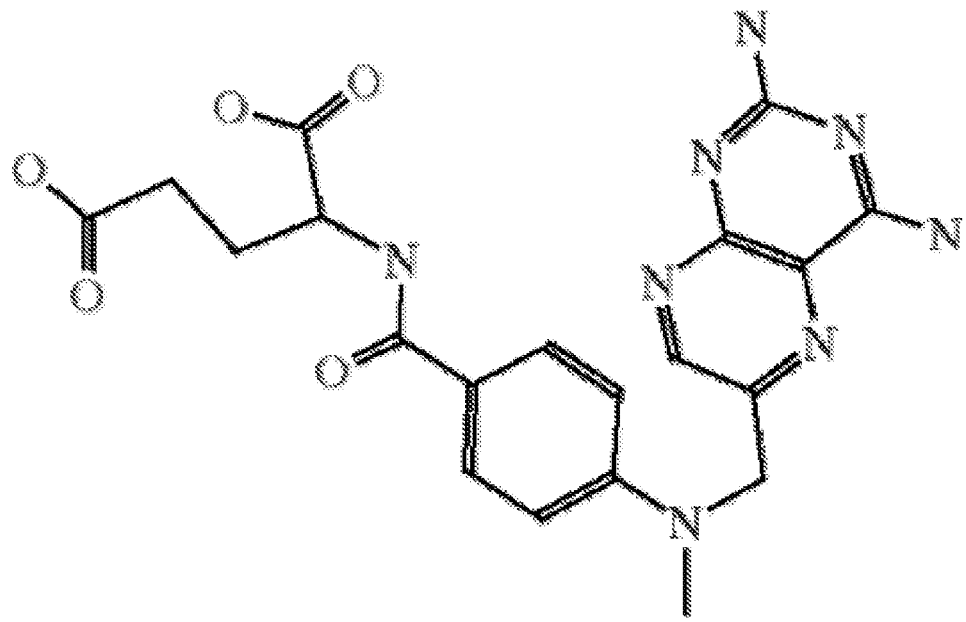
Fig 2B: 2-D representation for Methotrexate

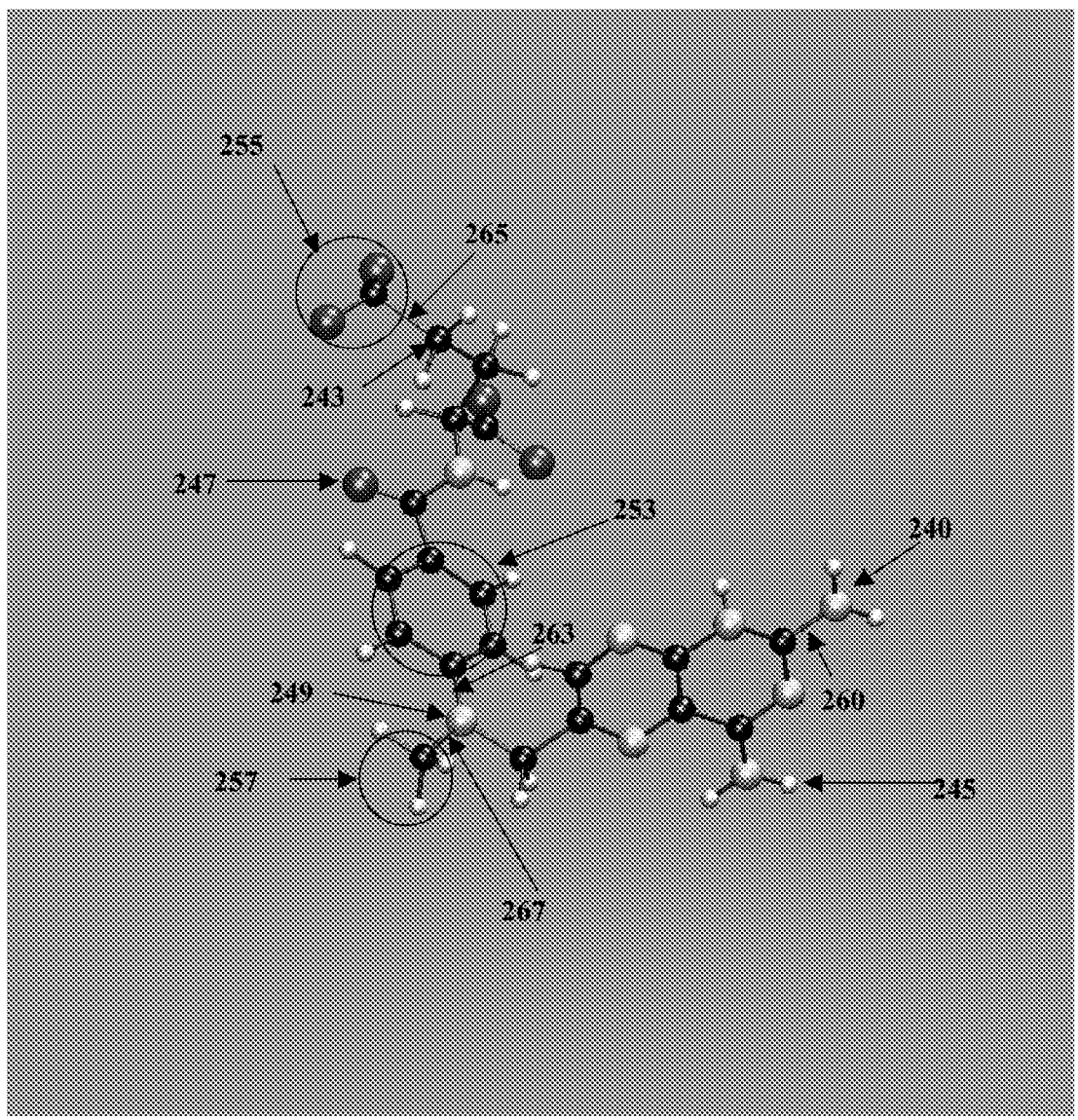
Fig 2C: Ball and stick figure of Methotrexate

```
270    273    275    277       279    280   282   285
 |      |      |      |         |      |     |     |
 ↓      ↓      ↓      ↓         ↓      ↓     ↓     ↓

@<TRIPOS>MOLECULE
    MTX
  56  58  1
@<TRIPOS>ATOM
  1    C7     19.781   59.256   25.628   C.ar  1   MTX
  2    N8     21.096   59.176   25.562   N.ar  1   MTX
  3    C8A    21.608   58.594   24.363   C.ar  1   MTX
  4    N1     22.983   58.667   24.488   N.ar  1   MTX
  5    C2     23.468   58.215   23.282   C.ar  1   MTX
  6    NA2    24.797   58.223   23.208   N.2   1   MTX
  7    HAE    25.253   57.932   22.367   H     1   MTX
  8    HAD    25.34    58.52    23.994   H     1   MTX
  9    N3     22.792   57.819   22.23    N.ar  1   MTX
 10    C4     21.459   57.803   22.068   C.ar  1   MTX
...
 35    CG     20.891   67.636   27.32    C.3   1   MTX
 36    CD     19.921   68.524   28.357   C.3   1   MTX
 37    OE2    19.441   69.469   27.489   O.3   1   MTX
 38    HAC    19.949   69.421   26.629   H     1   MTX
...
 53    H013   21.845   66.934   25.507   H     1   MTX
 54    H014   21.796   67.729   27.734   H     1   MTX
 55    H015   20.557   66.703   27.454   H     1   MTX
 56    H016   20.325   68.4     29.263   H     1   MTX
@<TRIPOS>BOND
  1    1    2    ar
  2    1    16   ar
  3    2    3    ar
  4    3    4    ar
  5    3    14   ar
  6    4    5    ar
  7    5    6    1
  8    5    9    ar
  9    6    7    1
 10    6    8    1
...
 54   34   52   1
 55   34   53   1
 56   35   54   1
 57   35   55   1
 58   36   56   1
@<TRIPOS>SUBSTRUCTURE
 1  MTX  1

291  292  293  295
```

Fig 2D: Tripos mol2 representation of Methotrexate

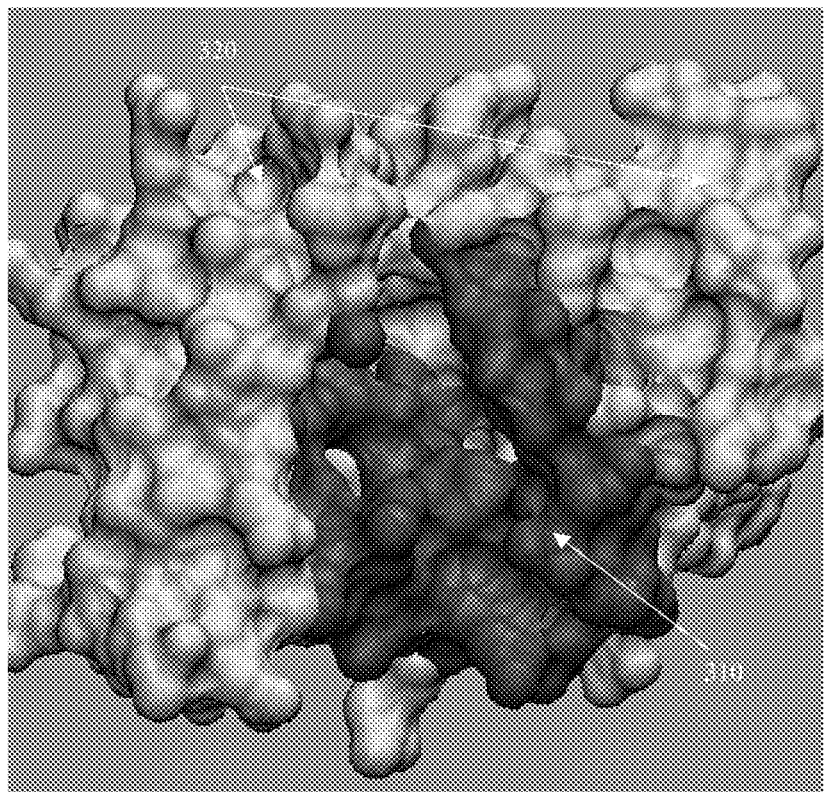
Fig 3A: Active site of dihydrofolate reductase
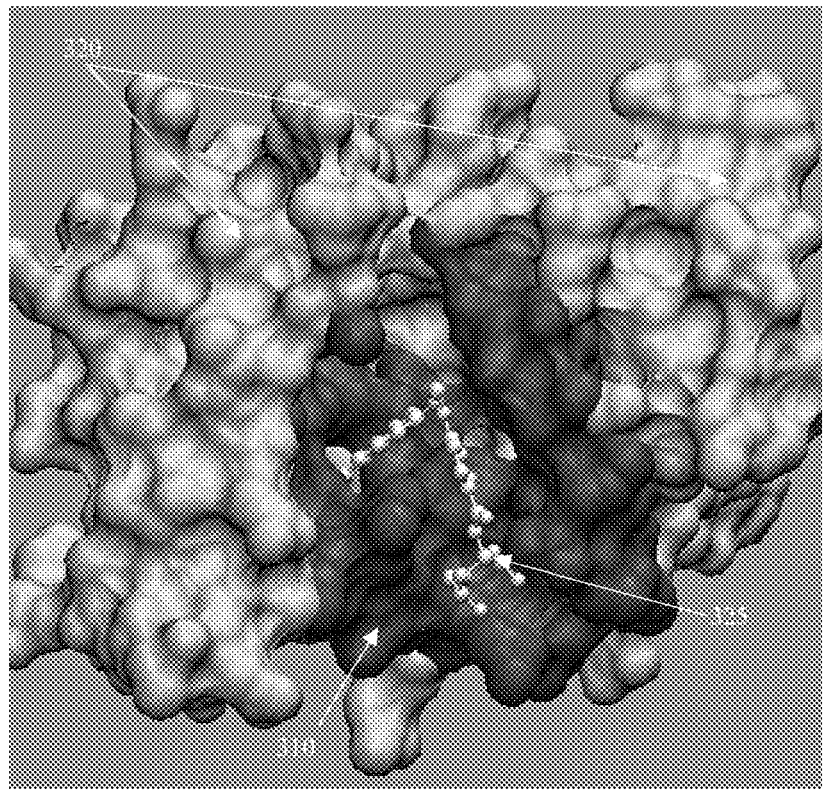
Fig 3B: Methotrexate in active site of dihydrofolate reductase

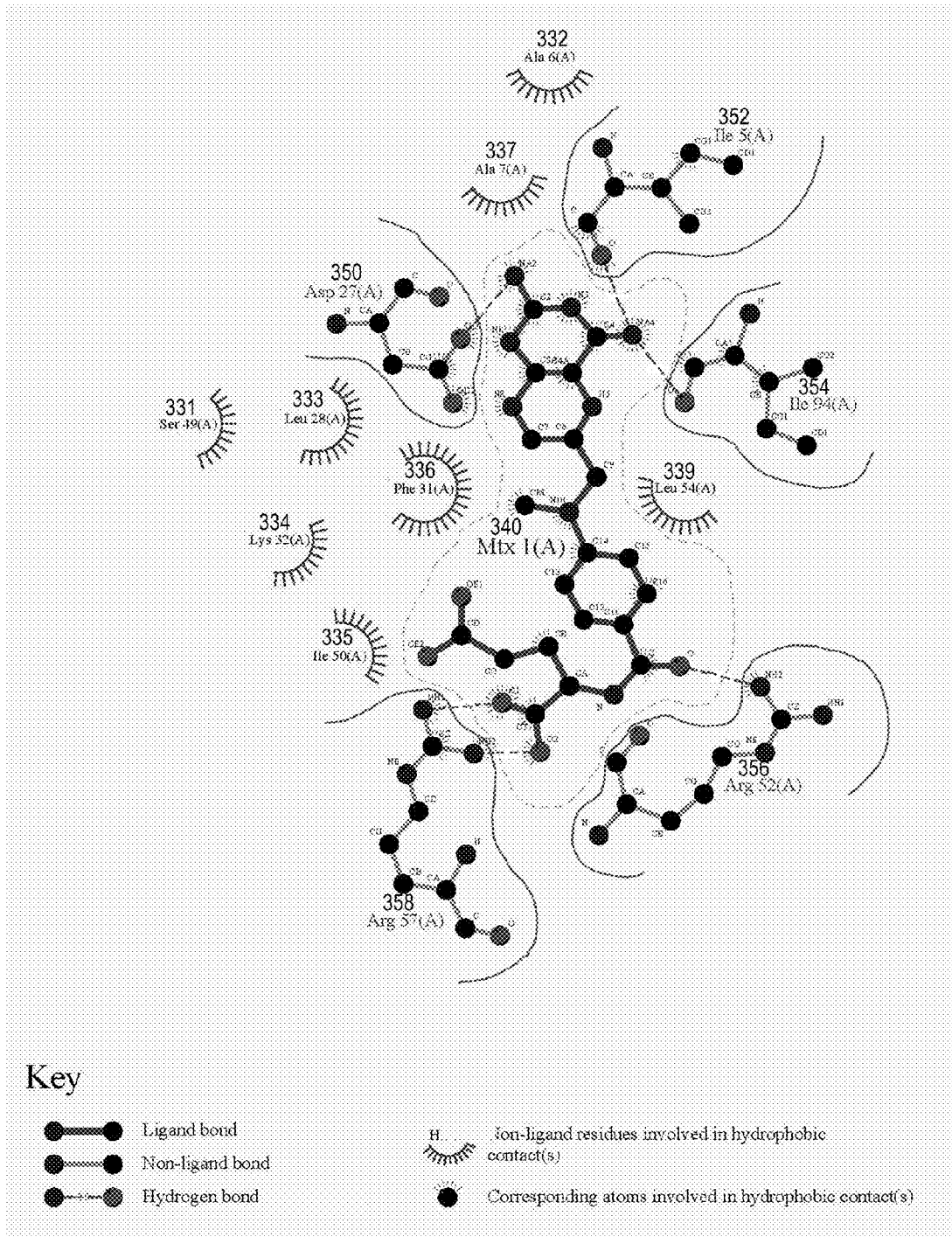
Fig 3C: Interactions between methotrexate (MTX) and dihydrofolate reductase

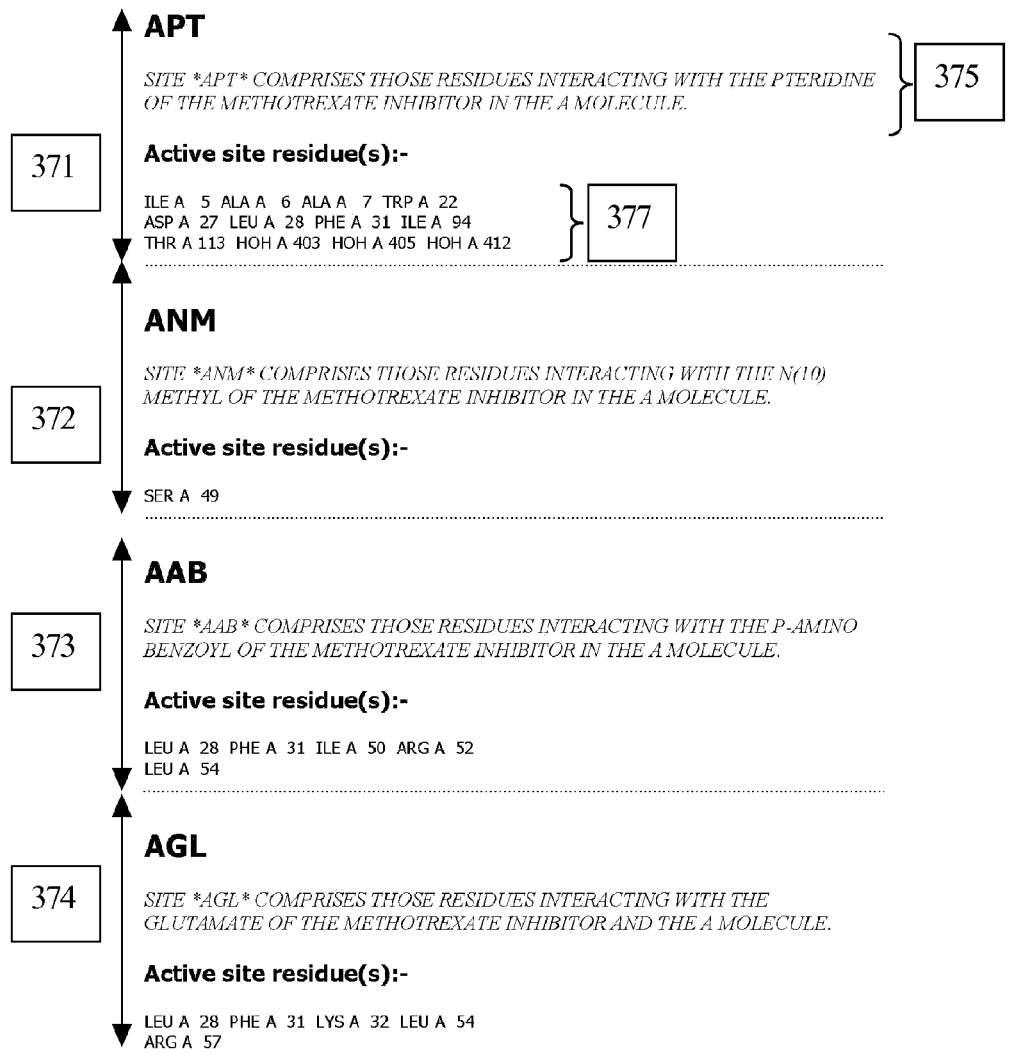
Fig 3D: Active site information for Methotrexate and PDB entry 4dfr featuring dihydrofolate reductase

Name
Dihydrofolate reductase

Other Names - Tetrahydrofolate dehydrogenase, DHFR, reductase. 7,8-dihydrofolate reductase. NADPH-dihydrofolate reductase

Source
Escherichia Coli B), Strain Mb1428, A Methotrexate-Resistant Mutant
Other sources: 1dr1 (chicken liver), 1ai9 (candida albicans), 1boz (human)

Molecular Function
Essential step for de novo glycine and purine synthesis, dna precursor synthesis, and for the conversion of dump to dtmp.

Disease Relevance
Anemia,megaloblastic,due to DHFR deficiency

Pathway
Essential step for de novo glycine and purine synthesis, dna precursor synthesis, and for the conversion of dump to dtmp.

Reaction / Process
5,6,7,8-tetrahydrofolate + NADP(+) = 7,8-dihydrofolate + Nadph (reduces folate to 5,6,7,8-tetrahydrofolate )

Classification/Family
- Functional – Oxireductases acting on CH-NH group pf donors with NAD(+) or NADP(+) as acceptor
- Structural – alpha/beta proteins
- Family - Dihydrofolate reductase family

Sequence Homologs

DR(e) Dihydrofolate reductases, eukaryotic type, DR(p) Dihydrofolate reductases, prokaryotic type Domain:1aoea_ Protein:DR (e), Species:Yeast (Candida albicans), Domain:1dyr_ Protein: DR (e), Species:Fungus (Pneumocystis carinii), Domain:1kmva_ Protein: DR (e), Species:Human (Homo sapiens), Domain:8dfr_ Protein: DR (e), Species:Chicken (Gallus gallus), Domain:1d1ga_ Protein: DR (p), Species:Thermotoga maritime, Domain:1vdra_ Protein: DR (p), Species:Haloferax volcanii , Domain:1df7a_ Protein: DR (p), Species:Mycobacterium tuberculosis, Domain:1ra9_ Protein: DR (p), Species:Escherichia coli , Domain:3dfr_ Protein: DR (p), Species:Lactobacillus casei

Secondary Structure homologs
Thioredoxin, GTP-binding protein, dihydrofolate reductase, nucleotide kinase, beta-lactamase, ricin-like protein, subtilase, periplasmic binding protein – sugar, phosphofructokinase, lactate/malate dehydrogenase, glyceraldehyde phosphate dehydrogenase, ...

Functional Homologs
Pteridine reductase, Thymidilate synthase (bi-functional domain in multiple species)

Fig 4A: Protein record

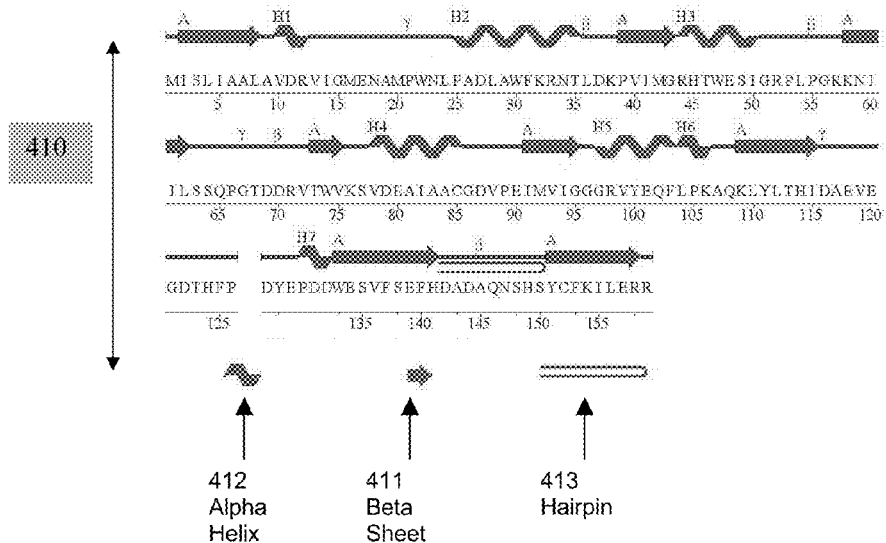
Fig 4B: Protein record (cont.)

| | 426 | 427 | 428 | 429 | 430 |
|---|---|---|---|---|---|
| | ↓ | ↓ | ↓ | ↓ | ↓ |
| 4dfr Atom | Amber Atom | Charge | Mass | VdW Radius | VdW Depth |
| N1 | N3 | 0.1592 | 14.01 | 1.8240 | 0.1700 |
| CA | CT | -0.0221 | 12.01 | 1.9080 | 0.1094 |
| C | C | 0.6123 | 12.01 | 1.9080 | 0.0860 |
| O | O | -0.5713 | 16.00 | 1.6612 | 0.2100 |
| CB | CT | 0.0865 | 12.01 | 1.9080 | 0.1094 |
| CG | CT | 0.0334 | 12.01 | 1.9080 | 0.1094 |
| SD | S | -0.2774 | 32.06 | 2.0000 | 0.2500 |
| CE | CT | -0.0341 | 12.01 | 1.9080 | 0.1094 |
| N | N3 | 0.0311 | 14.01 | 1.8240 | 0.1700 |
| CA | CT | 0.0257 | 12.01 | 1.9080 | 0.1094 |
| C | C | 0.6123 | 12.01 | 1.9080 | 0.0860 |
| O | O | -0.5713 | 16.00 | 1.6612 | 0.2100 |
| CB | CT | 0.1885 | 12.01 | 1.9080 | 0.1094 |
| CG1 | CT | -0.0387 | 12.01 | 1.9080 | 0.1094 |
| CG2 | CT | -0.3700 | 12.01 | 1.9080 | 0.1094 |
| CD1 | CT | -0.0908 | 12.01 | 1.9080 | 0.1094 |

(425 spans the above table)

Pitzer Potential: (PK/IDIVF) * (1 + cos(PN*phi - PHASE))

| 4dfr Bond | Amber BOND | IDIVF | PK | PHASE | PN |
|---|---|---|---|---|---|
| H -N3-CT-CT | X -N3-CT-X | 9 | 1.40 | 0.0 | 3.0 |
| C -CT-CT-CT | X -CT-CT-X | 9 | 1.40 | 0.0 | 3.0 |
| CT-CT-CT-S | X -CT-CT-X | 9 | 1.40 | 0.0 | 3.0 |
| CT-CT-S -CT | X -CT-S -X | 3 | 1.00 | 0.0 | 3.0 |
| CT-S -CT-H | X -S -CT-X | 3 | 1.00 | 0.0 | 3.0 |
| H -N3-CT-CT | X -N3-CT-X | 9 | 1.40 | 0.0 | 3.0 |
| C -CT-CT-CT | X -CT-CT-X | 9 | 1.40 | 0.0 | 3.0 |

(431 spans the above table; 432 brackets the last three columns)

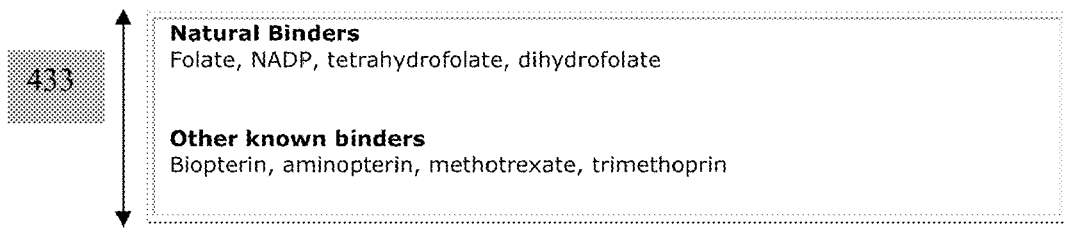

433

Natural Binders
Folate, NADP, tetrahydrofolate, dihydrofolate

Other known binders
Biopterin, aminopterin, methotrexate, trimethoprin

Fig 4C: Protein record (cont.)

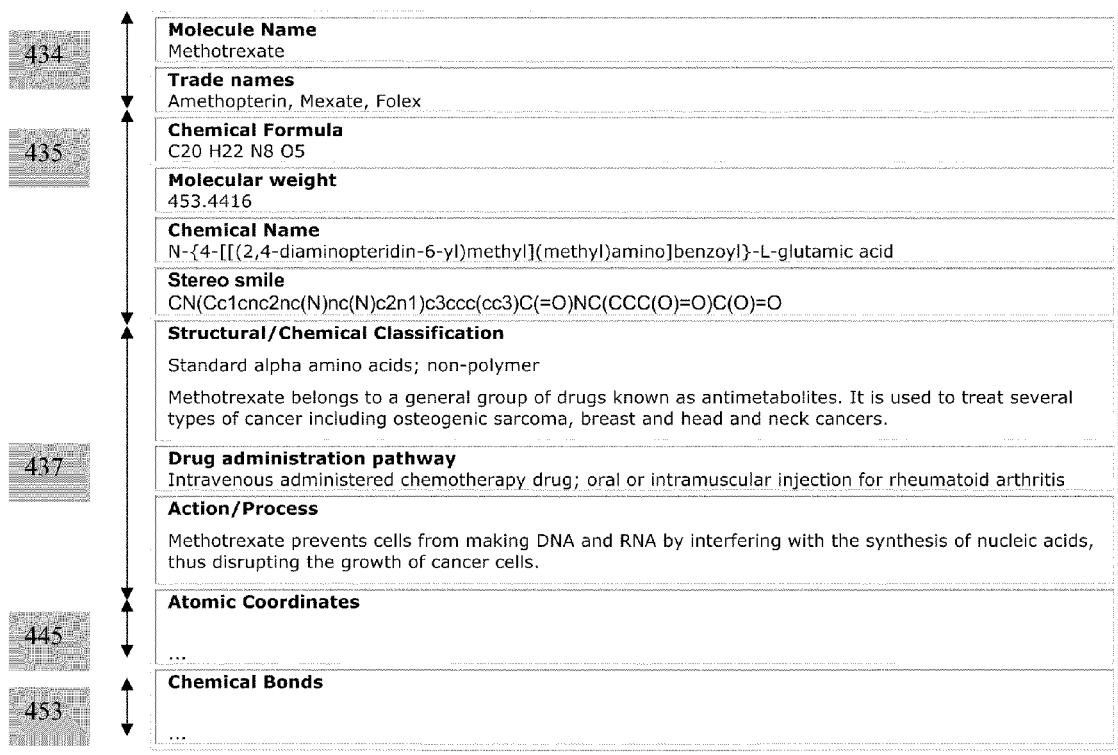
Fig 5A: Lead candidate record

| 4dfir Atom | Amber Atom | Charge | Mass | VdW Radius | VdW Depth |
|---|---|---|---|---|---|
| N1 | NT | 0.1571 | 14.01 | 1.8240 | 0.1700 |
| C2 | CM | -0.0211 | 12.01 | 1.9080 | 0.0860 |
| NA2 | NT | 0.2746 | 14.01 | 1.8240 | 0.1700 |
| N3 | N2 | -0.3253 | 14.01 | 1.8240 | 0.1700 |
| C4 | CM | 0.0724 | 12.01 | 1.9080 | 0.0860 |
| NA4 | NT | 0.3867 | 14.01 | 1.8240 | 0.1700 |
| C4A | CD | -0.1444 | 12.01 | 1.9080 | 0.0860 |
| N5 | NC | -0.0303 | 14.01 | 1.8240 | 0.1700 |
| C6 | CM | -0.0100 | 12.01 | 1.9080 | 0.0860 |
| C7 | CM | -0.0582 | 12.01 | 1.9080 | 0.0860 |
| N8 | NC | 0.0543 | 14.01 | 1.8240 | 0.1700 |
| C8A | CM | -0.1038 | 12.01 | 1.9080 | 0.0860 |
| C9 | CT | -0.0544 | 12.01 | 1.9080 | 0.1094 |
| N10 | N2 | 0.0215 | 14.01 | 1.8240 | 0.1700 |
| CM | CT | -0.0805 | 12.01 | 1.9080 | 0.1094 |
| C11 | CA | -0.1230 | 12.01 | 1.9080 | 0.0860 |
| C12 | CA | -0.0146 | 12.01 | 1.9080 | 0.0860 |
| C13 | CA | -0.1936 | 12.01 | 1.9080 | 0.0860 |
| C14 | CA | -0.0392 | 12.01 | 1.9080 | 0.0860 |
| C15 | CA | -0.1960 | 12.01 | 1.9080 | 0.0860 |
| C16 | CA | -0.0365 | 12.01 | 1.9080 | 0.0860 |
| C | C | 0.2424 | 12.01 | 1.9080 | 0.0860 |
| O | O | -0.4187 | 16.00 | 1.6612 | 0.2100 |
| N | N | 0.0791 | 14.01 | 1.8240 | 0.1700 |
| CA | CT | -0.1036 | 12.01 | 1.9080 | 0.1094 |
| CT | C | 0.4000 | 12.01 | 1.9080 | 0.0860 |
| O1 | O2 | -0.7173 | 16.00 | 1.6612 | 0.2100 |
| OC | O2 | -0.5761 | 16.00 | 1.6612 | 0.2100 |
| CB | CT | -0.0699 | 12.01 | 1.9080 | 0.1094 |
| OG | CT | -0.2188 | 12.01 | 1.9080 | 0.1094 |
| CD | C | 0.4453 | 12.01 | 1.9080 | 0.0860 |
| OE1 | O2 | -0.6396 | 16.00 | 1.6612 | 0.2100 |
| OE2 | O2 | -0.5993 | 16.00 | 1.6612 | 0.2100 |

Pitzer Potential: (PK/IDIVF) * (1 + cos(PN*phi - PHASE) )

| 4dfir Bond | Amber BOND | IDIVF | PK | PHASE | PN |
|---|---|---|---|---|---|
| O2-C -CT-N | X -C -CT-X | 4 | 0.00 | 0.0 | 2.0 |
| O2-C -CT-CT | X -C -CT-X | 4 | 0.00 | 0.0 | 2.0 |
| C -CT-CT-CT | X -CT-CT-X | 9 | 1.40 | 0.0 | 3.0 |
| CT-CT-CT-N | X -CT-CT-X | 9 | 1.40 | 0.0 | 3.0 |
| CT-CT-N -C | CT-CT-N -C | 1 | 0.53 | 0.0 | 1.0 |
| CA-C -N -CT | X -C -N -X | 4 | 10.00 | 180.0 | 2.0 |
| N -C -CA-CA | X -C -CA-X | 4 | 14.50 | 180.0 | 2.0 |
| CA-CA-N2-CT | X -CA-N2-X | 4 | 9.60 | 180.0 | 2.0 |
| H -CT-N2-CT | X -CT-NC-X | 6 | 0.00 | 0.0 | 3.0 |
| CM-CT-N2-CT | X -CT-N2-X | 6 | 0.00 | 0.0 | 3.0 |
| CM-CM-CT-N2 | X -CM-CT-X | 6 | 0.00 | 0.0 | 3.0 |

455

457

Fig 5B: Lead candidate record (cont.)

Other targets MTX binds to

1ao8, 1axw, 1dlg, 1ddr, 1dds, 1df7, 1dhi, 1dhj, 1dls, 1dra, 1drb, 1dre, 1e7w, 1mxf, 1p33, 1ra3, 1rb3, 1rg7, 1rh3, 1rx3, 1tdr, 2drc, 3cd2, 3dfr, 3drc

ADMET

High absorption rates
May be taken orally or intravenous (anti-cancer) or via intramuscular injection (anti-rheumatoid arthritis)
Metabolically stable over period of days
Toxic at medium and high dosages
High risk of drug cross-reactions, especially in regards to renal excretion
Possibly fatal drug interaction with trimethoprim
Does not selectively distinguish between healthy and cancer / defective cells

Side Effects

Life threatening: Hives, rash, intense itching,
Common: Black stools/bloody vomit. Sore throat, fever, mouth sores; chills; unusual bleeding or bruising. Abdominal pain, nausea, vomiting.
Infrequent: Seizures, Dizziness, drowsiness, headache, confusion, blurred vision, shortness of breath, joint pain, blood in urine, jaundice, diarrhea, red skin, back pain. Cough, rash, sexual difficulties in male. Acne, boils, hair loss, itchy skin.
Rare: Convulsions. Painful urination.

Fig 5C: Lead candidate record (cont.)

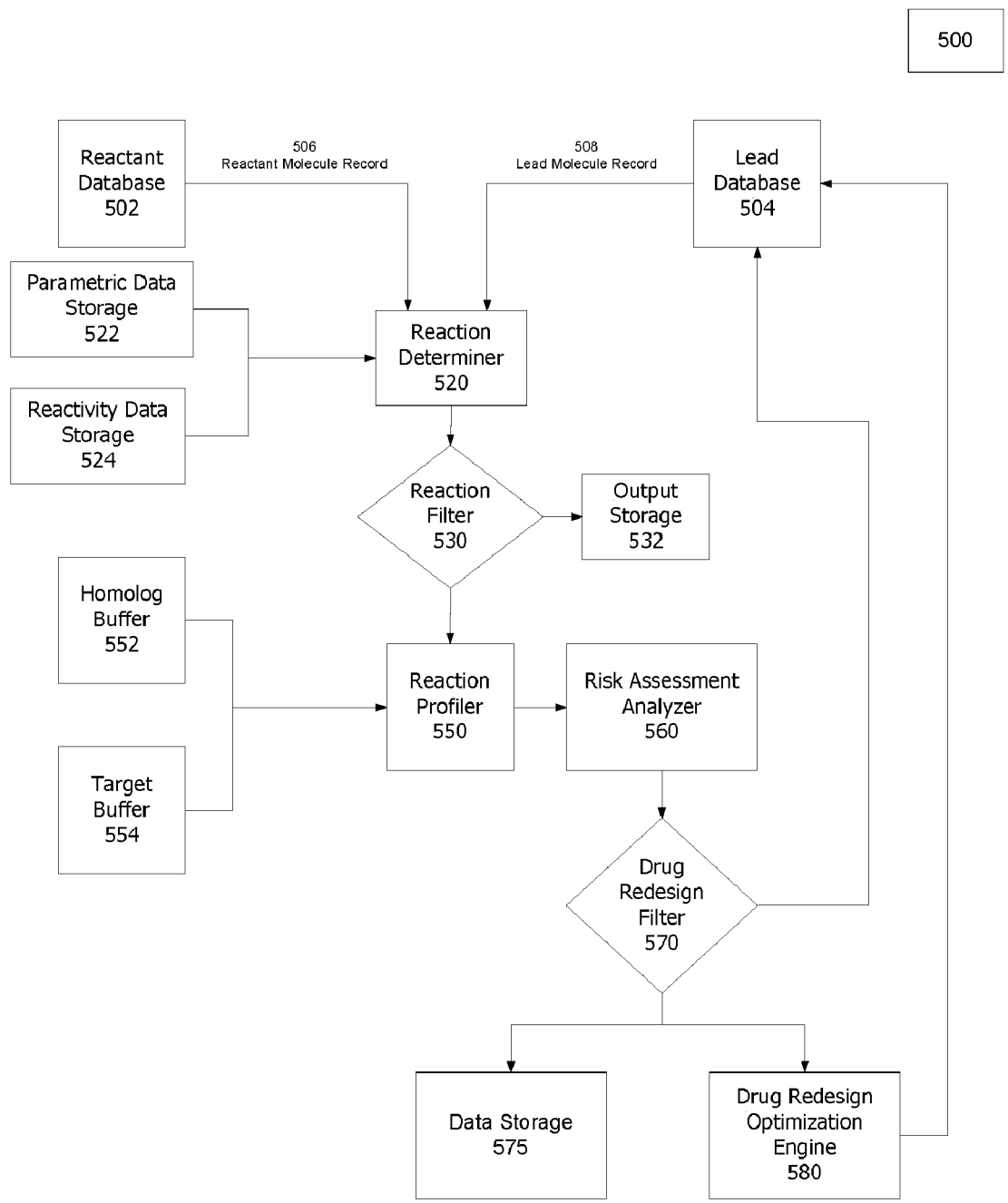
Fig 6: Modeling system

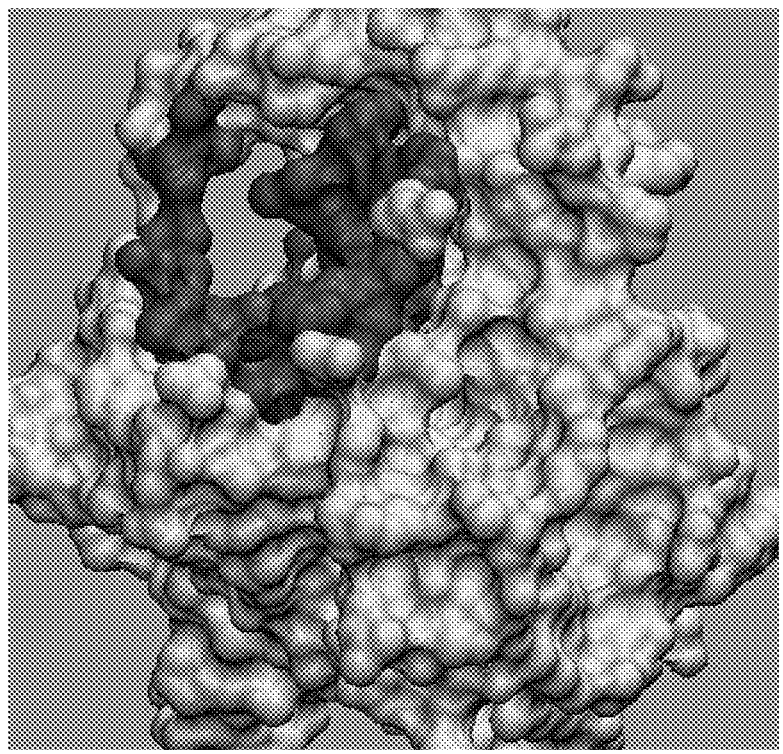
Fig 7A: Active site of E. Coli thymidylate synthase
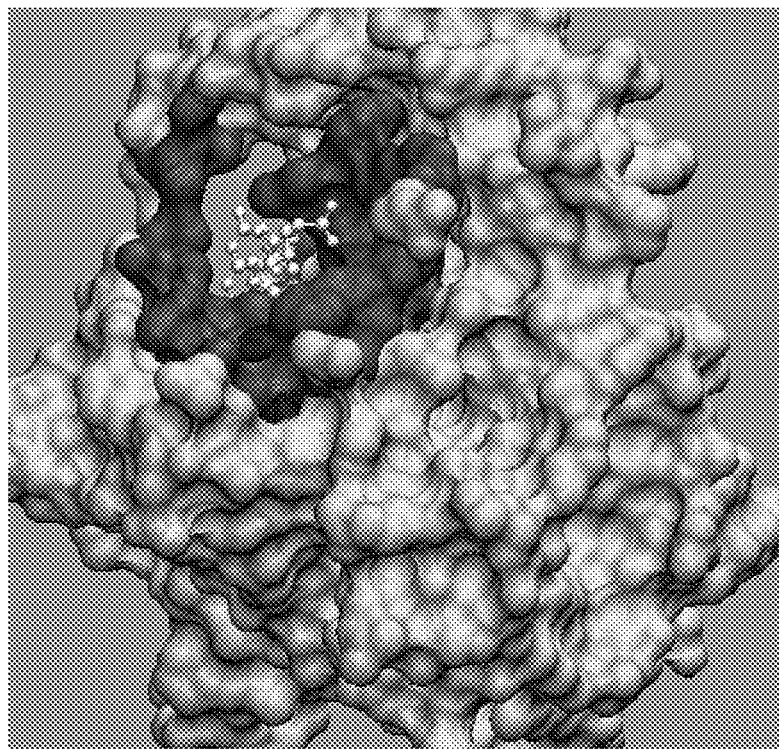
Fig 7B: Methotrexate in active site of E. Coli thymidylate synthase

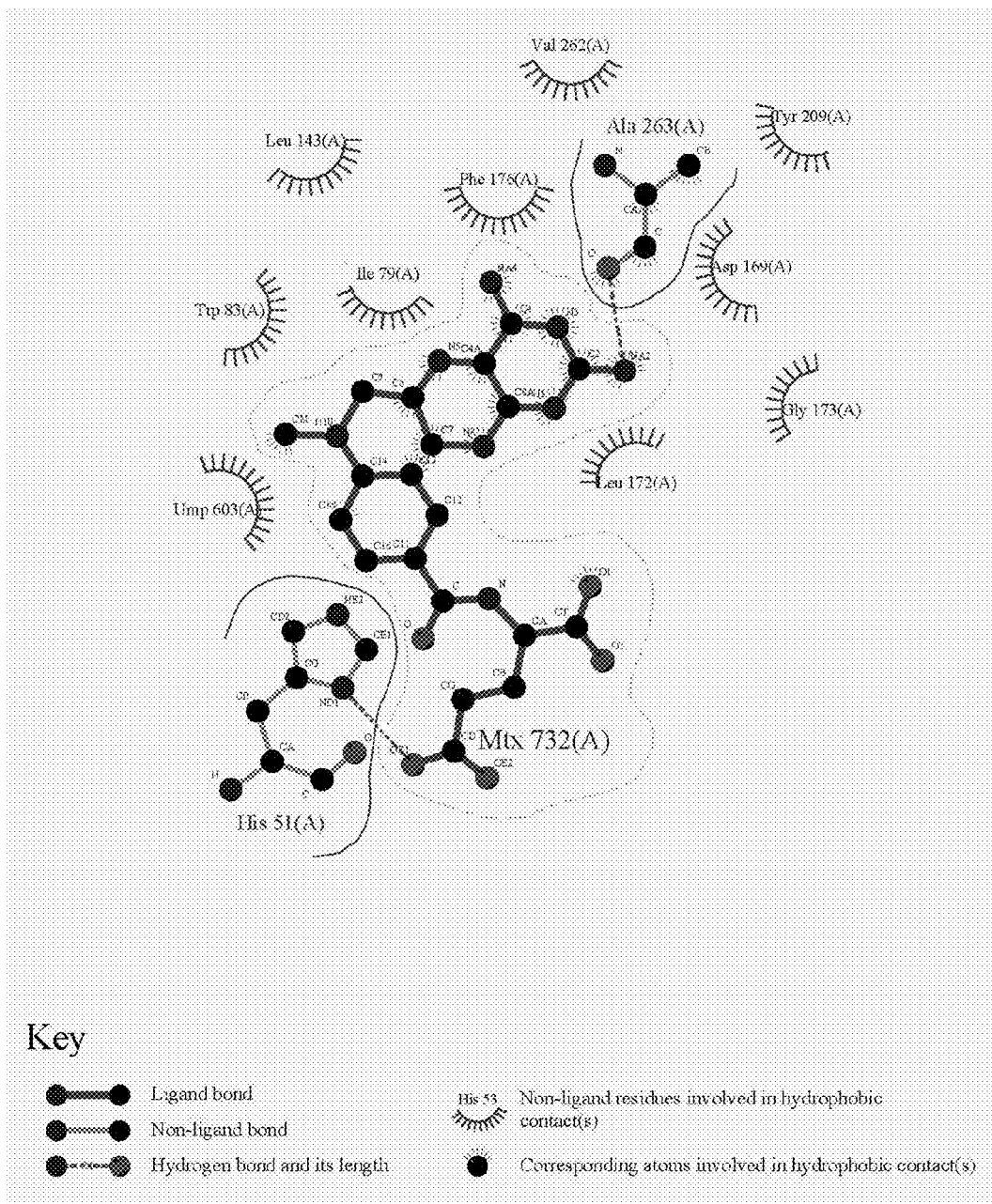
Fig 7C: Interactions of methotrexate (MTX) with E coli thymidylate synthase

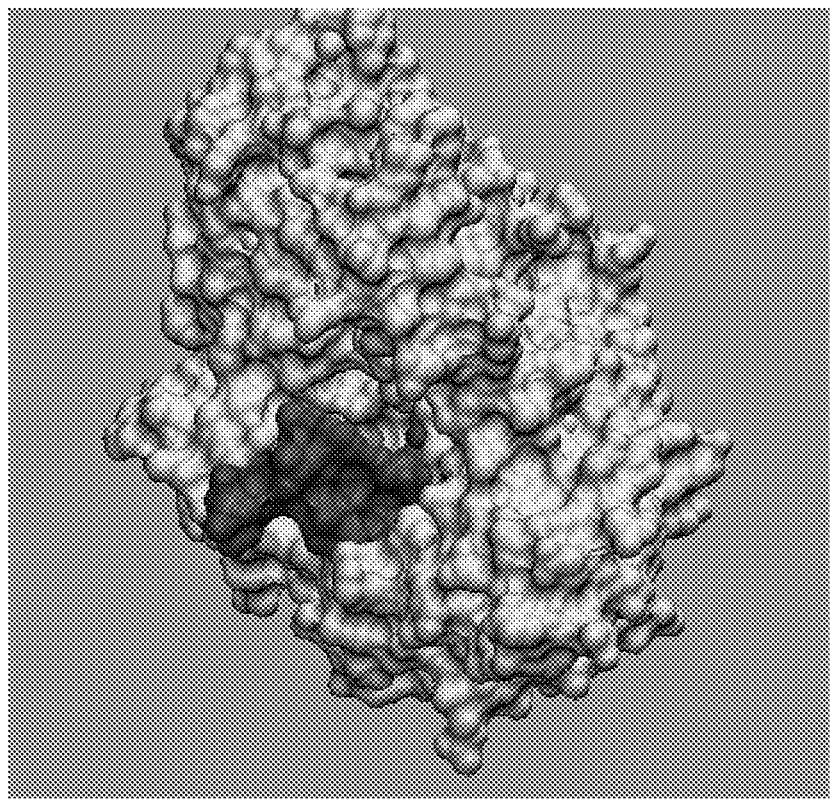
Fig 8A: Active site of serine hydroxymethyl transferase
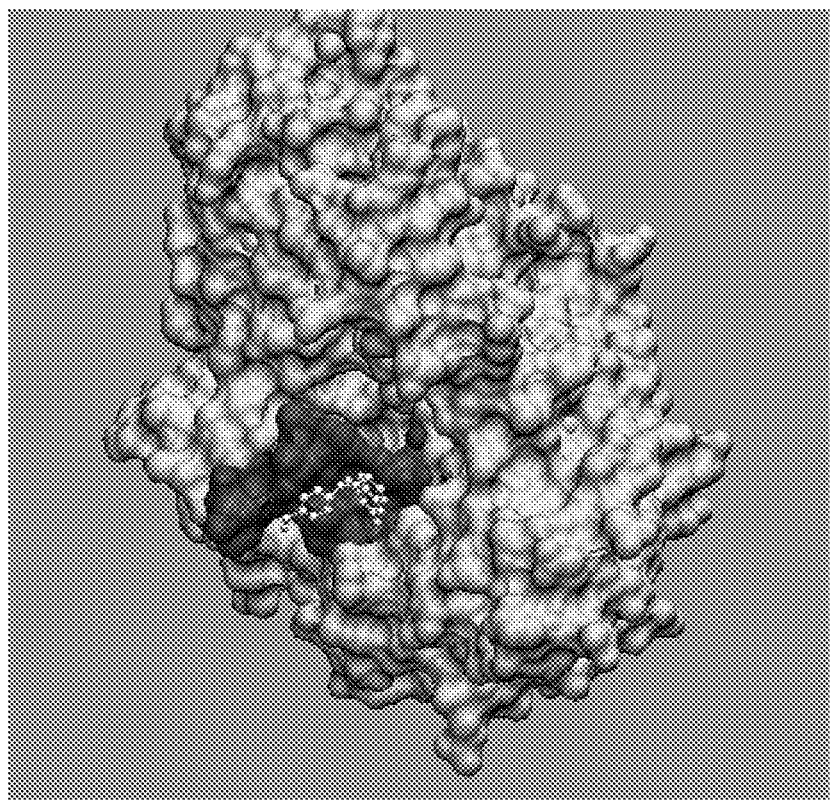
Fig 8B: Folinic acid in active site of serine hydroxymethyl transferase

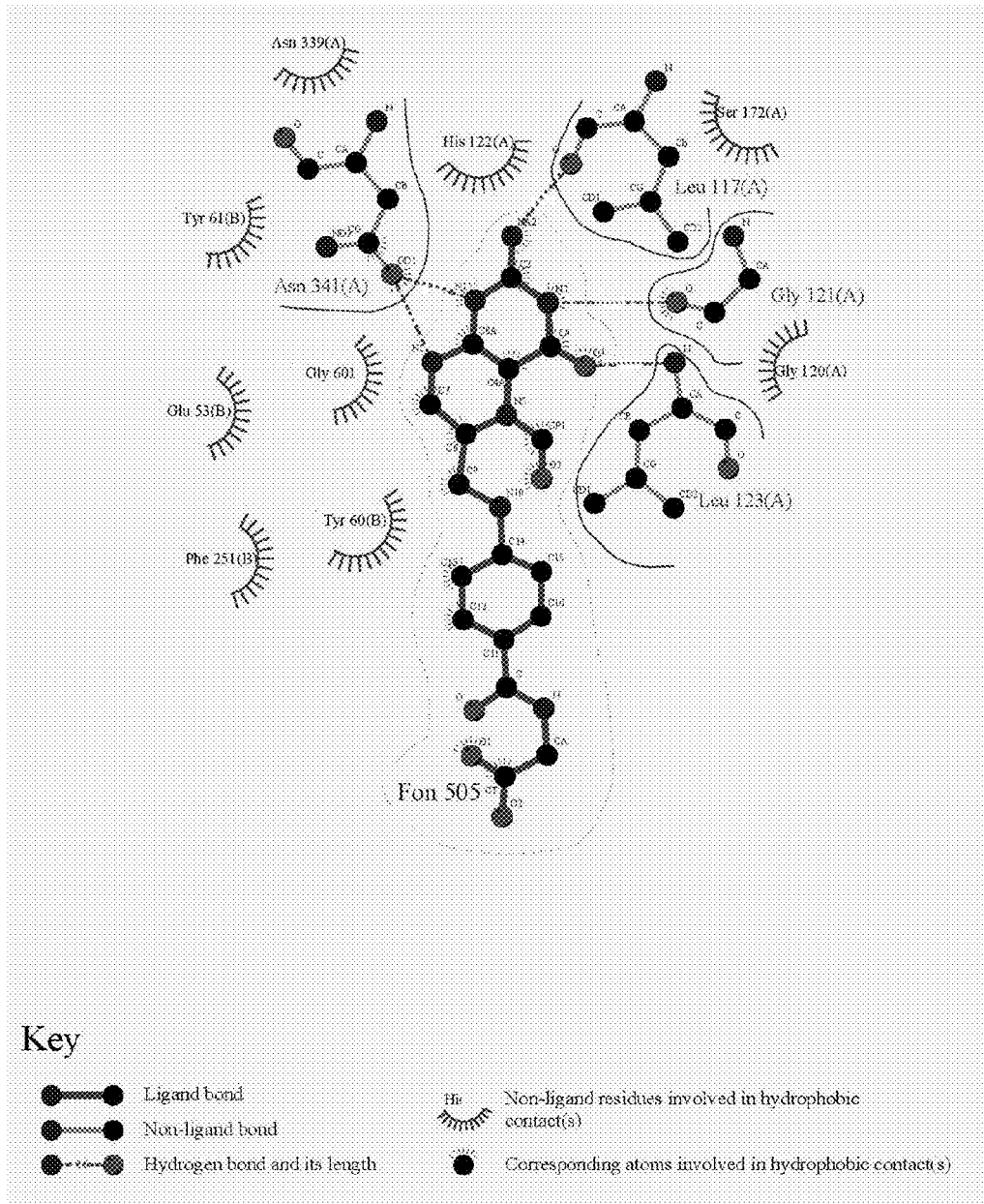
Fig 8C: Interactions of folinic acid (FON) in the active site of serine hydroxymethyl transferase

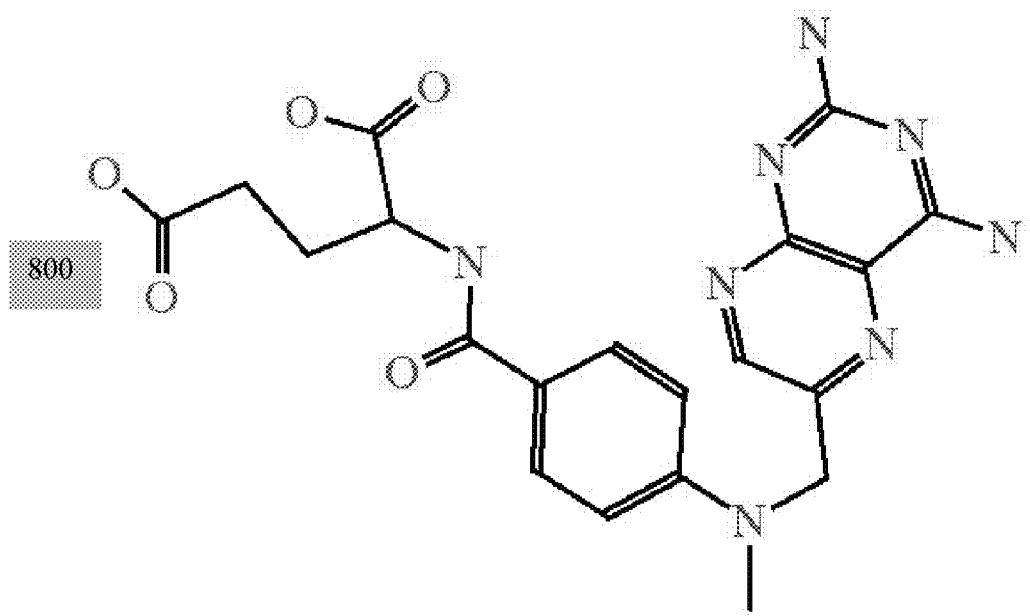
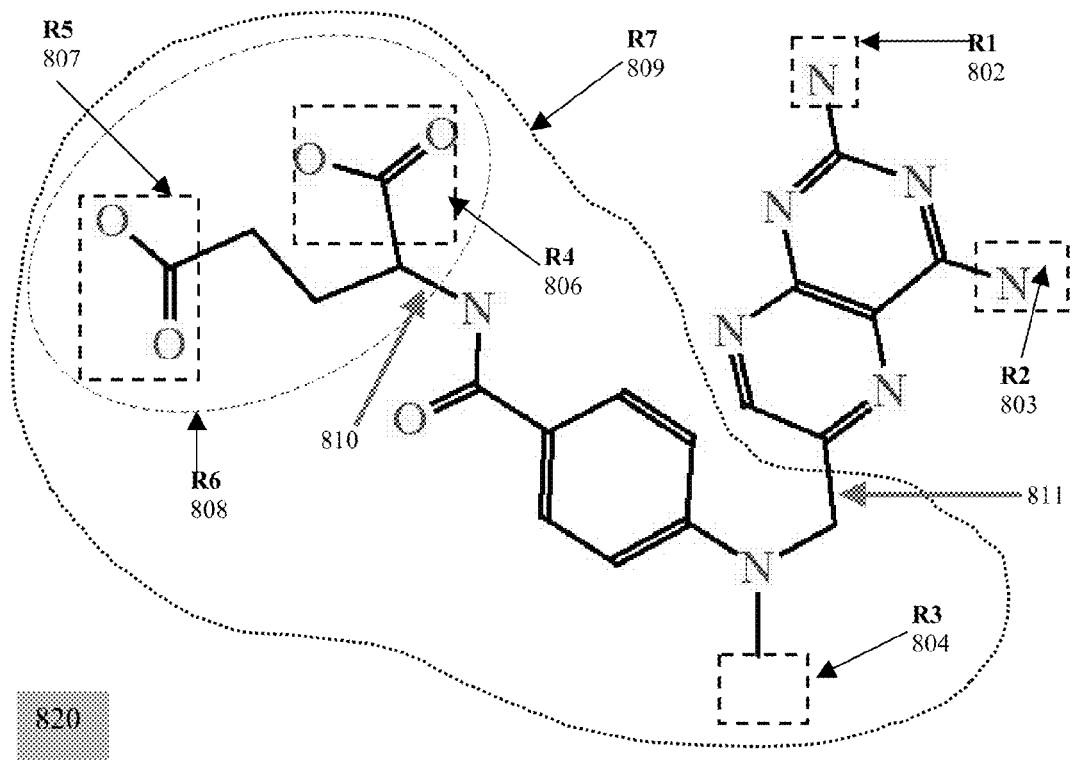
Fig 9A

| Chemical Entity | Examples |
|---|---|
| Alkyl (R = $C_nH_{2n+1}$) | H, $CH_3$ |
| Ester(R-C-OO-R') | Methyl formate |
| Peptidic | Serine, Phenylalanine |
| Nucleic acid bases | Thymine, Guanine |
| Aromatic | Benzene, Pteridine |
| ... | ... |
| Element | Oxygen, nitrogen, sulphur, chlorine |

830

Fig 9B

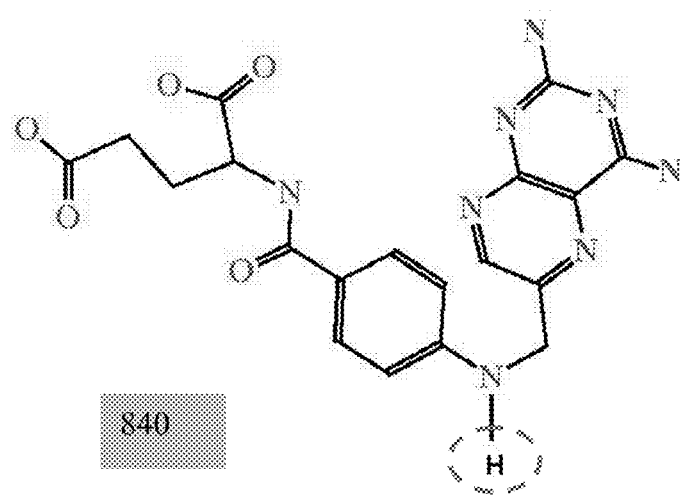
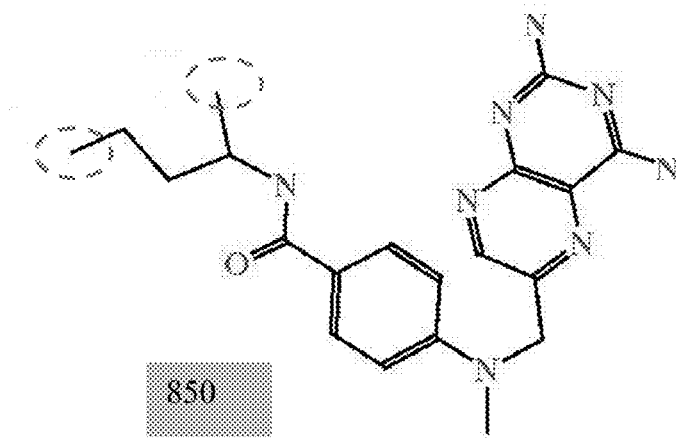
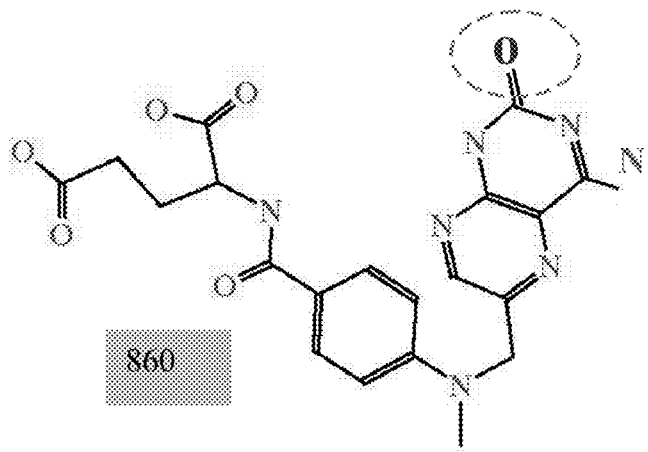
Fig 10A

SEQUENCE LISTING

<160> NUMBER OF SEQ ID NOS: 7

<210> SEQ ID NO 1
<211> LENGTH: 159
<212> TYPE: PRT
<213> ORGANISM: Escherichia coli
<220> FEATURE:
<223> OTHER INFORMATION: dihydrofolate reductase (DHFR) target
      biopolymer

<400> SEQUENCE: 1

Met Ile Ser Leu Ile Ala Ala Leu Ala Val Asp Arg Val Ile Gly Met
1               5                   10                  15

Glu Asn Ala Met Pro Trp Asn Leu Pro Ala Asp Leu Ala Trp Phe Lys
            20                  25                  30

Arg Asn Thr Leu Asp Lys Pro Val Ile Met Gly Arg His Thr Trp Glu
        35                  40                  45

Ser Ile Gly Arg Pro Leu Pro Gly Arg Lys Asn Ile Ile Leu Ser Ser
    50                  55                  60

Gln Pro Gly Thr Asp Asp Arg Val Thr Trp Val Lys Ser Val Asp Glu
65                  70                  75                  80

Ala Ile Ala Ala Cys Gly Asp Val Pro Glu Ile Met Val Ile Gly Gly
                85                  90                  95

Gly Arg Val Tyr Glu Gln Phe Leu Pro Lys Ala Gln Lys Leu Tyr Leu
            100                 105                 110

Thr His Ile Asp Ala Glu Val Glu Gly Asp Thr His Phe Pro Asp Tyr
        115                 120                 125

Glu Pro Asp Asp Trp Glu Ser Val Phe Ser Glu Phe His Asp Ala Asp
    130                 135                 140

Ala Gln Asn Ser His Ser Tyr Cys Phe Lys Ile Leu Glu Arg Arg
145                 150                 155

<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence:DHFR
      positions 35-38 Type II beta-turn

<400> SEQUENCE: 2

Thr Leu Asp Lys
  1

<210> SEQ ID NO 3
<211> LENGTH: 4
<212> TYPE: PRT
<213> ORGANISM: Artificial Sequence
<220> FEATURE:
<223> OTHER INFORMATION: Description of Artificial Sequence:DHFR
      positions 54-57 Type II beta-turn

<400> SEQUENCE: 3

Leu Pro Gly Arg
  1

<210> SEQ ID NO 4
<211> LENGTH: 4
<212> TYPE: PRT
<213> ORGANISM: Artificial Sequence
<220> FEATURE:

```
-continued

<223> OTHER INFORMATION: Description of Artificial Sequence:DHFR
      positions 69-72 Type I beta-turn

<400> SEQUENCE: 4

Asp Asp Arg Val
  1

<210> SEQ ID NO 5
<211> LENGTH: 4
<212> TYPE: PRT
<213> ORGANISM: Artificial Sequence
<220> FEATURE:
<223> OTHER INFORMATION: Description of Artificial Sequence:DHFR
      positions 144-147 Type I beta-turn

<400> SEQUENCE: 5

Asp Ala Gln Asn
  1

<210> SEQ ID NO 6
<211> LENGTH: 13
<212> TYPE: PRT
<213> ORGANISM: Artificial Sequence
<220> FEATURE:
<223> OTHER INFORMATION: Description of Artificial Sequence:PDB file for
      entry 4dfr dihydrofolate reductase SEQRES 1 DHFR
      peptide

<400> SEQUENCE: 6

Met Ile Ser Leu Ile Ala Ala Leu Ala Val Asp Arg Val
  1               5                  10

<210> SEQ ID NO 7
<211> LENGTH: 13
<212> TYPE: PRT
<213> ORGANISM: Artificial Sequence
<220> FEATURE:
<223> OTHER INFORMATION: Description of Artificial Sequence:PDB file for
      entry 4dfr dihydrofolate reductase SEQRES 9 DHFR
      peptide

<400> SEQUENCE: 7

Ile Gly Met Glu Asn Ala Met Pro Trp Asn Leu Pro Ala
  1               5                  10
```

LEAD MOLECULE CROSS-REACTION PREDICTION AND OPTIMIZATION SYSTEM

CROSS-REFERENCES TO RELATED APPLICATIONS

The present application claims priority from and is a non provisional application of U.S. Provisional Application No. 60/511,474, entitled "Lead Molecule Cross Reaction Prediction and Optimization Process" filed Oct. 14, 2003, the entire contents of which are herein incorporated by reference for all purposes.

The present disclosure is related to the commonly assigned U.S. patent application Ser. No. 10/967,085, filed on Oct. 14, 2004, entitled "Method and Apparatus for Analysis of Molecular Configurations and Combinations" to Prakash et al. (hereinafter "Prakash I"), the entire contents of which are incorporated herein by reference in its entirety for all purposes.

FIELD OF THE INVENTION

The present invention generally relates to bioinformatics, proteomics, molecular modeling, computer aided molecular design (CAMD), and more specifically computer aided drug design (CADD) and computational modeling of molecular combinations.

BACKGROUND OF THE INVENTION

An explanation of conventional drug discovery processes and their limitations is useful for understanding the present invention.

Discovering a new drug to treat or cure some biological condition, is a lengthy and expensive process, typically taking on average 12 years and $800 million per drug, and taking possibly up to 15 years or more and $1 billion to complete in some cases. The process may include wet lab testing/experiments, various biochemical and cell-based assays, animal models, and also computational modeling in the form of computational tools in order to identify, assess, and optimize potential chemical compounds that either serve as drugs themselves or as precursors to eventual drug molecules.

A goal of a drug discovery process is to identify and characterize a chemical compound or ligand, i.e., binder, biomolecule, that affects the function of one or more other biomolecules (i.e., a drug "target") in an organism, usually a biopolymer, via a potential molecular interaction or combination. Herein the term biopolymer refers to a macromolecule that comprises one or more of a protein, nucleic acid (DNA or RNA), peptide or nucleotide sequence or any portions or fragments thereof. Herein the term biomolecule refers to a chemical entity that comprises one or more of a biopolymer, carbohydrate, hormone, or other molecule or chemical compound, either inorganic or organic, including, but not limited to, synthetic, medicinal, drug-like, or natural compounds, or any portions or fragments thereof. The target molecule is typically a disease-related target protein or nucleic acid for which it is desired to affect a change in function, structure, and/or chemical activity in order to aid in the treatment of a patient disease or other disorder. In other cases, the target is a biomolecule found in a disease-causing organism, such as a virus, bacteria, or parasite, that when affected by the drug will affect the survival or activity of the infectious organism. In yet other cases, the target is a biomolecule of a defective or harmful cell such as a cancer cell. In yet other cases the target is an antigen or other environmental chemical agent that may induce an allergic reaction or other undesired immunological or biological response.

The ligand is typically what is known as a small molecule drug or chemical compound with desired drug-like properties in terms of potency, low toxicity, membrane permeability, solubility, chemical/metabolic stability, etc. In other cases, the ligand may be biologic such as an injected protein-based or peptide-based drug or even another full-fledged protein. In yet other cases, the ligand may be a chemical substrate of a target enzyme. The ligand may even be covalently bound to the target or may in fact be a portion of the protein, e.g., protein secondary structure component, protein domain containing or near an active site, protein sub-unit of an appropriate protein quaternary structure, etc.

Throughout the remainder of the background discussion, unless otherwise specifically differentiated, a (potential) molecular combination will feature one ligand and one target, the ligand and target will be separate chemical entities, and the ligand will be assumed to be a chemical compound while the target will typically be a biological protein (mutant or wild type). Note that the frequency of nucleic acids (both DNA/RNA) as targets will likely increase in coming years as advances in gene therapy and pathogenic microbiology progress. Also the term "molecular complex" will refer to the bound state between the target and ligand when interacting with one another in the midst of a suitable (often aqueous) environment. A "potential" molecular complex refers to a bound state that may occur albeit with low probability and therefore may or may not actually form under normal conditions.

The drug discovery process itself typically includes four different sub-processes: (1) target validation; (2) lead generation/optimization; (3) preclinical testing; and (4) clinical trials and approval.

Target validation includes determination of one or more targets that have disease relevance and usually takes two-and-a-half years to complete. Results of the target validation phase might include a determination that the presence or action of the target molecule in an organism causes or influences some effect that initiates, exacerbates, or contributes to a disease for which a cure or treatment is sought. In some cases a natural binder or substrate for the target may also be determined via experimental methods.

Lead generation typically involves the identification of lead compounds, i.e., ligands that can bind to the target molecule, that may alter the effects of the target through either activation, deactivation, catalysis, or inhibition of the function of the target, in which case the lead would be a viewed as a suitable candidate ligand to be used in the drug application process. Lead optimization involves the chemical and structural refinement of lead candidates into drug precursors in order to improve binding affinity to the desired target, increase selectivity, and to address basic issues of toxicity, solubility, and metabolism. Together lead generation and lead optimization typically takes about three years to complete and might result in one or more chemically distinct leads for further consideration.

In preclinical testing, biochemical assays and animal models are used to test the selected leads for various pharmacokinetic factors related to drug absorption and membrane permeability, distribution, metabolism, excretion, toxicity, side effects, and required dosages. This preclinical testing takes approximately one year. After the preclinical testing period, clinical trials and approval take another six to eight or more years during which the drug candidates are tested on human subjects for safety and efficacy. Part of the exorbitant expense of today's drug discovery is that many optimized leads still fail in preclinical and clinical testing, due to side effects or other reasons. In fact, the number of drugs that survive clinical trials and are ultimately approved is very low when compared to the projects that are initiated on validated target proteins near the beginning of the drug discovery process.

Rational drug design generally uses structural information about drug targets (structure-based) and/or their natural ligands (ligand-based) as a basis for the design of effective lead candidate generation and optimization. Structure-based rational drug design generally utilizes a three-dimensional model of the structure for the target. For target proteins or nucleic acids such structures may be as the result of X-ray crystallography/NMR or other measurement procedures or may result from homology modeling, analysis of protein motifs and conserved domains, and/or computational modeling of protein folding or the nucleic acid equivalent. Model-built structures are often all that is available when considering many membrane-associated target proteins, e.g., GPCRs and ion-channels. The structure of a ligand may be generated in a similar manner or may instead be constructed ab initio from a known 2-D chemical representation using fundamental physics and chemistry principles, provided the ligand is not a biopolymer.

Rational drug design may incorporate the use of any of a number of computational components ranging from computational modeling of target-ligand molecular interactions and combinations to lead optimization to computational prediction of desired drug-like biological and pharmacokinetic properties. The use of computational modeling in the context of rational drug design has been largely motivated by a desire to both reduce the required time and to improve the focus and efficiency of drug research and development, by avoiding often time consuming and costly efforts in biological "wet" lab testing and the like.

Computational modeling of target-ligand molecular combinations in the context of lead generation may involve the large-scale in-silico screening of molecule libraries (i.e., library screening), whether the libraries are virtually generated and stored as one or more structural databases or constructed via combinatorial chemistry and organic synthesis, using computational methods to rank a selected subset of ligands based on computational prediction of bioactivity (or an equivalent measure) with respect to the intended target molecule.

Throughout the text, the term "binding mode" refers to the 3-D molecular structure of a potential molecular complex in a bound state at or near a minimum of the binding energy (i.e., maximum of the binding affinity), where the term "binding energy" (sometimes interchanged with "binding free energy" or with its conceptually antipodal counterpart "binding affinity") refers to the change in free energy of a molecular system upon formation of a potential molecular complex, i.e., the transition from an unbound to a (potential) bound state for the ligand and target. The term "system pose" is also sometimes used to refer to the binding mode. Here the term free energy generally refers to both enthalpic and entropic effects as the result of physical interactions between the constituent atoms and bonds of the molecules between themselves (i.e., both intermolecular and intramolecular interactions) and with their surrounding environment, meaning the physical and chemical surroundings of the site of reaction between one or more molecules. Examples of the free energy are the Gibbs free energy encountered in the canonical or grand canonical ensembles of equilibrium statistical mechanics.

In general, the optimal binding free energy of a given target-ligand pair directly correlates to the likelihood of combination or formation of a potential molecular complex between the two molecules in chemical equilibrium, though, in truth, the binding free energy describes an ensemble of (putative) complex structures and not one single binding mode. However, in computational modeling it is usually assumed that the change in free energy is dominated by a single structure corresponding to a minimal energy. This is certainly true for tight binders (pK~0.1 to 10 nanomolar) but questionable for weak ones (pK~10 to 100 micromolar). The dominating structure is usually taken to be the binding mode. In some cases, it may be necessary to consider more than one alternative-binding mode when the associated system states are nearly degenerate in terms of energy.

Binding affinity is of direct interest to drug discovery and rational drug design because the interaction of two molecules, such as a protein that is part of a biological process or pathway and a drug candidate sought for targeting a modification of the biological process or pathway, often helps indicate how well the drug candidate will serve its purpose. Furthermore, where the binding mode is determinable, the action of the drug on the target can be better understood. Such understanding may be useful when, for example, it is desirable to further modify one or more characteristics of the ligand to improve its potency (with respect to the target), binding specificity (with respect to other target biopolymers), or other chemical and metabolic properties.

A number of laboratory methods exist for measuring or estimating affinity between a target molecule and a ligand. Often the target might be first isolated and then mixed with the ligand in vitro and the molecular interaction assessed experimentally such as in the myriad biochemical and functional assays associated with high throughput screening. However, such methods are most useful where the target is simple to isolate, the ligand is simple to manufacture and the molecular interaction easily measured, but is more problematic when the target cannot be easily isolated, isolation interferes with the biological process or disease pathway, the ligand is difficult to synthesize in sufficient quantity, or where the particular target or ligand is not well characterized ahead of time. In the latter case, many thousands or millions of experiments might be needed for all possible combinations of the target and ligands, making the use of laboratory methods unfeasible.

While a number of attempts have been made to resolve this bottleneck by first using specialized knowledge of various chemical and biological properties of the target (or even related targets such as protein family members) and/or one or more already known natural binders or substrates to the target, to reduce the number of combinations required for lab processing, this is still impractical and too expensive in most cases. Instead of actually combining molecules in a laboratory setting and measuring experimental results, another approach is to use computers to simulate or characterize molecular interactions between two or more molecules (i.e., molecular combinations modeled in silico). The use of computational methods to assess molecular combinations and interactions is usually associated with one or more stages of rational drug design, whether structure-based, ligand-based, or both.

When computationally modeling the nature and/or likelihood of a potential molecular combination for a given target-ligand pair, the actual computational prediction of binding mode and affinity is customarily accomplished in two parts: (a) "docking", in which the computational system attempts to predict the optimal binding mode for the ligand and the target and (b) "scoring", in which the computational system attempts to estimate the binding affinity associated with the computed binding mode. During library screening, scoring may also be used to predict a relative binding affinity for one ligand vs. another ligand with respect to the target molecule and thereby rank prioritize the ligands or assign a probability for binding.

Docking may involve a search or function optimization algorithm, whether deterministic or stochastic in nature, with the intent to find one or more system poses that have favorable affinity.

Scoring may involve a more refined estimation of an affinity function, where the affinity is represented in terms of a combination of one or more empirical, molecular-mechanics-based, quantum mechanics-based, or knowledge-based expressions, i.e., a scoring function. Individuals scoring functions may themselves be combined to form a more robust consensus-scoring scheme using a variety of formulations. In practice, there are many different docking strategies and scoring schemes employed in the context of today's computational drug design.

Another important area of application for computational docking and/or scoring, beyond the scope of virtual library screening, is in the process of in silico lead optimization, in which lead candidates are computationally examined with more scrutiny with respect to their binding affinity to the target. Most biomolecules are only relevant as potential drugs if they can outcompete other biomolecules that may interact with the target protein in the same or a nearby active site, including either the target's usual binding partner, or another a natural compound or antagonist, or even another drug. The results of high throughput screening usually only identify lead candidates with micromolar or worse binding affinities (i.e., IC50~1-100 micromolar). Lead optimization is involved with refining or modifying the lead candidate(s) in order to generate submicromolar and even nanomolar (i.e., IC50~ $10^{-9}$) drugs. Typical computational methods for estimating binding affinity of modified leads for the purpose of lead optimization include QSAR [53, 54], QM, MM, or QM/MM simulations [55], estimation of the change in free energy of the system using perturbation theory [56, 57], and other methods for structure-based molecular design [58].

However, even if a potential lead candidate binds well to one or more desired target biopolymers, i.e., demonstrates good bioactivity, the candidate molecule must ultimately meet further rigorous requirements regarding metabolism, toxicity, unwanted side effects, host distribution and delivery to the intended target site, inter and intra cellular transport, and excretion. In order to assess the viability of the lead candidate as a potential drug molecule and thereby possibly both shorten the timeline to market and reduce wasted R&D efforts, computational modeling has been employed to generate so-called ADME/Tox (Absorption Distribution Metabolism Excretion/Toxicology) profiles [59].

There are many measures involved in generating an ADME/Tox profile in silico. These include empirically guided predictions or estimations of bioaccumulation, bioavailability, metabolism, pKa, carcinogeneticity, mutagenicity, Log D, n-octanol/water partition coefficient or Log P, water solubility, permeability with the respect to blood brain barrier and other membranes, intestinal absorption, skin sensitivity, and even chemical and structural similarity to other known drugs or organic compounds. Some measures involve more precise numerical computation or prediction of physical or energetic properties of the biomolecule, such as pKa, Log D, Log P, etc. [60]. Other measures typically involve usage of knowledge or rule-based approaches, such as prediction of metabolic properties based on known biological pathways and transformations, qualitative estimation of distribution properties based on Lipinski's empirical "rule of five" [61], and prediction of toxicity using chemoinformatics knowledge databases to assess carcinogeneticity, mutagenicity, teratogeneticity, skin sensitivity, etc. Yet other measures are based on chemical and structural similarity to known biomolecules that are for example permeable with respect to the blood brain barrier or perhaps adversely affect the function of various organs, such as the liver or kidneys.

However, even with all of these computational tools in place, the failure rate due to safety and efficacy considerations in both preclinical testing and clinical trials featuring human (or other) subjects is still staggering in terms of both cost and lost market opportunity. A key reason for these failures is the existence of adverse cross-reactions between the lead candidate and other biomolecules (often other biopolymers) in the host organism, due to lack of specificity in binding to the desired target. These adverse cross-reactions can often lead to reduced efficacy of the drug candidate, to unwanted side effects, and even illness or death.

For example, the lead candidate while inhibiting the desired target protein may also unfortunately bind to one or more proteins or cell surface receptors in the liver, leading to a chemical imbalance or even a serious medical condition such as cirrhosis. In yet another example, the lead candidate may be misidentified by the host organism's immune system as a pathogen or other antigen leading to allergic reactions and other immune disorders. Ironically, even many of the commercial drugs that make it past clinical trials and approval often have various undesired side effects, such as insomnia, nausea, dehydration, erectile dysfunction, and drowsiness. Others such as cancer fighting drugs or strong antiviral agents have far more serious side effects which are only tolerated by the medical community since the underlying disease is otherwise lethal, e.g., chemotherapy drugs for various cancers, HIV cocktail drugs, etc.

Thus advanced knowledge of potential adverse cross reactions could not only reduce the time and cost involved in preclinical testing and clinical trials, but in also selecting drug candidates with less unwanted side effects and higher efficacy that would directly benefit the commercial viability of the drug.

As of Sep. 30, 2003, there are 20,501 protein structures, 948 protein/nucleic acid complexes, and 1233 nucleic acids (plus 18 carbohydrates) for a total 22,700 macromolecular structures in the Protein Data Bank (PDB) with an estimated doubling rate of approximately three years, as per the information published at the PDB web site at www.rcsb.org/pdb/ [62]. Approximately 83% are obtained via X-ray diffraction, 15% by NMR, and the remainder via other experimental methods. The nearly 20 K protein structures come from more than a 1000 individual species, with 4767 from *Homo sapiens*, 2411 from *E. Coli*, 1030 from mouse, etc. whereas roughly 1900 are synthetic and for an additional 4658 entries the species is not clearly identified; for a complete breakdown by species please see www.biochem.ucl.ac.uk/bsm/pdbsum/ species/. Further analysis and categorization of protein structure information available in the PDB may be found in [65] and [66]. The protein structures available in the PDB for nonhuman proteins often carry a wealth of information for purposes of drug design, especially considering that many proteins from other organisms such as mouse, pig, chicken, *C elegans*, yeast, etc. are homologous to human proteins in terms of both structure and function. Furthermore certain disease targets involve nonhuman proteins such as viral or bacterial proteins. New advances in structural proteomics and functional genomics continue to expand the number of available quality 3-D protein structures with functional annotation. Also further advancements in homology modeling, protein motifs, and protein threading continue to supplement the 3-D protein and nucleic acid structures obtained via experiment. Thus, the list of well-characterized potential cross-reactants for many drug candidates is already becoming substantial and will only continue to grow in the coming years.

Prior to this invention, there have been no systematic methods for precisely and effectively calculating the adverse reactions of lead molecules (i.e., potential drug candidates) on a computer based system.

Recently, a method named "inverse docking" has focused on the problem of much more limited scope, the identification of alternative targets for a single drug-like molecule and was described in Chen, Y. Z. and Zhi, D. G., "Ligand-Protein Inverse Docking and Its Potential Use in the Computer Search of Protein Targets of a Small Molecule", *Proteins* Vol. 43, 217-226 (2001) and further in Chen, Y. Z., Zhi, D. G., Ung, C. Y., "Computational Method for Drug Target Search and Application in Drug Discovery", Journal of Theoretical and Computational Chemistry, Vol. 1, No. 1, 213-224 (2002), (hereinafter, "Chen et al."); all of which is hereby incorporated by reference in their entirety. Even in this limited scope, these methods suffer from significant short comings as we will presently describe. The method of Chen et al. relies on a very specific geometric algorithm that essentially utilizes a mixture of the 'sphgen' algorithm generally associated with the UCSF software-docking tool DOCK [5, 6, 7] and a hybrid docking method described in Wang et al. [33] for evaluating the interactions between a known drug candidate and potential alternative targets. It has already been demonstrated in the art that such an approach will not be robust in predicting an accurate binding mode, let alone an accurate measure for binding energy, for most ligands.

Such a method relies on a simple molecular mechanics prediction of the binding energy, which is known in the art to predict the change in free energy with an error of ±3 kcal/mol for most systems [34-39]. Yet even a difference of two kcal/mol leads to a nearly 30-fold difference in the dissociation or inhibition constant of a molecular system. Thus, the method of Chen et al. cannot be expected to well estimate the absolute change in binding energy of the system. This is in fact supported by closer scrutiny of the authors' own published data. In Table 1 of Chen et al. (2002), four out of the nine systems (1hvr, 4phv, 1dhf, 3cpa) have publicly available experimental binding free energy values (respectively −13.13, −12.86, −3.08, and −5.39 kcal/mol as published at www-mitchell.ch.cam.ac.uk/pld/energy.php). Yet, this is in stark contrast to the reported predictions of respectively −70.2, −94.51, −48.67, and −40.63 kcal/mol. Moreover, the ligands in pdb entries 1hvr and 4phv are experimentally measured to have similar binding affinity for the same HIV-1 protease target protein, yet the corresponding predictions are off by more than 34%; a significant error.

Additionally, the method of Chen et al. relies on accurate prior characterization of the relevant active site of the potential target protein. While such prior information is often available for proteins in relation to their natural binders or agonists/antagonists, such is not often the case when exploring potential cross-reactions between various biopolymers and lead candidates designed for other, specific target proteins.

Furthermore, the method of Chen et al. utilizes an empirical threshold based on fitting a polynomial function of the number of ligand atoms to results generated by their docking protocol on a subset of pdb structures in order to remove certain false positive candidates. Yet, as anyone skilled in the art will recognize, no such empirical measure based on the number of ligand atoms correlates well with the observed experimental binding free energy data compiled to date.

Lastly, for the reasons listed above the method of Chen et al. requires the existence of at least one pdb entry featuring a complex of the potential with at least one other 'competing' ligand in order to better calibrate their prediction of binding affinity for the ligand in question further limiting its applicability. However, many pdb structures do not contain a relevant bound ligand and many other are bound to ligands at entirely different active sites than what may be relevant to the lead candidate. Moreover, in many systems, the target protein undergoes significant conformational changes when in transition from an unbound to bound state, i.e., an "induced fit". Thus lacking a mechanism for appropriate modeling of receptor flexibility, utilization of the bound conformational state will be inappropriate in many systems. Examples include carboxypeptidase-A-complexed various small peptides and calmodulin complexed with tamoxifen, both of which are included in the listed results of Chen et al. Together these factors might severely limit the scope of potential targets that can be screened by the method published in Chen et al.

Chen et al.'s method sacrifices both predictive accuracy and robustness in order to be able to rapidly process a given drug candidate against multiple potential protein targets, with the intent of 'fishing' for additional secondary therapeutic targets of the lead candidate. But the requirement of at least one competitive ligand in complex with the potential target in the relevant prior characterized active site makes the prospects very unattractive for identification of potential unwanted side effects and other adverse cross reactions against a large collection of alternative target biopolymers.

Moreover, as will be discussed in more detail later, prior art to date has not addressed three other very important issues regarding the prediction of adverse cross reactions and the application to improving the drug discovery process. The first being how to utilize the wealth of annotational information regarding function, source, homology to other structures, and family classification for macromolecular targets that exists in both the public and proprietary domains in order to make better judgments about potential adverse cross-reactions. The second being how to create an effective comparative evaluation of a collection of lead molecules based on their profiles of potential cross-reactions. The third being how to use the results of sophisticated computational modeling to infer how lead candidates that demonstrate one or more potential adverse cross-reactions due to lack of binding specificity can be reengineered or redesigned in order to increase binding discrimination between the desired therapeutic target and the potentially adverse cross-reactants, thereby making the biomolecule a viable drug candidate for clinical trials.

The importance of advance knowledge of potential cross-reactions in significantly improving the process of drug discovery has already been described above. Such knowledge will clearly help design better drugs with lower adverse side effects, at a reduced cost and with higher chances of success in clinical testing. The present invention will describe systems and methods that address this critical need.

REFERENCES & PRIOR ART

Prior art in the field of the current invention is heavily documented: the following tries to summarize it.

Drews [1] provides a good overview of the current state of drug discovery. In [2] Abagyan and Totrov show the state of high throughput docking and scoring and its applications. Lamb et al. [3] further teach a general approach to the design, docking, and virtual screening of multiple combinatorial libraries against a family of proteins. Finally Waskowycz et al. [4] describe the use of multiple computers to accelerate virtual screening of a large ligand library against a specific target by assigning groups of ligands to specific computers.

[1] J. Drews, "Drug Discovery: A Historical perspective," Science 287, 1960-1964 (2000).

[2] Ruben Abagyan and Maxim Totrov, "High-throughput docking for lead generation". Current Opinion in Chemical Biology 2001, 5:375-382.

[3] Lamb, M. L.; Burdick, K. W.; Toba, S.; Young, M. M.; Skillman, A. G. et al. "Design, docking, and evaluation of multiple libraries against multiple targets". Proteins 2001, 42, 296-318.

[4] Waszkowycz, B., Perkins, T. D. J., Sykes, R. A., Li, J. "Large-scale virtual screening for discovering leads in the post-genomic era", IBM Systems Journal, Vol. 40, No. 2 (2001).

There are a number of examples of software tools currently used to perform docking simulations. These methods involve a wide range of computational techniques, including use of a) rigid-body pattern-matching algorithms, either based on surface correlations, use of geometric hashing, pose clustering, or graph pattern-matching; b) fragmental-based methods, including incremental construction or 'place and join' operators; c) stochastic optimization methods including use of Monte Carlo, simulated annealing, or genetic (or memetic) algorithms; d) molecular dynamics simulations or e) hybrids strategies derived thereof.

The earliest docking software tool was a graph-based rigid-body pattern-matching algorithm called DOCK [5, 6, 7], developed at UCSF back in 1982 (v1.0) and now up to v5.0 (with extensions to include incremental construction). Other examples of graph-based pattern-matching algorithms include CLIX [8] (which in turn uses GRID [9]), FLOG [10] and LIGIN [11].

[5] Shoichet, B. K., Bodian, D. L. and Kuntz, I. D., "Molecular docking using shape descriptors", *J. Comp. Chem.*, Vol. 13 No. 3, 380-397 (1992).

[6] Meng, E. C., Gschwend, D. A., Blaney, J. M., and I. D. Kuntz, "Orientational sampling and rigid-body minimization in molecular docking", *Proteins: Structure, Function, and Genetics*, Vol. 17, 266-278 (1993).

[7] Ewing, T. J. A. and Kuntz, I. D., "Critical Evaluation of Search Algorithms for Automated Molecular Docking and Database Screening", *J. Computational Chemistry*, Vol. 18 No. 9, 1175-1189 (1997).

[8] Lawrence, M. C. and Davis, P. C.; "CLIX: A Search Algorithm for Finding Novel Ligands Capable of Binding Proteins of Known Three-Dimensional Structure", *Proteins*, Vol. 12, 31-41 (1992).

[9] Kastenholz, M. A., Pastor, M., Cruciani, G., Haaksma, E. E. J., Fox, T., "GRID/CPCA: A new computational tool to design selective ligands", *J. Medicinal Chemistry*, Vol. 43, 3033-3044 (2000).

[10] Miller, M. D., Kearsley, S. K., Underwood, D. J. and Sheridan, R. P., "FLOG: a system to select 'quasi-flexible' ligands complementary to a receptor of known three-dimensional structure", *J. Computer-Aided Molecular Design*, Vol. 8 No. 2, 153-174 (1994).

[11] Sobolev, V., Wade, R. C., Vriend, G. and Edelman, M., "Molecular docking using surface complementarity", *Proteins*, Vol. 25, 120-129 (1996).

Other rigid-body pattern-matching docking software tools include the shape-based correlation methods of FTDOCK [12] and HEX [13], the geometric hashing of Fischer et al. [14], or the pose clustering of Rarey et al. [15].

[12] Katchalski-Katzir, E., Shariv, I., Eisenstein, M., Friesem, A. A., Aflalo, C., and Vakser, I. A., "Molecular surface recognition: Determination of geometric fit between proteins and their ligands by correlation techniques", *Proceedings of the National Academy of Sciences of the United States of America*, Vol. 89 No. 6, 2195-2199 (1992).

[13] Ritchie, D. W. and Kemp. G. J. L., "Fast Computation, Rotation, and Comparison of Low Resolution Spherical Harmonic Molecular Surfaces", *J. Computational Chemistry*, Vol. No. 4, 383-395 (1999).

[14] Fischer, D., Norel, R., Wolfson, H. and Nussinov, R., "Surface motifs by a computer vision technique: searches, detection, and implications for protein-ligand recognition", *Proteins*, Vol. 16, 278-292 (1993).

[15] Rarey, M., Wefing, S., and Lengauer, T., "Placement of medium-sized molecular fragments into active sites of proteins", *J. Computer-Aided Molecular Design*, Vol. 10, 41-54 (1996).

In general, rigid-body pattern-matching algorithms assume that both the target and ligand are rigid (i.e., not flexible) and hence may be appropriate for docking small, rigid molecules (or molecular fragments) to a simple protein with a well-defined, nearly rigid active site. Thus, this class of docking tools may be suitable for de novo ligand design, combinatorial library design, or straightforward rigid-body screening of a molecule library containing multiple conformers per ligand.

Incremental construction based docking software tools include FlexX [16, 17] from Tripos (licensed from EMBL), Hammerhead [18], DOCK v4.0 [7] (as an option), and the nongreedy, backtracking algorithm of Leach et al. [19]. Programs using incremental construction in the context of de novo ligand design include LUDI [20] (from Accelrys) and GrowMol [21]. Docking software tools based on 'place and join' strategies include DesJarlais et al. [22].

[16] Kramer, B., Rarey, M. and Lengauer, T., "Evaluation of the FlexX incremental construction algorithm for protein-ligand docking", *Proteins*, Vol. 37, 228-241 (1999).

[17] Rarey, M., Kramer, B., Lengauer, T., and Klebe, G., "A Fast Flexible Docking Method Using An Incremental Construction Algorithm", *J. Mol. Biol.*, Vol. 261, 470-489 (1996).

[18] Welch, W., Ruppert, J. and Jain, A. N., "Hammerhead: Fast, fully automated docking of flexible ligands to protein binding sites", *Chemical Biology*, Vol. 3, 449-462 (1996).

[19] Leach, A. R., Kuntz, I. D., "Conformational Analysis of Flexible Ligands in Macromolecular Receptor Sites", *J. Comp. Chem.*, Vol. 13, 730-748 (1992).

[20] Bohm, H. J., "The computer program LUDI: a new method for the de novo design of enzyme inhibitors", *J. Computer-Aided Molecular Design*, Vol. 6, 61-78 (1992).

[21] Bohacek, R. S. and McMartin, C., "Multiple Highly Diverse Structures Complementary to Enzyme Binding Sites: Results of Extensive Application of a de Novo Design Method Incorporating Combinatorial Growth", *J. American Chemical Society*, Vol. 116, 5560-5571 (1994).

[22] DesJarlais, R. L., Sheridan, R. P., Dixon, J. S., Kuntz, I. D., and Venkataraghavan, R., "Docking Flexible Ligands to Macromolecular Receptors by Molecular Shape", *J. Med. Chem.*, Vol. 29, 2149-2153 (1986).

Incremental construction algorithms may be used to model docking of flexible ligands to a rigid target molecule with a well-characterized active site. They may be used when screening a library of flexible ligands against one or more targets. They are often comparatively less compute intensive, yet consequently less accurate, than many of their stochastic optimization based competitors. However, even FlexX may take on order of <1-2 minutes to process one target-ligand combination and thus may still be computationally onerous depending on the size of the library (e.g., tens of millions or more compounds). Incremental construction algorithms often employ one or more scoring functions to evaluate and rank different system poses encountered during computations. Recently FlexX was extended to FlexE [23] to attempt to account for partial flexibility of the target molecule's active site via use of user-defined ensembles of certain active site rotamers.

[23] Claussen, H., Buning, C., Rarey, M., and Lengauer, T., "FlexE: Efficient Molecular Docking Considering Protein Structure Variations", *J. Molecular Biology*, Vol. 308, 377-395 (2001).

Computational docking software tools based on stochastic optimization include ICM [24] (from MolSoft), GLIDE [25] (from Schrodinger), and LigandFit [26] (from Accelrys), all based on modified Monte Carlo techniques, and AutoDock v.2.5 [27] (from Scripps Institute) based on simulated annealing. Others based on genetic or memetic algorithms include GOLD [28, 29], DARWIN [30], and AutoDock v.3.0 [31] (also from Scripps).

[24] Abagyan, R. A., Totrov, M. M., and Kuznetsov, D. N., "Biased probability Monte Carlo conformational searches and electrostatic calculations for peptides and proteins", *J. Comp. Chem.*, Vol. 15, 488-506 (1994).

[25] Halgren, T. A., Murphy, R. B., Friesner, R. A., Beard, H. S., Frye, L. L., Pollard, W. T., and Banks, J. L., "Glide: a new approach for rapid, accurate docking and scoring. 2. Enrichment factors in database screening", *J Med Chem.*, Vol. 47 No. 7, 1750-1759, (2004).

[26] Luty, B. A., Wasserman, Z. R., Stouten, P. F. W., Hodge, C. N., Zacharias, M., and McCammon, J. A., "Molecular Mechanics/Grid Method for the Evaluation of Ligand-Receptor Interactions", *J. Comp. Chem.*, Vol. 16, 454-464 (1995).

[27] Goodsell, D. S. and Olson, A. J., "Automated Docking of Substrates to Proteins by Simulated Annealing", *Proteins: Structure, Function, and Genetics*, Vol. 8, 195-202 (1990).

[28] Jones, G., Willett, P. and Glen, R. C., "Molecular Recognition of Receptor Sites using a Genetic Algorithm with a Description of Desolvation", *J. Mol. Biol.*, Vol. 245, 43-53 (1995).

[29] Jones, G., Willett, P., Glen, R. C., Leach, A., and Taylor, R., "Development and Validation of a Genetic Algorithm for Flexible Docking", *J. Mol. Biol.*, Vol. 267, 727-748 (1997).

[30] Taylor, J. S. and Burnett, R. M., *Proteins*, Vol. 41, 173-191 (2000).

[31] Morris, G. M., Goodsell, D. S., Halliday, R. S., Huey, R., Hart, W. E., Belew, R. K. and Olson, A. J., "Automated Docking Using a Lamarckian Genetic Algorithm and an Empirical Binding Free Energy Function", *J. Comp. Chem.*, Vol. 19, 1639-1662 (1998).

Stochastic optimization-based methods may be used to model docking of flexible ligands to a target molecule. They generally use a molecular-mechanics-based formulation of the affinity function and employ various strategies to search for one or more favorable system energy minima. They are often more compute intensive, yet also more robust, than their incremental construction competitors. As they are stochastic in nature, different runs or simulations may often result in different predictions. Traditionally most docking software tools using stochastic optimization assume the target to be nearly rigid (i.e., hydrogen bond donor and acceptor groups in the active site may rotate), since otherwise the combinatorial complexity increases rapidly making the problem difficult to robustly solve in reasonable time.

Molecular dynamics simulations have also been used in the context of computational modeling of target-ligand combinations. This includes the implementations presented in Di Nola et al. [32] and Luty et al. [16] (along with Monte Carlo). In principle, molecular dynamics simulations may be able to model protein flexibility to an arbitrary degree. On the other hand, they may also require evaluation of many fine-grained, time steps and are thus often very time-consuming (one order of hours or even days per target-ligand combination). They also often require user interaction for selection of valid trajectories. Use of molecular dynamics simulations in lead discovery is therefore more suited to local minimization of predicted complexes featuring a small number of promising lead candidates.

[32] Di Nola, A., Berendsen, H. J. C., and Roccatano, D., "Molecular Dynamics Simulation of the Docking of Substrates to Proteins", *Proteins*, Vol. 19, 174-182 (1994).

Hybrid methods may involve use of rigid-body pattern matching techniques for fast screening of selected low-energy ligand conformations, followed by Monte Carlo torsional optimization of surviving poses, and finally even molecular dynamics refinement of a few choice ligand structures in combination with a (potentially) flexible protein active site. An example of this type of docking software strategy is Wang et al. [33].

[33] Wang, J., Kollman, P. A. and Kuntz, I. D., *Proteins*, Vol. 36, 1-19 (1999).

There are a number of examples of scoring functions implemented in software and used to estimate target-ligand affinity, rank prioritize different ligands as per a library screen, or rank intermediate docking poses in order to predict binding modes. Scoring functions traditionally fall into three distinct categories: a) empirical scoring functions, b) molecular-mechanics-based expressions, or (c) knowledge-based scoring functions or hybrid schemes derived thereof.

Empirically derived scoring functions (as applied to target-ligand combinations) were first inspired by the linear free-energy relationships often utilized in QSAR studies. An early example is that of Bohm et al. [20, 34] (used in LUDI). Other empirical scoring functions include SCORE [35] (used in FlexX), ChemScore [36], PLP [37], Fresno [38], and GlideScore v.2.0+ [39] (modified form of ChemScore, used by GLIDE).

[34] Böhm, H. J., "The Development of a simple empirical scoring function to estimate the binding constant for a protein-ligand complex of known three-dimensional structure", *J. Comput-Aided Mol. Des.*, Vol. 8, 243-256 (1994).

[35] Wang, R., Gao, Y. and Lai, L., "A new empirical method for estimating the binding affinity of a protein-ligand complex.", *J. Molecular Modeling*, Vol. 4, 379 (1998).

[36] Eldridge, M. D., Murray, C. W., Auton, T. R., Paolini, G. V., and Mee, R. P., "Empirical scoring functions: I. The development of a fast empirical scoring function to estimate the binding affinity of ligands in receptor complexes", *J. Computer-Aided Molecular Design*, Vol. 11, 425-445 (1997).

[37] Gelhaar, D. K., Bouzida, D.; Rejto, P. A., In *"Rational Drug Design: Novel Methodology and Practical Applications"*, Parrill, L., Reddy, M. R., Ed.; American Chemical Society: Washington, D.C., pp. 292-311 (1999).

[38] Rognan D., Lauemoller S. L., Holm A., Buus S., Schinke V., *J. Medicinal Chemistry*, Vol. 42, 4650-4658 (1999).

[39] Halgren, T. A., Murphy, R. B., Friesner, R. A., Beard, H. S., Frye, L. L., Pollard, W. T., and Banks, J. L., "Glide: a new approach for rapid, accurate docking and scoring. 2.

Enrichment factors in database screening", *J Med Chem.*, Vol. 47 No. 7, 1750-1759, (2004).

In general, empirical scoring functions comprise the bulk of scoring functions used today, especially in the context of large compound library screening. The basic premise is to calibrate a linear combination of empirical energy models, each multiplied by an associated numerical weight and each representing one of a set of interaction components represented in a (so-called) 'master scoring equation', where said equation attempts to well approximate the binding free energy of a molecular combination. The numerical weight factors may be obtained by fitting to experimental binding free energy data composed for a training set of target-ligand complexes.

Molecular-mechanics-based scoring functions were first developed for use in molecular modeling in the context of molecular mechanics force fields like AMBER [40, 41], OPLS [42], MMFF [43], and CHARMM [44]. Examples of molecular-mechanics-based scoring functions include both the chemical and energy-based scoring functions of DOCK v.4.0 (based on AMBER) [7], the objective functions used in GOLD [28, 29], AutoDock v.3.0 [31] (with empirical weights), and FLOG [10].

[40] Pearlman, D. A., Case, D. A., Caldwell, J. C., Ross, W. S., Cheatham III, T. E., Ferguson, D. M., Seibel, G. L., Singh, U. C., Weiner, P., Kollman, P. A. *AMBER* 4.1, University of California, San Francisco (1995).

[41] Cornell, W. D., Cieplak, P., Bayly, C. I., Goulg, I. R., Merz, K. M., Ferguson, D. M., Spellmeyer, D. C., Fox, T., Caldwell, J. W., Kollman, P. A., "A second-generation force field for the simulation of proteins, nucleic acids, and organic molecules", *J. American Chemical Society*, Vol. 117, 5179-5197 (1995).

[42] Jorgensen, W. L., & Tirado-Rives, J., *J. American Chemical Society*, Vol. 110, 1657-1666 (1988).

[43] Halgren, T. A., "Merck Molecular Force Field. I. Basis, Form, Scope, Parameterization, and Performance of MMFF94", *J. Comp. Chem.*, Vol. 17, 490-519 (1996).

[44] Brooks, B. R., Bruccoleri, R. E., Olafson, B. D., States, D. J., Swaminathan, S, and Karplus, M., "CHARMM: A Program for Macromolecular Energy, Minimization, and Dynamics Calculations", J. Comp. Chem., Vol. 4, 187-217 (1983).

In general, molecular-mechanics-based scoring functions may closely resemble the objective functions utilized by many stochastic optimization-based docking programs. Such functions typically require atomic (or chemical group) level parameterization of various attributes (e.g., charge, mass, vdW radii, bond equilibrium constants, etc.) based on one or more molecular mechanics force fields (e.g., AMBER, MMFF, OPLS, etc.). In some cases, the relevant parameters for the ligand may also be assigned based on usage of other molecular modeling software packages, e.g., ligand partial charges assigned via use of MOPAC [45], AMPAC [46] or AMSOL [47]. They may also include intramolecular interactions (i.e., self-energy of molecules), as well as long range interactions such as electrostatics. In some cases, the combination of energy terms may again be accomplished via numerical weights optimized for reproduction of test ligand-target complexes.

[45] Stewart, J. J. P., *Quantum Chemistry Program Exchange*, Vol. 10:86 (1990).

[46] Liotard, D. A., Healy, E. F., Ruiz, J. M., and Dewar, M. J. S., *Quantum Chemistry Program Exchange*—no. 506, QCPE Bulletin, Vol. 9: 123 (1989).

[47] AMSOL-version 6.5.1 by G. D. Hawkins, D. J. Giesen, G. C. Lynch, C. C. Chambers, I. Rossi, J. W. Storer, J. Li, D. Rinaldi, D. A. Liotard, C. J. Cramer, and D. G. Truhlar, University of Minnesota, Minneapolis (1997)

Knowledge-based scoring functions were first inspired by the potential of mean force statistical mechanics methods for modeling liquids. Examples include DrugScore [48], PMF [49], and BLEEP [50].

[48] Gohlke, H., Hendlich, M. and Klebe, G., "Knowledge-based Scoring Function to Predict Protein-Ligand Interactions", *J. Mol. Biol.*, Vol. 295, 337-356 (2000)

[49] Muegge, I. and Martin, Y. C., "A general and fast scoring function for protein-ligand interactions—a simplified potential approach", *J. Med. Chem.*, Vol. 42, 791-804 (1999).

[50] Mitchell, J. B. O., Laskowski, R. A., Alex, A. and Thornton, J. M., "BLEEP—Potential of Mean Force Describing Protein-Ligand Interactions II. Calculation of Binding Energies and Comparison with Experimental Data", *J. Comp. Chem.*, Vol. 20, 1165-1176 (1999)

In general, knowledge-based scoring functions do not require partitioning of the affinity function. However, they do require usage of a large database of 3-D structures of relevant molecular complexes. There is also usually no need for regression against a data set of molecular complexes with known experimental binding affinities. These methods are based on the underlying assumption that the more favorable an interaction is between two atoms, at a given distance, the more frequent its occurrence relative to expectations in a bulk, disordered medium. These schemes are sometimes referred to as 'inverse Boltzmann' schemes, but in fact the presence of local, optimized structures in macromolecules and protein folds means that distance-dependent pair-wise preference distributions need not be strictly Boltzmann. It is also possible to introduce the concept of singlet preferences based on other molecular descriptors, e.g., solvent accessible surface area for approximation of solvation effects.

Hybrid scoring functions may be a mixture of one or more scoring functions of distinct type. One example is VALIDATE [51], which is a molecular-mechanics/empirical hybrid function. Other combinations of scoring functions may include the concept of consensus scoring in which multiple functions may be evaluated for each molecular combination and some form of 'consensus' decision is made based on a set of rules or statistical criteria, e.g., states that occur in the top 10% rank list of each scoring function (intersection-based), states that have a high mean rank (average-based), etc. A useful review discussion of consensus scoring can be found in Bissantz et al. [52].

[51] Head, R. D., Smythe, M. L., Oprea, T. I., Waller, C. L., Green, S. M. and Marshall, G. R., "VALIDATE: A New Method for Receptor-Based Prediction of Binding Affinities of Novel Ligand", *J. American Chemical Society*, Vol. 118, 3959-3969 (1996)

[52] Bissantz, C., Folkers, G., Rognan, D., "Protein-based virtual screening of chemical databases. 1. Evaluation of different docking/scoring combinations", *J Med Chem*, Vol. 43, 4759-4767 (2000)

Other computational methods used especially during lead optimization due to computing resource constraints include QSAR (Quantitative Structure Activity Relationships), QM/MM simulations, and free energy perturbation theory, of which the latter two are more appropriate for higher accuracy prediction of binding affinities for various complexes, provided the binding modes have already been satisfactorily determined. These and other methods relevant to lead optimization in the context of structure-based design include those reviewed in Bohacek et al. [58].

[53] "3D QSAR in Drug Design: Recent Advances" (Vols. 1-3) by Hugo Kubinyi (Editor), Gerd Folkers (Editor), and Yvonne C. Martin (Editor)

[54] Exploring QSAR: Hydrophobic, Electronic, and Steric Constants (ACS Professional Reference Book) by Corwin Hansch (Editor), Albert Leo (Editor), D. H. Hoekman (Editor)

[55] Murphy, R. B., Philipp, D. M., Friesner, R. A., "Frozen Orbital QM/MM methods for density functional theory", *Chem. Phys. Letters*, Vol. 321, 113-120 (2000).

[56] Aqvist, J., Medina, C., and Samuelsson, J. E., "A new method for predicting binding affinity in computer-aided drug design", *Prot Eng*, Vol. 7, 385 (1994)

[57] Jones-Hertzog, D. K., and Jorgensen, W. L., "Binding Affinities for Sulfonamide Inhibitors with Human Thrombin Using Monte Carlo Simulations with a Linear Response Method", *J Med Chem*, Vol. 40, 1539 (1997)

[58] Bohacek, R. S., McmArtin, C., Guida, W. C., "The Art and Practice of Structure-Based Drug Design: A Molecular Modeling Perspective", *Medicinal Research Reviews*, Vol. 16, 3 (1996)

Lead optimization often includes assessment of various pharmacokinetic properties for lead candidates whether via wet lab and/or computational means. This includes ADME/Tox profiles, comprising various measures such as Log D, Log P, etc., as well as the empirically based Lipinski "rules of five".

[59] Ekins, S., and Rose, J., "In silico ADME/Tox: the state of the art", *J Mol Graph Model*, Vol. 20, No. 4, 305-309 (2002)

[60] Ghose, A. K.; Viswanadhan, V. N.; Wendoloski, J. J., "Prediction of hydrophobic (lipophilic) properties of small organic molecules using fragmental methods: An analysis of ALOGP and CLOGP methods", *J. Phys. Chem.*, Vol. 102, 3762-3772 (1998)

[61] Lipinski, C. A., Lombardo, F., Dominy, B. W., Feeney, P. J., "Experimental and computational approaches to estimate solubility and permeability in drug discovery and development settings", *Advanced Drug Delivery Reviews*, 1997, Vol. 23, 3-25 (1997)

Many experimentally obtained structures exist for proteins complexed with various compounds exist in publicly accessible databases such as the Protein Data Bank (PDB). Public database also exist for protein and nucleic acid sequences such as GenBank and SwissProt. Multiple analyses of such databases have been used to estimate various properties of the data including redundancy, sequence similarity, number of expressed genes, etc.

[62] Berman, H. M., Westbrook, J., Feng, Z., Gilliland, G., Bhat, T. N., Weissig, H., Shindyalov, I. N., Bourne. P. E., "The Protein Data Bank", *Nucleic Acids Research*, Vol. 28, 235-242 (2000)

[63] www.ncbi.nlm.nih.gov/GenBank/

[64] Bairoch, A. and Boeckman, B., "The SWISS-PROT protein sequence data bank, recent developments", Nucleic Acids Res, Vol. 21, 3093-3096 (2003)

[65] Rost, B. and Sander, C., "Bridging the protein sequence structure gap by structure predictions", *Annual Review Biophys Biomol Struct*, Vol. 25, 113-136 (1996)

[66] Wang, G. and Dunbrack, R. L., "PISCES: a protein culling server", *Bioinformatics*, submitted (2002)

[67] A. L. Hopkins & C. R. Groom, "The Druggable Genome", *Nature Reviews Drug Discovery*, 1, 727-730 (2002).

[68] Murphy, R. B., Philipp, D. M., Friesner, R. A., "Frozen Orbital QM/MM methods for density functional theory", *Chem. Phys. Letters*, Vol. 321, 113-120 (2000).

Various file formats exist for the digital representation of structural and chemical information for both target proteins and compounds as related to structural databases. Examples include the pdb, mol2 (from Tripos), and the SMILES formats.

[69] Westbrook, J. and Fitzgerald, P. M. (2003): *Structural Bioinformatics*, P. E. Bourne and H. Weissig (editors). Hoboken, N.J., John Wiley & Sons, Inc. pp. 161-179.

[70] www.tripos.com/custResources/mol2Files/

[71] www.daylight.com/dayhtml/smiles/smiles-intro.html

[72] Clark, M., Cramer, R. D., Opdenbosch, N. V., "Validation of the General Purpose Tripos 5.2 Force Field", *J. Comp. Chem.*, Vol. 10, 982-1012 (1989).

[73] Stouten, P. F. W., Frommel, C., Nakamura, H., and Sander, C., "An effective solvation term based on atomic occupancies for use in protein simulations", *Molecular Simulation*, Vol. 10, No. 2-6, 97-120 (1993).

[74] www2.chemie.uni-erlangen.de/software/corina/index.html

[75] Takahashi, Y., Satoh, Y., and Sasaki, S., "Recognition of largest common structural fragment among a variety of chemical structures", *Analytical Sciences*, Vol. 3, pp. 23-28 (1987).

[76] McGregor, M. J., Pallai, P. V., "Clustering of large databases of compounds using MDL Keys as structural descriptors", *J. Chem. Inf. Comput. Science*, Vol. 37, p. 443-(1997).

BRIEF SUMMARY OF THE INVENTION

Aspects of the invention relate to a method for the prediction of adverse cross-reactions between lead candidate biomolecules and potential reactant molecules, often biopolymers, in order to better characterize lead candidates in terms of safety and efficacy as pertains to a target disease or biological condition and also to facilitate further optimization of the lead candidate molecule in order to improve binding specificity to the desired target and to avoid adverse and/or otherwise unanticipated cross reactions with other unrelated biomolecules.

In a computational system, reactions are modeled within a suitable environment, in order to determine a reaction profile between a lead candidate molecule and a potential reactant molecule, the method comprising obtaining a reaction measure for reactions between the lead molecule and the potential reactant molecule, obtaining other variables such as relevant source, functional, and homolog annotation, model predictions, and experimental results (if applicable) for the lead and potential reactant molecule, combining the reaction measure and other relevant annotations and variables in order to construct the reaction profile, which reflects both the likelihood of combination between the lead candidate and potential reactant molecule and the likelihood that a predicted cross-reaction is undesirable or even harmful. The process can be repeated for the same lead candidate molecule against multiple potential reactant molecules from a molecular library or database and a summary cross reaction profile generated for the lead candidate in order to better characterize the lead in terms of safety and efficacy.

Further aspects of the invention, include a method for redesign and optimization of the lead candidate, possibly iterative in nature, in order to avoid predicted adverse cross-reactions. The method comprises identification of a common molecular core or scaffold that is required in binding the lead candidate to the desired target molecule followed by identification of various molecular components of the lead candidate molecule that may be added, removed, or substituted in order to degrade binding affinity and/or disrupt certain intermolecular hydrogen bonds with the potential adverse cross-reactant molecule without significantly degrading binding affinity of the lead to the desired target molecule via examination of the relevant predicted binding modes and reaction measure(s). A new iteration of the optimization cycle may then be run by generating a new summary reaction profile for the newly generated structural variations of the lead candidate against the multiple potential reactant molecules from a molecular library or database until one or more of the structural variants of the lead candidate is deemed to have a sufficiently low probability of an adverse cross-reaction.

BRIEF DESCRIPTION OF THE DRAWINGS

FIG. 1 is a diagram illustrating a protein (dihydrofolate reductase) shown as an example target biopolymer used in the description of various embodiments of the present invention. The data represented in FIG. 1 includes the primary amino acid sequence (FIG. 1A), a secondary structure representation (FIG. 1B), a solvent accessible surface rendering of the protein surface (FIG. 1C), and a pdb file representation of X-ray crystallographic structural data for pdb entry 4dfr featuring dihydrofolate reductase;

FIG. 2 is a diagram illustrating a molecule (methotrexate) shown as an example lead candidate used in the description of various embodiments of the present invention. The data represented in FIG. 2 includes the chemical formula and a stereo SMILE (FIG. 2A), a 2-D structure representation (FIG. 2B), a 3-D 'ball-and-stick' representation of a conformation of methotrexate (FIG. 2C), and a Tripos mol2 file representation of structural data for the same conformation of methotrexate (FIG. 2D);

FIG. 3 is a diagram illustrating a molecular complex featuring methotrexate bound to dihydrofolate reductase shown as an example complexed structure used in the description of various embodiments of the present invention. The data represented in FIG. 3 includes a solvent accessible surface representation of the active site (FIG. 3A), a 3-D representation of the complex showing methotrexate bound in the active site (FIG. 3B), a 2-D graphical representation (FIG. 3C) of interacting groups on both the ligand (methotrexate) and the target (dihydrofolate reductase), and a table of four groups of active site residues of the target protein (FIG. 3D);

FIGS. 4A-4C is a diagram illustrating an example of how a target and/or potential reactant record might be structured for use in some embodiments of the present invention;

FIGS. 5A-5C is a diagram illustrating an example of how a lead candidate record might be structured for use in some embodiments of the present invention;

FIG. 6 is a block diagram of a computational modeling system that may be used to determine potential cross-reactions between various potential reactants and lead candidates, as well as to redesign and optimize lead candidates for improved binding specificity to one or more desired targets, according to embodiments of the present invention;

FIG. 7 is a diagram illustrating a molecular complex featuring methotrexate bound to *E. Coli* thymidylate synthase shown as another example complexed structure used in the description of various embodiments of the present invention. The data represented in FIGS. 7A-7C correspond to that shown in FIGS. 3A-3C for methotrexate complexed with dihydrofolate reductase;

FIG. 8 is a diagram illustrating a molecular complex featuring folinic acid bound to rabbit cytosolic serine hydroxymethyl transferase shown as another example complexed structure used in the description of various embodiments of the present invention. The data represented in FIGS. 8A-8C correspond to that shown in FIGS. 3A-3C for methotrexate complexed with dihydrofolate reductase;

FIGS. 9A-9B is a diagram illustrating a 2-D representation of scaffold molecular structure for methotrexate with annotated structural linkage sites and a table of chemical groups that may be substituted into or added to the existing scaffold as part of one embodiment of the invention involving a drug redesign optimization process as applied to methotrexate;

FIGS. 10A-10B is a diagram illustrating various different examples structures generated as part of one embodiment of the invention involving a drug redesign optimization process as applied to methotrexate.

DETAILED DESCRIPTION OF THE INVENTION

The present invention has many applications, as will be apparent after reading this disclosure. In describing an embodiment of a computational system according to the present invention, only a few of the possible variations are described. Other applications and variations will be apparent to one of ordinary skill in the art, so the invention should not be construed as narrowly as the examples, but rather in accordance with the appended claims.

Embodiments of the invention will now be described, by way of example, not limitation. It is to be understood that the invention is of broad utility and may be used in many different contexts.

The present invention relates to estimation of cross reactivity of one or more lead candidates, possibly associated with one or more desired targets, versus a set of potential reactants to assess one or more aspects of usefulness of the lead candidates.

For purposes of the invention, a target is a biomolecule, part of a biomolecule, compound of one or more biomolecules or other bioreactive agent, often a biopolymer, for which there is a desire to modify its actions in its environment. For example, biopolymers, including proteins, polypeptides, and nucleic acids, are example targets. Modification of actions of the target might include deactivating actions of the target (inhibition), enhancing the actions of the target or otherwise modifying its action before or during other interactions (catalysis). In one embodiment, the target might be a protein that is produced or introduced into the human body and causes disease or other ill effect and the desired modification is to inhibit the action of the protein by competitively binding a small biomolecule to the relevant active site of the protein. In another embodiment, the target protein itself is not a direct initiator of the undesired disease or ill effect, but by affecting its function may better regulate reactions involving some other protein (e.g., enzyme, antibody, etc.) or biomolecule and thereby alleviate the condition warranting treatment.

In yet another embodiment, the lead candidates may dock to a cell surface receptor thereby preventing a pathogen biopolymer such as a viral protein from attaching to a cell and thereby prevent illness. In yet another example, the lead candidate may promote chemical modification of the target protein (e.g., phosphorylation, cleavage of disulfide bonds, disruption of metal ion coordination, etc.), or in the case of gene therapy, actual substitution of one or more base pairs in DNA. In yet another example, the desired modification might be to modify the target for easier identification and/or better characterization of the functional pathway featuring the target. For example, a target might be modified by the lead candidate to carry a molecular tag to make it easier to detect where the target is and how it interacts with its environment.

FIGS. 1A-1D depict an example protein. This protein has a crystal structure denoted by pdb entry 4dfr. The protein dihydrofolate reductase, a target involved in the regeneration of tetrahydrofolate as part of deoxythymidylate production cycle important to DNA synthesis. Item 110 of FIG. 1A shows the primary amino acid sequence for the protein using three letter codes for each amino acid. Picture 120 of FIG. 1B shows a graphical representation of the secondary structure of the 4dfr protein molecule along with a collection of tables 125 indicating locations of various secondary structural components such as beta sheets, alpha helices, hairpins, etc. Picture 130 of FIG. 1C shows a representation of the solvent accessible surface of the dihydrofolate reductase protein using a 1.4 Å radius probe sphere and for which the different colors indicate different surface atoms (e.g., item 131=white=hydrogen, item 132=black=carbon, item 133=dark gray=oxygen, etc.).

FIG. 1D shows a pdb file representation 150 of a chemical structure for an input structural conformation of the dihydrofolate reductase protein obtained from the Protein Data Bank [62, 69] based on X-ray crystallography. In FIG. 1D, the pdb file representation 150 includes a general header section 142, a section 144 composed of atom type and coordinate information, and a section 146 regarding bond connectivity information. The header section 142 may contain any annotation or other information desired regarding the identity, source, structural components, sequence data, or other characteristics of the target biomolecule. Section 144 by virtue of an ellipsis, shows a list of 1,280 non-hydrogen atoms of one chain of dihydrofolate reductase and for each atom it includes a chemical type (e.g., atomic element) and three spatial coordinates. For instance, the line for atom 9 shows that it is a nitrogen atom with name N in an ILE residue in chain A with residue ID 2 and with (x, y, z) coordinates (23.920, 57.222, 6.665) in a specified Cartesian coordinate system. Note that section 144 may also include entries for various heteroatoms such as metal ions, structural waters, or other additional atoms or molecules associated with the target. In section 144, the lines denoted by item 148 show an example of several line entries for oxygens corresponding to structural waters and even a chlorine atom.

Section 146 of the PDB file 150 shows a subset of the so-called 'connect record' of a PDB file, where each line entry describes a list of the bonds associated with each atom. For instance, the first line of this section shows that atom 1 is bonded to atom 2, whereas the second line shows that atom 2 is bonded to atoms 1, 3, and 5. Notice also how in this example hydrogens are missing and as such the bond connections for each atom may not be complete. Of course, completed variants of the PDB file representation are possible if the positions of hydrogen atoms are already specified, but in many cases where the chemical structure originates from experimental observations such as X-ray crystallography the positions of hydrogens may be very uncertain or missing altogether. However, standard computational tools exist that can predict the positions of the hydrogen atoms and properly hydrogenate the protein based on assumption of physiological pH.

Other example file formats include the MDL format, Tripos' mol2 format [70], the SMILES convention, etc. [71]. The chemical and structural information for the target may also be stored in a variety of 3-D biomolecular structural databases featuring various schema and entity-relationships.

A lead candidate is a biomolecule, part of a biomolecule, compound of one or more biomolecules or other bioreactive agent that has been selected based on prior assessment of relevant bioactivity with the target. Usually the purpose of prior assessment is to determine whether the lead candidate when in the appropriate environment will react with the target to cause a desired modification of the actions of the target. The assessment of bioactivity may involve myriad biochemical assays, wet lab experiments, various measurement processes, computational prediction of binding affinity, high throughput screening, virtual library screening, ADME/Tox profiles, QSAR, molecular modeling, etc. Examples of lead candidates include small molecule ligands, peptides, proteins, parts of proteins, synthetic compounds, natural compounds, organic molecules, carbohydrates, residues, inorganic molecules, ions, individual atoms, radicals, and other chemically active items. Lead candidates can form the basis of drugs or compounds that are administered or used to create desired modifications or used to examine or test for undesirable modifications. The terms "lead" and "drug candidate" are used interchangeably with the term "lead candidate".

FIGS. 2A-2D depict the compound methotrexate; a known nanomolar binder to the dihydrofolate reductase depicted in FIGS. 1A-1D. Methrotrexate is used in chemotherapy as a cancer-fighting drug for treatment of multiple types of human carcinomas by inhibiting the protein dihydrofolate reductase; thereby indirectly blocking the production of deoxythymidylate and stalling fundamental cellular processes involved with DNA synthesis in order to slow down the growth of malignant tumor cells. Item 210 in FIG. 2A shows the chemical formula for methotrexate. Item 215 in FIG. 2A shows a stereo SMILE [71] for methotrexate. Picture 220 in FIG. 2B shows a 2-D structural representation of the methotrexate molecule including non-hydrogen atoms only.

Item 230 in FIG. 2C shows a 'ball-and-stick' rendering of a conformation 230 of a methotrexate molecule according to the chemical formula $C_{20}H_{22}N_8O_5$ listed in item 210 of FIG. 2A. The molecule consists of a collection of atoms 240 and bonds 260. The small, black atoms, as indicated by item 243, represent carbon atoms. The tiny, white atoms, as indicated by item 245, represent hydrogen atoms, whereas the slightly larger dark atoms (item 247) are oxygen atoms and the larger white atoms (item 249) are nitrogen atoms.

Continuing in FIG. 2c, item 253 denotes a circle containing a benzene ring ($C_6H_4$), and item 255 a circle containing a carboxyl group (COO), and item 257 another circle containing a methyl group ($CH_3$). Item 263 denotes a covalent bond connecting the benzene ring 253 to the ester group that includes the methyl group 257. Item 265 denotes a covalent bond connecting the carbon atom 243 to the carboxyl group 255. Lastly, item 267 denotes a covalent bond connecting the methyl group 257 to a nitrogen atom 249.

FIG. 2D shows a Tripos mol2 file containing various structural and chemical information for the input conformation for methotrexate depicted in FIG. 2C. Column 270 lists an index for each atom; column 273 lists an atom name (may be nonunique) for each atom; columns 275, 277, and 279 respectively list x, y, z coordinates for each atom in an internal coordinate system; column 280 lists a SYBYL atom type according to the Tripos force field [72] for each atom that codifies information for hybridization states, chemical type, bond connectivity, hydrogen bond capacity, aromaticity, and in some cases chemical group; and columns 282 and 285 list a residue ID and a residue name for each atom (relevant for proteins, nucleic acids, etc.). Section 290 lists all bonds in the molecular subset. Column 291 lists a bond index for each bond; columns 292 and 293 the atom indices of the two atoms connected by the bond; and column 295 the bond type, which may be single, double, triple, delocalized, amide, aromatic, or other specialized covalent bonds. In other embodiments, such information may also represent noncovalent bonds such as salt bridges or hydrogen bonds. In this example, notice how the hydrogen atoms have now been included.

The loci of interaction on or near the surface of the target where the lead candidate binds or comes into stable contact with the target is usually referred to as the active site. It is also referred to as a binding pocket, binding site, or a binding cavity.

FIGS. 3A-3D relate to a molecular complex formed by the dihydrofolate reductase protein of FIGS. 1A-1D and the methotrexate molecule of FIGS. 2A-2D. FIG. 3A depicts an active site of dihydrofolate reductase as relevant to reacting with methotrexate. In FIG. 3A, the active site is shown as a portion of the solvent accessible surface shaded in dark gray (item 310) embedded in the overall solvent accessible surface of the protein in light gray (item 320). FIG. 3B depicts the molecular complex comprising the target protein (dihydrofolate reductase) represented by a bimodal solvent accessible surface (dark gray portion is active site 310 and light gray portion 320 is remainder of protein) bound to the lead candidate (methotrexate) represented by a collection of white sphere 325. As evident in FIG. 3B, the methotrexate molecule fits tightly into the active site shown in FIG. 3A.

FIG. 3C shows a 2-D graphical representation of the interaction between various chemical groups on methotrexate and various residues of dihydrofolate reductase. Item 340 denotes a 2-D representation of the methotrexate molecule (MTX) in the active site of dihydrofolate reductase for the first chain of pdb entry 4dfr. Items 331, 333, 334, 335, 336, 337, and 339 represent protein residues involved in hydrophobic contacts with various groups of methotrexate. Items 350, 352, 354, 356, and 358 respectively represent catalytic residues Asp27, Ile5, Ile94, Arg52, and Arg 57 of dihydrofolate reductase in the active site, each of which are involved in forming one or more intermolecular hydrogen with the methotrexate. The hydrogen bonds themselves are depicted via dashed lines between matched hydrogen bond donor and acceptor groups.

FIG. 3D shows a text representation of a collection of active residues of the dihydrofolate reductase protein that interact with the methotrexate molecule. Here there are four active site residue groupings depicted as items 371 (APT), 372 (ANM), 373 (AAB), and 374 (AGL). Item 375 represents a summary description for grouping APT, whereas item 377 list the individual residues that are include in grouping APT. Similar information is available for groupings ANM, AAB, and AGL.

Information about the molecular complex depicted in FIGS. 3A-3D may be represented digitally via various means including, but not limited to, the aforementioned pdb and mol2 file formats illustrated by example in FIGS. 1D and 2D.

A potential reactant is a biomolecule, part of a biomolecule, composite of one or more biomolecules or other bioreactive agent that might also react with a lead whether or not this would occur in an environment similar to that within which the lead is expected to react with the target. The modifications due to a lead of action of one or more potential reactants that share a host organism with the target are referred to herein as "cross reactions".

Cross-reaction of the lead candidate with such a potential reactant may lead to an unexpected, and often undesirable, modification of the action of the potential reactant. However, since the potential reactant may often represent a biopolymer that has no direct relevance to the disease at hand and may otherwise perform normal or even vital functions for the host organism, such a cross-reaction may lead to undesirable side effects. For example, methotrexate while a strong inhibitor of dihydrofolate reductase is known to cause toxic side effects that affect the actions of multiple proteins in the lungs, kidney, and nervous system. In yet another example, many compounds are known to interact undesirably with proteins in the liver thereby inducing liver damage and even serious medical conditions such as cirrhosis.

Potential reactants may come from a variety of organisms including humans, mammals, insects, plants, bacteria, etc. They may also come from a variety of different species, organs, tissues, cell types, etc. Their structural information may be obtained either via a variety of experimental means and measurement processes or by computational modeling and structural prediction.

A set of potential reactants might be known and/or obtained from a variety of sources, whether experimental, computational or biological in nature. These may include one or more public or proprietary proteomics or genomics databases, such as PDB [62], GenBank [63], SwissProt [64], etc., for which different query selections may be made based on known or derived annotations such as for example, species/organism, molecular size and weight, nonredundant base sequence, identified or predicted function, hydrophobicity, pKa, number of rotatable bonds, site of action, protein family or super-family classifications, etc. The set may even include all publicly known proteins, humans or otherwise.

Other sources include functional genomics studies or structure model prediction from known amino acid sequences or even directly from known DNA/RNA sequences. Potential reactants may also be identified as the result of various biochemical assays or other experiments, such as with use of protein chips, genetic or proteomic expression studies, comparative homology analysis at either the sequence or structural level, functional pathway or signal pathway studies, or other methods.

While referred to as a "target molecule" as an example, it should be understood that targets are not limited to single molecules, as described above and that what applies to target molecules applies to other types of targets, unless otherwise specified. The same is true for leads and other lead candidates referred to as lead molecules and potential reactants referred to as potential reactant molecules.

At this point, it is worthwhile to discuss in more detail the term 'environment' as it relates to embodiments of the invention. As already mentioned in the background, the term 'environment' generally refers to the physical and chemical surroundings of the site of reaction between molecules. In some embodiments of the invention, the environment might be in a human body, a nonhuman body, a laboratory environment, or other biologically relevant environment. In other embodiments, the environment might be specified as less than all of a body, such as a specific organ, the circulatory system, or the nervous system. Examples for the site of reaction include various intracellular domains, within cellular nuclei, out in the bloodstream, in the digestive tract, at various membranes, and at cellular surfaces.

Often, the environment of the target includes other components, such as other molecules, compounds of one or more molecules and/or other bioreactive agents or inert components. In some embodiments, the environment may include the plurality of atoms, ions, and/or molecules that comprise a solvent within which the site of reaction is embedded. Examples of solvent atoms, ions, or molecules may include water, alcohols, alkanes, salts, sugars, fatty acids, acids, bases, hydronium (H+) ions, free radicals, peptides or other biomolecules and even biopolymers that exist in at or near the site of reaction of the target or potential reactant and the lead. In other embodiments, the environment may also include continuum solvation models used to model various properties such as dielectric strength, ionizability, permeability, chemical potential, electrostatic potentials, etc. In yet other embodiments, an environment might be further characterized by more than just its chemical components, such as by an amount of light or other radiation available, temperature, pressure, water or other relevant environmental conditions.

Note for the purposes of the invention the environment of the site of reaction between the target and the lead may be very different from the environment of the site of reaction between a potential reactant and the lead. In fact, the site of reaction need not take place in the same cell type, tissue, or even organism. In some cases, the environment for the site of reaction for the target and lead is known and the lead can be confined to a certain portion of the organism by various means, for example injection into muscle tissue, etc. In which case the two environments, one for the target-lead site of reaction, the other for the potential reactant-lead site of reaction, may be the same or at least very similar. In such cases it may also be possible to exclude potential reactants that inhabit environments substantially different from that associated with the site of reaction for target and the lead. In most cases, however, the environment might not be highly specific, as the leads, targets, and/or potential reactants might migrate through the digestive tract, bloodstream and other areas of the organism.

As already discussed in the background section, the binding affinity may involve various enthalpic and entropic components. The enthalpic components may include contributions from both intramolecular and intermolecular interactions such as, but not limited to, electrostatics, vdW, desolvation, hydrogen bonding, metal-ligand interactions, and intramolecular strain. Entropic components, which are often harder to model accurately, may include, but are not limited to, the loss of conformation entropy upon binding and solvent related phenomena such as the hydrophobic effect. For a discussion of standard modeling of potential energy and entropic components of the free energy in the context of docking and scoring, the reader is referred to [6, 17, 26, 29, 31].

Both the enthalpic and entropic contributions to the free energy may be predicted or approximated via use of one or more computational methods as applied to a physical model. As an example of binding energy, the experimentally determined binding energy for the complex between methotrexate and dihydrofolate reductase is −55.34 KJ/mol implying a dissociation constant of $K_d=1.97e-10$ at standard physiological conditions (again refer to www-mitchell.ch.cam.ac.uk/pld/energy.php).

Examples of models include those based on quantum-mechanical calculations, classical molecular mechanics, statistical mechanics, and empirical and/or knowledge-based schemes, or any hybrids thereof. Examples of standard computational methods include molecular dynamics simulations, statistical mechanics simulations, functional optimization routines (such as Monte Carlo, genetic algorithms, dynamic programming, simulated annealing), free energy perturbation theory, QM/MM simulations, etc.

In the context of molecular mechanics models or molecular dynamics simulation, parameters, energy parameters are generally associated with constituent atoms, bonds, and/or chemical groups to represent a particular physical or chemical attribute in the context of the calculation of one or more standard energy components. Assignment of an energy parameter may depend solely on the chemical identity of one or more atom or bonds involved in a given interaction and/or on the location of the atom(s) or bond(s) within the context of a chemical group, a molecular substructure such as an amino acid in a polypeptide, a secondary structure such as an alpha helix or a beta sheet in a protein, or of the molecule as a whole. An example would be the value of charge assigned to a nitrogen atom involved in the peptide bond on the backbone of a lysine residue of a protein with regard to the electrostatic interaction. Another example would be the value of a charge assigned to a nitrogen atom in the side chain of an arginine residue of a protein, where the assigned value of charge may be substantially different than that associated with the aforementioned nitrogen in a lysine residue Typically, the parameters are assigned to atoms or groups of atoms or bonds of the target/lead/potential reactant, as well as other atoms or molecules in the environment, via use of an all-atom or a unified atom force field such as AMBER [40, 41], OPLS [42], MMFF [43], CHARMM [44], etc. Energy parameters may be assigned to one or more molecules prior to the time of computation and stored in some computer readable format (i.e., flat file, database tables, etc.) and then retrieved as needed or may in fact be assigned 'on the fly' during the actual computation itself.

For the purposes of the invention, chemical and structural information, relevant annotations, as well as associated energy parameters, for target, lead, and potential reactant molecules may be stored in molecule records. These molecule records may be digitally represented as a plurality of database records, as separate files, or in other data structures. In specific implementations, a record is read from a database, stored as an individual file and that individual file is passed to other parts of the invention for operation of the data contained in the file.

The records can represent their target/lead/potential reactant in a number of ways. In one embodiment, a record for a molecule includes a list of all of the atoms in the molecule, where they are located in space, energy parameters corresponding to various physical interactions, approximations for groups of atoms (such as for less relevant portions of the molecule, such as the interior portions of a protein far removed from the active site), as well as other data about the molecule, such as atom type, atom position and bonds. FIGS. 4A and 5A show sample records according to one embodiment detailing the relevant data storage for the target, lead, and potential reactant molecules as pertains to the invention.

For example, the target protein dihydrofolate reductase associated with pdb entry 4dfr is represented by a target molecule record 400 in FIG. 4A, as per one embodiment of the invention. In FIG. 4A, item 403 represents the one or more names associated with the protein, item 405 represents bioinformatics and proteomics annotations related to source information, function, and reactions/processes involving the protein. Item 407 represents the functional/structural classification and family information for the protein, and may also include links to homologs based on sequence and/or structural comparisons.

In FIG. 4B, item 410 represents the amino acid sequence of the protein with annotation for predicted secondary structural elements, where items 411, 412, and 413 respectively represent beta sheet strands, alpha helices, and various turns and/or hairpins. Item 414 represents structural annotation for the protein such as that founded in a valid pdb header regarding the experimental structural data, including citation, crystal resolution, and chain information.

Item 415 represents the block of data associated with the chemical identity and spatial coordinates of individual protein atoms or other hetero atoms (as defined with regard to the PDB standard [62]) such as salt ions, structural water oxygens, or other molecules associated with the protein structure, i.e., similar to ATOM or HETATM records in a pdb formatted file. For an example of the data stored in item 415 of the target molecule record according to some embodiments of the invention, the reader is referred back to the description associated with FIG. 1D. In other embodiments of the invention, some form of computational processing is used to detect missing or 'broken' residues and atoms and then repair the structure by placing the missing structural components at estimated locations. Examples of currently available software tools that can perform such repair functionality include SYBYL™ from Tripos, Chimera™ from UCSF, and WhatIf™.

Note that if the target record corresponds to a bound complex, then heteroatoms associated with the ligand may or may not be included. In one embodiment, the structural data of item 415 of FIG. 4B may include raw measured values. In another embodiment, data values are generated as the result of a standard energy regularization routine serving as a preprocessor to any further computational modeling. In yet another embodiment, the target molecule record may in fact contain both the raw and final processed structural data, as well as various intermediate states.

Item 423 represents a block of data, similar to a pdb or mol2 connect record, listing various chemical bonds, i.e., covalent bonds, disulfide bonds, and may even include intraprotein H-bonds or H-bonds to structural waters. For an example of the data stored in item 423 of the target molecule record according to some embodiments of the invention, the reader is referred back to the description associated with FIG. 1D.

In one embodiment, item 425 of FIG. 4C is a field containing nonbonded energy parameters associated with the protein atoms (column 426), including both full and partial charges (column 427), mass (column 428), vdw radius (column 429) and well depth parameters (column 430) as per a 12-6 Lennard Jones potential. t Typically, the final choice of nonbonded energy parameters depends on the interactions models for various energy components. For example, a model for solvation/hydrophobic effect may require atomic solvation parameters as per the fragmental solvation model of Stouten et al. [73]. As another example, H-bond parameters may be required in order to model interactions between H-bond donor and acceptor groups as per a 12-10 Lennard Jones potential.

In one embodiment, item 431 is a field containing bonded energy parameters associated with protein bonds or groups of adjacent protein bonds regarding the dihedral energy associated with changes in proper torsions. Here columns 432 represent various parameters (e.g., phase, amplitude, modality, etc.) used in conjunction with a torsional energy model based on a Pitzer potential. Typically, the final choice of bonded energy parameters depends on the interactions models for various energy components. For example, additional parameters may be required in order to represent bonded energy components related to bond stretching, bond angle bending, improper torsions, or even ring perturbations.

In one embodiment, both the nonbonded and bonded energy parameters depicted in items 425 and 431 of FIG. 4C, are assigned using the Amber96 force field [40, 41]. However, it should be understood that the chosen method of assignment of energy parameters, as well as the nature of the energy parameters themselves, associated with items 425 and 431 are merely examples as pertains to one embodiment of the invention. In another embodiment, the energy parameters are assigned 'on-the-fly' at the time of computation and items 425 and 431 are unnecessary.

Lastly, item 433 is an optional field that may include links to various known biomolecules (natural or otherwise) that bind to the target protein and any associated reaction data if available.

Lead records are also provided for each lead candidate biomolecule for use in regard to the invention. For example, the lead candidate biomolecule methotrexate is represented by a lead candidate molecule record in FIG. 5A, as per one embodiment of the invention. In FIG. 5A, item 434 represents the one or more names associated with the lead candidate, 435 represents various chemical annotations associated with the chemistry of the compound including the chemical formula, molecular weight, chemical name, and CAS registry number. Item 437 represents the chemical and/or structural classification of the biomolecule and may include any number of standard compound classifiers used in regard to biomolecules. Item 437 may further include links to other compound homologs based on chemical and structural comparisons.

Continuing in FIG. 5A, item 445 represents the block of data associated with the chemical identity and spatial coordinates of individual atoms as per a mol2 formatted file, usually after assignment of ionizations states and hydrogenation of the lead molecule. Item 453 represents a block of data, similar to a pdb or mol2 connect record, listing various chemical bonds, e.g., covalent bonds. For an example of the data stored in items 445 and 453 of the lead candidate molecule record according to some embodiments of the invention, the reader is referred back to the description associated with FIG. 2D. In FIG. 5B, items 455 and 457 represent separate blocks of data for nonbonded and bonded energy parameters in a manner similar to those assigned to the target molecule. For an example of the data stored in items 455 and 457 of the lead candidate molecule record according to some embodiments of the invention, the reader is referred back to the description associated with items 425 and 431 of FIG. 4C.

Item 459 is an optional field that may include links to various known target molecules for which the lead is known bind and associated reaction data if available. In the present example, pdb accession codes are listed for known complexes featuring methotrexate. Lastly, item 460 is another optional field representing an ADME/Tox profile for the lead candidate that may also include a list of known side effects as the result of prior preclinical or clinical testing.

In another embodiment, the structural data may have been generated using appropriate computational tools. In yet another embodiment the structural data may have been generated in silico as per inclusion in a virtual compound library. In another embodiment, the structural data may have been obtained from a combinatorial chemistry library. In still another embodiment, the structural data may be 2-D or 3-D in nature, though typically the 2-D info will be converted by an appropriate computational structure generation tool. An example of such a software tool is the program CORINA [74].

In one embodiment of the invention, a potential reactant record may have a form very similar to that of a target molecule record as described in regard to FIGS. 4A-4C. In another embodiment, the form of the potential reactant record may in fact even be identical in form to that of a target record, especially when the potential reactant may be a biopolymer. Typically, however, there may be less annotational information, less known binders and hence little or no reaction data available. Furthermore, in some cases the structural data may be as the result of structural model prediction as opposed to direct measurement. This is often the case when considering many membrane-associated proteins such as GPCRs or ion channel receptors. Model-built structures are also often used when considering large protein families of similar receptors.

In one embodiment of the invention, targets, lead candidates, and potential reactants are represented or modeled as complete molecules (or compounds of more than one molecule) when they interact in with one another and with their environment. In another embodiment, to speed up one or more computational processes, irrelevant or inactive portions of such molecules might be removed for the computational process and the targets, lead candidates and/or potential reactants modeled as partial molecules with fewer atoms and bonds than the actual molecules normally possess. For example, in one embodiment, all protein atoms excluding those residing in or near one or more binding pockets of a target protein might be ignored. In another embodiment, all hydrogen atoms except for polar hydrogens attached to potential hydrogen bond donors might be ignored. In yet another embodiment, the hydrogen atoms are united with their non-hydrogen atom counterpart instead of being ignored. In another embodiment, similar treatment of hydrogen atoms might hold for atoms in the lead candidate and/or potential reactants.

In one embodiment of the invention, atoms comprising residues in the interior of the protein and away from the surface are grouped together according to each distinct residue and both energy parameter assignment and subsequent computational modeling is sped up by treating each group as one unit for the purposes of computation. Done properly, both appropriate removal of portions of the molecule(s) and replacement of other portions by representative groups can reduce the number of calculations needed considerably without significantly affecting the result of the computation.

In one embodiment, delivery of the lead and/or the location of the site of reaction between the lead and a target or potential reactant would be taken into account. For example, where a lead is a drug that is to be orally ingested, the representation of the lead for the computational process might be the portion of the lead that remains after the lead passes through the digestive system. In another example, if the potential reactant is a membrane-bound protein and the site of reaction is at the cellular surface, the representation of the potential reactant may include only that portion of the protein residing outside the cell.

Herein the term "reaction" refers to some chemical or physical interaction that changes an action of one or more of the reactants. For example, consider a target that is a protein involved in some undesirable biological process causing a disease or illness. A remedy for the disease or illness might then involve some lead biomolecule, such as a small molecule ligand, that reacts with the culprit protein and thereby renders the protein inactive for that particular undesired effect.

Reactions are modifications to the reactants, the environment, or the interactions of reactants to their environment. Cross-reaction is a reaction between two or more reactants the lead candidate and a potential reactant, often another biopolymer different from the target, which is unanticipated and even possibly undesirable. An adverse cross-reaction is when a reactant binds with another reactant, causes a change in action or creates a response that leads to an adverse effect on the local environment, a section of tissue, an organ, or even the entire organism. An example of such an adverse cross-reaction is methotrexate binding with proteins in the liver, other than dihydrofolate reductase, and thereby inducing toxic side effects like hair loss, nausea, and liver damage as is common with chemotherapy treatments. As described above, an ADME/Tox profile attempts to assess reactions related to absorption, distribution, metabolism, excretion, and toxicity.

Reactivity is used herein as a term representing chemical activity between one or more molecules in conjunction with their environment. A reactivity value may be qualitative (reacts at all, highly reactive, not very reactive), quantitative (estimation of the binding free energy, enthalpy, reaction rate or velocity, dissociation or inhibition constant, experimentally derived signal intensity, results from high-throughput screening, QSAR prediction [53][54], etc.), observational (demonstrates a certain characteristic, induces an effect, an observed symptom, a syndrome), or empirical (knowledge or rule-based predictions, indications from similar molecular combinations) in nature. Cross-reactivity refers to the reactivity of a cross-reaction, potentially adverse or otherwise, as previously discussed.

Reaction measure is a function of one or more reactivity values. In one embodiment of the invention, the reaction measure depends on one reactivity value representing an estimation of the binding affinity. In another embodiment, the reaction measure depends on multiple reactivity values, for example one representing an estimation of the binding affinity and another representing the result of a QSAR analysis. In another embodiment, the reaction measure is a polynomial function of one or more reactivity values. In yet another embodiment, the reaction measure is a nonlinear function of one or more reactivity values, for example a Boltzmann probability distribution based on an estimation of the binding energy. A cross-reaction measure refers to a reaction measure as pertains to a cross-reaction, potentially adverse or otherwise, as previously discussed.

Reaction profile assigned to a combination featuring a lead candidate with a potential reactant is a function of the reaction measure and other variables. In some embodiments, a reaction profile may include various biological and/or chemical annotations. Such annotations may include, but are not limited to, classification based on Lipinski's "rule of five", source/functional/homolog annotation of the target/lead/potential reactant molecule, results of an ADME/Tox profile, location of the site of reaction, log P, etc. The reaction profile may be qualitative (e.g., a grade or a categorization) or quantitative (e.g., a composite score or a mathematical function). A cross-reaction profile refers to a reaction assessment as pertains to a cross-reaction, potentially adverse or otherwise, as previously discussed.

Source annotations may include knowledge of the host organism, organ, tissue, membrane, cell type, wild type of the target/lead/potential reactant molecule.

Functional annotations may include knowledge or prediction of function for the target/lead/potential reactant molecule, including, for example, knowledge of the function for a protein, the function of a gene which encodes a protein, or knowledge of a biological pathway or reaction cycle to which the biomolecule corresponds.

Homolog annotations may include information linkages to other biomolecules which are considered to be similar to the query target/lead/potential reactant, i.e., 'query molecule', in some manner. In one embodiment of the invention, when the query molecule is a protein, homolog linkages may be assigned based on sequence level homology between the amino acid sequence of the query molecule and a reference collection or database of amino acid sequences corresponding to known peptides or proteins. In another embodiment, homolog links may be assigned based on sequence level homology between nucleic acid sequences that encode the query molecule (if applicable) and a reference collection or database of nucleic acid sequences corresponding to known nucleic acid sequences corresponding to genes, mitochondrial genes, mRNA, tRNA, ribosomal RNA, etc. In yet another embodiment, the aforementioned amino acid and nucleic acid sequences that comprise the reference collection or database may come from a variety of different species and may correspond to biopolymers that may or may not be already characterized in terms of biological function.

In one embodiment, when the query molecule is a polypeptide or protein, homolog linkages may also be assigned based on structural homology to known public and proprietary proteins based on protein motifs, secondary structure elements, conserved regions, and, if available, protein tertiary structure. In another embodiment, if the query molecule is not a protein, for example a general organic compound, homolog linkages may also be assigned based on structural homology to known chemical structures using a variety of chemical and/or structural clustering and classification techniques [75, 76].

In another embodiment of the invention, homolog annotations, either within the same species or across different species, may be used to infer additional functional annotation for the query molecule based on family classification, phylogenetic trees, or other functional annotation of homologous reference molecules.

Risk assessment is a summary assessment for each lead candidate reflecting the probability of one or more potentially adverse cross-reactions and is based on the set of reaction profiles corresponding to reactions between each lead candidate and the set of potential reactant molecules. A high value for the risk assessment may imply that the lead candidate is not safe due to one or more toxic side effects, not desirable due to multiple unwanted side effects, or not efficacious due to high reactivity with various potential reactants of consequence, whether in the same environment as the desired site of action for one or more target molecules or at some other biological stage of the drug delivery/distribution process, such as in the digestive tract.

Evaluation of the risk assessment for a lead candidate may also involve reaction data pertaining to the lead candidate in reaction with one or more desired target molecules. Dependent on the magnitude of the risk assessment it may be desirable to modify the lead candidate in order to increase binding specificity to one or more desired targets. In one embodiment if the risk assessment is too high, the lead candidate may be discarded entirely. The more potential reactant molecules for which reaction profiles with the given lead candidate are available, the more likely the risk assessment is to be accurate and robust. The risk assessment may also be updated when new potential reactant molecules become available.

Referring to FIG. 6, a computer-aided modeling system 500 is shown that evaluates cross-reactions between one or more leads and a collection of potential reactants, generates corresponding reaction profiles, develops a risk assessment for each lead candidate, and if desired enters a drug redesign and optimization procedure in order to improve the selectivity of certain leads.

In FIG. 6, item 502 represents a potential reactant molecule database or library. In one embodiment, information associated with each potential reactant molecule is stored in a molecule record of the form illustrated in FIGS. 4A-4C and the records are passed to other parts of system 500 during processing. In FIG. 6, the potential reactant molecule records are denoted as 506. Note that various forthcoming embodiments in regard to the potential reactant database 502 and the associated potential reactant molecule records 506 apply equally well to lead database 504 and the associated lead molecule records 508.

While referred to herein as a "potential reactant molecule", it should be understood that in some embodiments the potential reactants are not limited to single molecules. The potential reactant database may be a collection of flat files stored on a file system, a relational database, or other type of information database as commonly used in commercial and/or academic settings.

In one embodiment, database 502 may represent all known nonredundant proteins in the Protein Data Bank with periodic updates in order to keep the information current. In another embodiment, database 502 may include protein model-built structures based on amino acid sequences representing various translations of genomic information in GenBank, SwissProt, etc. In another embodiment, some structures stored in database 502 may represent relevant subsets of various biopolymers such as those including conserved regions, binding sites, individual chains, etc.

In another embodiment, the selection of potential reactant molecules comprising database 502 is influenced by prior knowledge or characterization of one or more target molecules and the local environments of the anticipated site of reaction involving possible lead candidate molecules. In one embodiment, potential reactant molecules may represent proteins or other polypeptides that are homologous to all, or portions of, one or more desired molecules, at the level of secondary or tertiary structure or amino acid sequence. In one embodiment, potential reactant molecules may represent biomolecules that are known to be involved in biological pathways featuring one or more desired target molecules or instead in biological pathways relevant to fundamental biological processes as relates to distribution, excretion, metabolism, and absorption of a drug candidate for one or more desired target molecules. There are many ways in which potential reactant molecules may be selected in order to form database 502, though often this will involve one or more considerations regarding desired target molecule(s) and their attendant biological pathways. In another embodiment, the potential reactant database 502 also contains molecule records for one or more target molecules of interest for the various lead candidates to be tested for cross-reactions. As already mentioned in regard to FIGS. 4A-4C and 5A-C, the molecule records for potential reactants and those for target biomolecules may be very similar in nature.

In FIG. 6, item 504 represents a lead candidate molecule database or library. In one embodiment, information associated with each lead candidate molecule is stored in a molecule record of the form illustrated in FIGS. 5A-5C and the records are passed to other parts of system 500 during processing. In FIG. 6, the lead candidate molecule records are denoted as 508. The lead candidate database may be a collection of flat files stored on a file system, a relational database, or other type of information database as commonly used in commercial and/or academic settings.

The lead candidate molecules that comprise database 504 may be selected in many ways. In one embodiment, the lead candidate molecules are the result of various lead generation and/or other lead optimization processes as applied to one or more desired target biomolecules. As discussed previously, such lead generation and optimization processes may include rational drug design, QSAR, structure based design, in silico compound or virtual library screening, high throughput screening including functional assays, microfluidics, other cell based or biochemical assays, etc. or any combination thereof. Those lead candidates that successfully pass through such processes may then be incorporated as members of database 504. In yet another embodiment, the lead candidate molecules may represent a set of leads that would otherwise enter preclinical testing.

In another embodiment, lead candidate molecules incorporated in database 504 may be selected as a subset from an existing compound library, virtual or otherwise, based on structural and chemical diversity and any prior characterization for one or more desired target biomolecules. In another embodiment, a collection of lead candidate molecules may be used as seed structures, i.e., cores or scaffolds, to which standard computational tools for molecular structure generation and/or combinatorial chemistry techniques are applied in order to generate a collection of additional compounds with diverse and representative structure based on the original core structures. One skilled in the art should recognize that there are many ways in which prospective lead candidate molecules may be selected in order to form database 504, and often this will involve one or more considerations regarding the target biomolecule(s) of interest and their attendant biological pathways. In fact, in many cases, the lead candidate molecules in database 504 are expected to inhibit or catalyze or affect in some other manner the behavior of one or more desired target molecules.

In one embodiment, database 504 may also include molecule records for structures generated as the result of a drug redesign and optimization procedure, as will be discussed more in detail later.

In another embodiment, the molecule records and relevant data stored in databases 502 and 504 may be compressed using a variety of information compression schemes in order to reduce the cost of storage of the potentially millions and millions of numerical parameters associated with the atoms and bonds of the molecules. In another embodiment, when the relevant data is being accessed from the database, the data can be uncompressed on-the-fly at the time of the database transaction or request.

The molecule records in databases 502 and 504 may also be clustered by a variety of chemical, structural, and other bioinformatics techniques in order to make database subselections and queries both easier to process and easier to understand and review. In one embodiment, database 502 is clustered ahead of time and cluster representatives are selected for processing by further processing steps of modeling system 500 in order to speed up the total computing time. The results generated for the lead candidates against the set of cluster representatives of the potential reactants are then reviewed and for those cluster representatives for which significant reactivity was demonstrated, the entire corresponding cluster is retrieved from database 502 and more processing via modeling system 500 initiated in order to complete the risk assessments for the lead candidate(s) in question. In this manner, a great number of leads can be screened against a great number of potential reactants and then individual processing can be done between one or more leads and the individual members of a promising cluster. Such an embodiment may allow for more efficient coverage of the set of possible lead candidates and potential reactants for a given amount of effort.

Referring again to FIG. 6, processing block 520 represents a reaction determiner.

One or more potential reactant records 506 are provided to reaction determiner 520 along with one or more possible lead candidate records 508. Alternatively, reaction determiner 520 could proactively retrieve additional molecule records directly from databases 502 and 504 as required during processing as the situation warrants. Reaction determiner 520 determines a set of reaction measures for one or more lead candidate records 508 and one or more potential reactant records 506.

Each reaction measure corresponds to a pair of records, where one record corresponds to a lead candidate and another to a potential reactant. The reaction determiner may process each pair in a sequential manner or may process multiple pairings in parallel. In a typical embodiment, one lead candidate record and multiple potential reactant molecules are presented to the reaction determiner and the reaction determiner generates reaction measures for each pair consisting of the lead candidate molecule vs. one potential reactant molecule. In another embodiment, the one potential reactant record and multiple lead candidate records are presented to the reaction determiner 520, which subsequently generates reaction measures for each pair consisting of a lead candidate molecule vs. the one potential reactant molecule.

In order to construct a reaction measure, the reaction determiner 520 may directly generate one or more reactivity values based on additional input parametric data retrieved from storage 522 on a computer recordable medium or may retrieve one or more already calculated reactivity values from storage 524 on a computer recordable medium. In one embodiment the reaction determiner computes an estimation for the binding free energy between lead candidate and potential reactant record(s) according to a molecular mechanics method that utilizes various force field parametric data located in storage 522, such as for example parameters associated with the AMBER96 force field. In another embodiment, reaction determiner 520 retrieves reactivity values computed either beforehand or in parallel by another processing module that may not even be directly part of modeling system 500. For example, QSAR calculations for the lead candidate and potential reactant molecule(s) may be computed off-line and then appropriately stored on a computer recordable medium such as a file system or a computer memory and then retrieved by the reaction determiner when forming the relevant reaction measure. In yet another embodiment, dedicated processing elements for QSAR calculations are embedded within reaction determiner 520.

Reaction determiner 520 outputs data representing the reaction measure of one or more lead candidate vs. potential reactant pairs to the potential reactant-lead candidate reaction filter 530. The reaction filter 530 applies various decision criteria based on input reaction measures to determine whether or not a particular potential reactant—lead candidate pair should be made available to later stages of the modeling system 500. In principle, many of the lead candidate—potential reactant pairs may demonstrate little or no reactivity and thus the corresponding reaction measures will be very low. Therefore, in some cases it may be desirable to filter out those pairs for which it appears that there is low probability of reaction, i.e., poor binding affinity.

In one embodiment the reaction filter 530 allows only those lead candidate potential reactant pairs to pass through to later stages of the system 500 that possess reaction measures with magnitude greater than a predefined threshold. In another embodiment, the reaction filter 530 waits until all relevant pairs have been processed by the reaction determiner 520, ranks them by their corresponding reaction measures, and then passes through top X %, where X is a selected number between 1 and 100. In yet another embodiment, reaction filter 530 applies a predefined thresholding function that takes one or more reaction measures as input function arguments and then applies a thresholding logic to the transformed reaction measures, e.g., polynomial function or exponential function of the reaction measure(s).

In another embodiment, in order to better judge the reaction measure for a particular lead candidate—potential reactant pair, the reaction filter 530 employs relevant precompiled reaction data for the same lead candidate in reaction with one or more desired target molecules for which the lead candidate is expected to react and/or bind. For example, if the relevant reaction data is available, the reaction filter 530 may filter out lead candidate reactant pairs where the reaction measure is less than a constant multiplied by the reaction measure for the lead candidate and a desired target molecule, where said constant is usually between zero and one. In yet another embodiment, the reaction filter 530 instead employs relevant precompiled reaction data for the potential reactant in reaction with one or more biomolecules that are known to bind with the potential reactant, i.e., known binders or complexes involving the potential reactant. However, in many cases, such additional reaction data may not be available and thus is not necessarily required by the reaction filter 530.

In other embodiments, even those lead candidate—potential reactant pairs that are not allowed to pass through the reaction filter 530 still have their corresponding reaction measures and other data transmitted to for storage on a computer recordable medium in one or more database tables or flat files (items 532). In another embodiment, all lead candidate potential reactant pairs are allowed to pass through the reaction filter and the reaction filter 530 merely serves as a mechanism to capture relevant reaction data and dump the results for storage in data structures 532.

In some embodiments, the reaction filter may be deemed to be not essential to the invention and all lead candidate—potential reactant pairs pass through to later stages of the modeling system 500.

Reaction filter 530 outputs reaction data corresponding to passing lead candidate potential reactant pairs to the reaction profiler 550. The reaction profiler 550 is responsible for constructing a reaction profile, as previously defined, for each lead candidate—potential reactant pair based on the corresponding input reaction measures from 530 and other variables. As described earlier, these other variables may, for example, include classification based on Lipinski's "rule of five", source/functional/homolog annotation of the relevant target/lead/potential reactant molecule(s), results of an ADME/Tox profile, location of the site of reaction, log P, log D, etc. As described previously in regard to FIGS. 4A-4C and 5A-5C, lead candidate and potential reactant records may contain various data related to source, functional, and structural annotations, as well as various pharmacokinetic properties.

The potential reactant molecule may also contain homolog links to other biomolecules for the previously described purposes of homolog annotations. In one embodiment, the homolog links refer to other potential reactant molecules stored as records in the potential reactant molecule database 502. In another embodiment, potential reactant molecule records are buffered in dedicated data structures or files as represented by storage buffer 552 in FIG. 5. In another embodiment, buffer 552 is loaded from databases or data structures on computer recordable medium not directly associated with the potential reactant database 502.

In yet another embodiment, a different storage buffer 554 represents data structures or files for the storage of one or more target biomolecules to which the lead candidate(s) are known to bind. In such embodiments, the data stored in buffer 554 may be used to generate reaction measures for molecular combinations featuring the target(s) and the lead candidate. The resultant reaction measures may then be compared with reaction measures associated with the lead and one or more potential reactants, e.g., relative comparison of binding affinity. In one embodiment, the comparison(s) may involve the use of one or more quantitative lead-target reaction measures to generate numerical thresholds for additional filtering or weighting of quantitative reaction measures for the same lead and potential reactants. In another embodiment, storage buffer 554 also contains records for biomolecules homologous to the identified target molecules. In one embodiment, these target records and/or homologous target records may be stored and directly accessible from the potential reactant database 502 with a suitable cross-reference in the lead candidate database 504. In one embodiment, buffer 554 is loaded from various input databases or data structures not directly associated with databases 502 or 504.

Information such as that stored in buffer 554, while typically useful, is not essential to the invention and in cases where such pre-identified target molecules do not exist then buffer 554 is vestigial in nature. In another embodiment of the invention, neither buffers 552 nor 554 are used by the reaction profiler 550 in constructing the reaction profile corresponding to a particular lead candidate—potential reactant pair.

The reaction profile may be qualitative in nature, e.g., a grade, or quantitative in nature, e.g., a score or a function value. Remember that the reaction profiler 550 will generate reaction profiles for only those lead candidate—potential reactant pairs that are submitted from the reaction filter 530. In general, the more reaction data available, including reaction measure(s), annotations for both the lead candidate and the potential reactant, and other properties such as an ADME/Tox profile or the results of various biochemical assays, when forming the reaction profile for a lead candidate—potential reactant pair, the higher the likelihood that the reaction profile is of higher quality, i.e., relevant and meaningful.

Generally, the reaction measure reflects the strength of the cross-reaction between the lead candidate and the potential reactant, but by itself infers little about whether the cross-reaction is adverse or not, i.e., toxic or induces unwanted side effects. Nor by itself does the reaction measure directly predict whether a lead candidate will have enough bioavailability at the intended site of reaction with one or more desired target biomolecules in order to be efficacious in treatment of the intended medical condition or disease.

In one embodiment, a confidence value or score is assigned to a reaction profile based on both the magnitude of the reaction measure and annotational data corresponding to the lead candidate and the potential reactant, including source, functional and homolog annotation. If for example, the potential reactant has a known source and function, such as say the human insulin molecule and the reaction measure is high, the confidence score for the reaction profile will be high, thereby reflecting that there is a high probability that the reaction is both strong and likely adverse. In another example, the potential reactant may be a protein of known function in the brain for which it is likely that any cross-reaction would be malignant, but annotational information attached to the lead candidate shows that the lead cannot penetrate the blood brain barrier and thus it is unlikely the lead and potential reactant will ever encounter one another.

In another example, the potential reactant is not itself well characterized yet it shows high structural and sequence level homology to a mouse protein related to a known oncogene in mouse. As described previously, homology annotation may be used to infer function. Therefore, if the lead candidate were to exhibit a high reaction measure for the aforementioned mouse-homolog potential reactant, one could deduce that there is a high likelihood that the lead may be carcinogenic even in a human host organism. On the other hand, even though the potential reactant is potentially hazardous to react with, the reaction measure may be so low that the confidence score is relatively low since it may be dubious that there is any sort of reaction with the lead.

In yet another example, if the potential reactant were classified as a member of a protein family involved with the humane immune system, a high reaction measure would infer that there is a high likelihood of a potentially adverse immune system response to the lead, possibly inducing an allergic reaction. In yet another example, a high confidence score may reflect loss of bioavailability due to strong interaction with a potential reactant that is characterized via various annotations and classifications as a biomolecule involved in various digestive processes. In yet another example, a high confidence score may reflect lack of efficacy because the potential reactant is an enzyme that inhabits the same localized environment of the intended site of reaction with a desired target and the potential reactant binds very strongly to the lead thereby competing with the target and effectively reducing the effect of the lead candidate.

In another embodiment, the confidence score is replaced by a grade or other qualitative classification that reflects both the magnitude of the reaction measure(s) and the known available information about the potential reactant and the lead candidate molecule. In yet another embodiment, an ADME/Tox profile, when known or extrapolated based on structural or functional similarity with another molecule, for the lead candidate regarding various metabolic, absorption, distributional, excretive, and toxic properties of the lead may be used to supplement the construction of the reaction profile. For example, knowledge about the likelihood of the lead to survive the organism's digestive system intact, to be absorbed efficiently into the blood stream, permeability through key membranes such as the blood brain barrier, carcinogenicity, etc. may be used to infer whether the reaction with a particular potential reactant is likely to occur or to be harmful.

The reaction profiler 550 outputs reaction profiles for each lead candidate—potential reactant pair to the risk assessment analyzer 560. Based on the input reaction profiles, it is the responsibility of the risk assessment analyzer 560 to form a consensus or summary assessment for each lead candidate after analyzing the set of reaction profiles involving the lead candidate molecule. In some embodiments, the risk assessment for each lead candidate is a quantitative score or ranking based on the set of reaction profiles. In one embodiment of the invention, a set of quantitative reaction profiles involving the lead candidate are summed in order to generate a risk assessment. In another embodiment, the risk assessment is a linear combination of the reaction profiles. In yet another embodiment, the risk assessment is a function of the quantitative reaction profiles, such as a polynomial function or a nonlinear function.

In yet another embodiment the risk assessment represent the output prediction of a computer learning approach, such as a neural network or support vector machine, where the quantitative reaction profiles serve as the inputs and the learning algorithm is trained on a data set of compounds with known characterizations in terms of side effects and efficacy, including both favorable and unfavorable leads. In another embodiment, the risk assessment is determined as the average of the top N reaction profiles, ranked based on their corresponding confidence measure, where N for example is a small positive integer. In another embodiment, the risk assessment is a consensus grade or other qualitative categorization made based on qualitative reaction profiles. In another embodiment, the risk assessment is a confidence score or probability generated based on use of statistical analysis as applied to multiple reaction profiles, wherein the statistical analysis includes, but is not limited to, multivariate (e.g., z-score, chi-squared, etc.) or Bayesian (e.g., Bayesian risk) analysis.

As with other components of the system, the risk assessment analyzer 560 may update the risk assessment for a given lead candidate as more potential reactants and/or more reaction data becomes available. In one embodiment, the risk assessment analyzer 560 may output the risk assessment for each lead candidate to dedicated data structures for storage on a computer recordable medium and future review and analysis.

To better illustrate this discussion let us once again consider the lead candidate methotrexate shown in FIGS. 2A-2D and also represented in the molecule records depicted in FIGS. 5A-5C. Methotrexate inhibits the target molecule dihydrofolate reductase (DHFR) depicted in FIGS. 1A-1D. Methotrexate is in fact a cancer therapeutic used in chemotherapy for the treatment of various carcinomas including certain leukemias. Using modeling system 500 to generate a risk assessment for the compound methotrexate, one may observe several results.

In the first result, it may be observed that methotrexate binds fairly strongly to a potential reactant representing thymidylate synthase sourced from E. Coli. E Coli thymidylate synthase (ECTS) is a protein involved in the limiting irreversible step in the synthesis of de novo DNA as relates to the conversion of deoxyuridine 5'-monophosphate to deoxythymidine 5'-monophosphate in E. Coli bacteria. FIGS. 7A-7C shows a representation of a molecular complex between E Coli thymidylate synthase and methotrexate in a format similar to that depicted in FIGS. 3A-3C but now with the structural data obtained from PDB entry 1axw. Though the reaction measure associated with ECTS may be weaker than that associated with DHFR it is still likely to be significant. When constructing the reaction profile for the ECTS methotrexate pair, examination of the annotation information attached to ECTS shows that the E. Coli variant of TS is highly homologous to the human variant. Yet, further examination of the functional annotation associated with ECTS suggests that when treating cancers this may actually be a beneficial target to likewise inhibit, as it might also further restrict tumor cell growth by additional down-regulation of new DNA synthesis, which is key to tumor growth.

In the second result, it may be observed that methotrexate binds with some affinity to a second potential reactant representing rabbit cytosolic serine hydroxymethyl transferase (or SHMT) an enzyme involved in catalysis of multiple reactions including the production of methionine, the reversible production of serine, and of glycine among others. High sequence homology to the human mitochondrial gene encoding SHMT in humans suggests that methotrexate may affect those reaction pathways involving SHMT. Though high concentrations or dosages of methotrexate may adversely affect certain amino acid synthesis pathways in cells, examination of an associated methotrexate ADME/Tox profile shows that methotrexate is highly unlikely to penetrate external cellular membranes and thus interaction with cell surface receptors is unlikely to significantly disrupt the various mitochondrial processes involving SHMT in amino acid synthesis and purine production. Thus, the obtained reaction profile for the rabbit SHMT-methotrexate pair would not by itself indicate a high probability of adverse cross-reactions in humans. FIGS. 8A-8C shows a representation of a molecular complex between rabbit cytosolic serine hydroxymethyl transferase and folinic acid (a close chemical homolog to methotrexate) in a format similar to that depicted in FIGS. 3A-3C, with the structural data obtained from PDB entry 1k12.

In the third result, it may be observed that methotrexate binds to one or more potential reactants representing certain proteins or enzymes in the kidneys of humans or other organisms such as mouse, rabbit, or dog with moderate reaction strength. Based on source/functional/homolog annotations and an ADME/Tox profile suggesting potential concerns regarding excretion, the reaction profile may now reflect a likely probability of adverse kidney function when the dosage of methotrexate is high.

Thus, for example, the summary risk assessment for methotrexate many include the following predictions: (a) unlikely to disrupt biological pathways featuring SHMT, (b) likely to further restrict tumor cell growth by virtue of reaction with thymidylate synthase, and (c) potential kidney problems and/or damage related to high concentrations of methotrexate; all of which may be represented, as discussed previously with regard to various embodiments, in the form of a quantitative score or ranking thereby codifying the risk assessment of methotrexate.

In the embodiment portrayed in FIG. 6, the risk assessment analyzer 560 also outputs the risk assessment for each lead candidate to the drug redesign filter 570.

The drug redesign filter 570 examines the input risk assessments to determine whether the lead candidate can and should be modified in order to increase selectivity to one or more desired target biomolecules yet also reduce the likelihood or strength of identified potential cross-reactions as indicated by the risk assessment for the lead candidate.

In one embodiment of the invention, the decision process used by the drug redesign filter 570 is dependent on various user input parameters. In one embodiment, these user input parameters may be quantitative in nature, such as for an example an allowed number of potential cross-reactions with a reaction measure above a predefined numerical threshold. In another embodiment, these user input parameters may be qualitative in nature, such as for example a tolerance associated with a qualitative risk assessment.

In another embodiment, these user input parameters whether qualitative or quantitative in nature may be used to ignore low-risk lead candidates and letting all other leads pass through the filter 570. In yet another embodiment, high-risk candidates are also ignored since the user may deem such leads unlikely to be modified in such a way that all potentially hazardous or undesired side effects are avoided. In another embodiment, the filter 570 allows only a user-specified number of leads pass through after sorting the leads based on their risk assessments according to user-specified order.

The drug redesign filter 570 may also include knowledge of reaction data of the lead candidate in reaction with one or more desired target molecules. For example, if the lead candidate is known to react comparatively weakly with the desired target and yet exhibits many potential adverse cross-reactions, the lead candidate may be considered to not be worth the effort of an drug redesign process and thus blocked by filter 570.

Typically, the intent of the drug redesign filter 570 is to identify those lead candidates that may benefit from possible chemical and structural modification in order to increase selectivity of the lead with the desired target biomolecule(s), i.e., degrade reactivity with potential reactants not affiliated with the target(s) but maintain high reactivity with the desired target molecule(s) themselves. This may potentially also include further improvement of reactivity with the desired target. In another embodiment, the filter 570 may also identify those lead candidates that may benefit from possible chemical and structural modification in order to increase reactivity to a beneficial potential reactant while maintaining high reactivity with the desired target molecule(s). For example, in the case of methotrexate it may be both possible and desirable to modify the lead in order to better bind to human thymidylate synthase while preserving methotrexate's high reactivity with its original target human dihydrofolate reductase, thereby creating a modified lead candidate with even better cancer therapeutic properties. In such cases, the potential reactant in question may be reclassified as a potential target. The drug redesign filter selects a subset of lead candidates and transmits them to the drug redesign and optimization engine 580 for possible chemical and structural modification, while the remainder of the lead candidates are sent to dedicated data storage 575 for future review and analysis.

In FIG. 6, the drug redesign and optimization engine 580 represents a processing unit that explores possible redesign modifications of one or more lead candidates as submitted by the drug redesign filter 570. These modifications are typically chemical and structural changes to the lead candidate that will alter its reactivity with one or more biomolecules. For example, these modifications may be intended to reduce or degrade the reactivity of a lead with one or more potential reactants that have been identified in the risk assessment of the lead as generated in the risk assessment analyzer 560, while at the same time maintaining a satisfactory degree of reactivity with one or more desired target molecules, i.e., increase specificity of the lead candidate. In another embodiment, the intent is to introduce chemical and structural modifications to increase reactivity with one or more potentially beneficial cross reactants. In yet another embodiment, the modifications are intended to increase binding affinity of the lead with desired target molecule(s) in order to improve efficacy and/or reduce dosage requirements, while at the same time maintain a low risk of adverse cross reactions.

For the purposes of the following discussion, the term structural component is defined to be a chemical group, or even in some cases an individual atom. Valid structural components may include for example, acetyl groups, methyl groups, carboxyl groups, amine groups, hydroxyls, aromatic and heterocyclic rings, various phosphorous and sulfur-containing groups, etc. Other valid structural components include one or more nucleic acids such as in DNA and RNA, or one or more amino acids, including modified amino acids as the result of chemical modification and/or cleavage, or carbohydrates, fatty acids, or even protein secondary structure components such as a beta sheet or an alpha helix. Other valid structural components may include individual atoms such as those commonly found in organic compounds such as carbon, oxygen, nitrogen, sulfur, phosphorus, and hydrogen, or halogens such as chlorine, bromine, fluorine, or transition metals or other metal ions such as iron, magnesium, etc.

Possible modifications of the lead candidate structure include addition of new structural components, substitution and/or deletion of structural components comprising the existing lead candidate structure, or any combination thereof. The addition of new structural components or modification of existing structural components can dramatically alter the reactivity of the lead candidate.

For example, the removal of key hydrogen bond donor or acceptor groups may destabilize a reaction with a potential reactant. On the other hand, the addition of specific hydrogen bond donor or acceptor groups may increase binding affinity to one or more target molecules. The addition of other groups may introduce steric clashes or repulsions that significantly degrade reactivity with one or more molecules by disrupting the preferred binding mode and reducing otherwise energetically favorable Van der Waals and electrostatic interactions.

Changes in structural components can also change the ionization state or the charge distribution of the lead thereby greatly affecting its interaction with an electrostatic potential field, such as that generated by charges and dipole moments of target molecule(s) and potential reactant(s). Introduction or removal of hydrophobic and/or hydrophilic groups may alter the various solvation properties of the lead, as well as interactions between the lead and its solvent environment, e.g., aqueous solution. Changes in structural components may change the nature of the most energetically favorable conformations of the lead whether isolated in a solvent environment or in close proximity to target molecules or potential reactants. The addition, substitution, and/or deletion of structural components may also affect the electron density of the ligand, thereby affecting the quantum mechanical interactions of the lead with one or more target molecule(s) or potential reactants. In most embodiments, each resultant molecular structure obtained through various modifications of the original lead should be legitimate in the sense of proper valences and/or correct ionization states, and in most cases should be chemically synthesizable.

FIG. 9A displays a 2-D representation of the structure of methotrexate in picture 800. Picture 820 on the other hand, shows a scaffold molecular structure for methotrexate and its structural siblings, highlighted with seven different linkage sites at which various structural components may be added, substituted, or even deleted. In FIG. 9, the linkage sites are indicated respectively as 802, 803, 804, 806, 807, 808, and 809. At the five linkage sites (802, 803, 804, 806, and 807), the symbol 'R' denotes any of a number of possible structural components. The sixth linkage site is represented by the shaded region 808. Here linkage site 808 represents possible substitution or deletion of the molecule beyond the amide bond labeled 810. The seventh and final linkage site is represented by an even larger shaded region 809. Here linkage site 809 represents possible substitution or deletion of the molecule beyond the bond labeled 811.

In FIG. 9B, table 830 lists a set of example molecular groups or fragments that may serve as alternative structural components. Table 830 may also be further augmented by individual atomic species and or even amino acids, such as the twenty residues commonly found in proteins.

FIGS. 10A-10B depict six example structures (items 840, 850, 860, 870, 880, and 890) obtained by adding or substituting alternative structural components from table 830 at one or more linkage sites shown in picture 820 of FIG. 9A relative to the final structure of methotrexate in picture 800. For example, structure 840 is the result of substitution of the methyl group in methotrexate at linkage site 804 by an individual hydrogen atom. In fact, structure 840 is another known binder of dihydrofolate reductase, named aminopterin. However, such a small structural modification is not likely to reduce the risk of possible adverse cross-reactions.

Structure 850 is the result of replacement of the carboxyl group at linkage sites 806 and 807 by methyl groups. Structure 860 shows the replacement of the trigonal planar amine group at 802 by an $sp^2$ oxygen resulting in the compound commonly known as folate. Structure 870 shows the wholesale replacement of all structural components beyond the amino group at linkage site 808 with a serine residue, one of the twenty standard amino acids, and a further substitution of the methyl group at 804 by a hydrogen atom as in the case of aminopterin. Example structure 880 shows the replacement of all structural components beyond the linkage site 809 with an ester group and a further substitution of the trigonal planar amine group at 803 by an $sp^2$ oxygen as with folate. Structure 880 is more commonly known as biopterin. Lastly, structure 890 shows the substitution of an ester group at linkage site 808 and the further replacement of the methyl group at 804 with a pteridine ring.

At this point, it is worthwhile to discuss the combinatorial aspects of such a procedure. For N different alternative structural components and M linkage sites, there are $M^N$ possible structures, not counting deletions. For example, if N=25 and M=3, then there are $25^3$ or 15,625 possible structures. Alternatively, if N=15 and M=6, then there are 11,390,625 possible structures. Now often not every one of the alternative structural components can be placed at a given linkage site. Moreover, many of the possible combinations may reflect poor choices for drugs in terms of ADME/Tox profiles or may in fact mean that the compound cannot be chemically synthesized. In addition, it may not be necessary, nor is it often expedient to, directly explore every possible combination and the above numerical examples are provided for the purposes of illustration. In some embodiments, only a subset of the possible linkage sites are modifiable at a given time, e.g., three out of six possible linkage sites, which for N=15 implies only 67,500 different structures.

Depending on the desired effect, the drug redesign optimization engine 580 needs to efficiently explore a number of structural combinations and select one or more of the best new structures that usually maintain high reactivity with one or more desired target molecules and at the same time alters (usually degrades) the reactivity of the lead with one or more potential reactants.

In one embodiment, the drug redesign optimization engine 580 employs a computational method wherein binding cavities of the target and cross-reactant are compared to identify parts that are dissimilar. A fast rough evaluation may then be done by creating representative shape functions for each cavity and then computing mutual overlap of said shape functions. Regions of low overlap are deemed dissimilar. Picking regions of the binding cavity of the potential reactant that are dissimilar, one can identify potential linkage sites in or near the dissimilar loci for possible alterations of the existing lead candidate structure. One can then add or modify one or more chemical groups on the lead molecule at the identified linkage sites, such that it creates repulsion or steric clashes or lower the incidence and/or strength of hydrogen bonding, etc. in one or more of the selected dissimilar regions. Done correctly, and because the selected loci are dissimilar between the potential reactant and the target molecule, the reaction strength of the lead and potential reactant can be reduced while preserving reactivity with desired target molecule(s). The identified regions may also take electrostatic characteristics of the molecules into account when computing similarity measures between various portions of interest. In another embodiment, one or more dissimilar regions of the binding cavity of the target molecule(s) can be selected and appropriate modifications made to those structural components of the lead in close contact with the aforementioned dissimilar regions so as to increase the reactivity of the lead with the target(s) while minimally altering the binding interaction of the lead with one or more potential reactants. Such a modified lead may then be able to treat the given target medical condition, but at lower dosages and thereby avoid adverse side effects.

In another embodiment, the leads from the lead candidate database 504 that are being tested can be treated as a mini-lead library themselves, wherein parts of different leads can be exchanged based on allowable chemical rules to create new ones. In other words, the alternative structural components to be tested at various linkage sites on the lead in question may come (in part) from one or more other tested leads. If one lead does not cross-react or reacts with lower affinity to a certain potential reactant, one can use or exchange parts of that lead with the current one to create a modified lead. In particular, if one can preserve parts of the lead that bind well to the target, but replace certain other parts with parts from another lead (that does not react with the cross reactant in question), one may be able to increase specificity in binding to the target molecule(s).

Regardless of how the new perturbated structures are generated from the primary scaffold or core of the original lead candidate structure, the new structures must be assessed in terms of their reactions to the potential reactants referenced in the redesign process as well as the desired target molecule(s). In one embodiment, new structures may be assessed based on the results obtained from one or more biochemical or wet lab assays. In another embodiment of the invention, this assessment is achieved via computational means based on prediction of the preferred binding mode and binding affinity for each new structure and the relevant potential reactant(s) and target molecule(s).

In one embodiment, the computational predictions are obtained using one of a number of conventional techniques already discussed earlier in both the background section and the detailed technical description, including standard shape complementarity methods, conventional techniques based on molecular mechanics paradigms, molecular dynamics and/or quantum mechanics simulations, QSAR, free energy perturbation theory, or even the utilization of various empirically derived or knowledge-based scoring function.

In one embodiment, electrostatic interactions are modeled via a modified Coulombic potential with distance-dependent dielectric. In another embodiment, electrostatic interactions and electrostatic desolvation effects involving the molecules and the local environment are computed using a numerical solver to the Poisson-Boltzmann equation. In another embodiment, both electrostatic desolvation effects and hydrophobic interactions are modeled using a fragmental volume based model. In another embodiment, electrostatic desolvation effects are modeled using a modified Born solvation model. In another embodiment, Van der Waals interactions are modeled via modified Lennard-Jones potentials. In another embodiment, both hydrogen bond and metal-ligand interactions are modeled via modified Lennard-Jones or modified Morse potentials.

In another embodiment, standard molecular mechanics expressions are used to model conformational changes due to bond stretching, bond bending, and both proper and improper torsions, as well as various ring transformation. In yet another embodiment, empirical formulations are used to assess lipophilic and hydrophilic interactions. In another embodiment, empirical formulations are used to model the loss of entropy of the lead and/or protein side chains upon binding. In another embodiment, various basis function sets are used to solve for eigenstates and eigenvalues of a suitable Hamiltonian in a quantum-mechanical approach. In yet another embodiment, certain approximations may be made in order to simplify the Hamiltonian and thereby speed up a solution to the quantum mechanical wave function representing the electron density of the molecules.

In one embodiment of the invention, energy parameters necessary to complete the aforementioned calculations, and as described earlier, are provided as part of a molecular force field such as for example that of AMBER [40, 41], OPLS [42], or the Merck Molecular Mechanics force field [43]. In another embodiment, the energy parameters may be annealed over time or iterations as per an annealing molecular dynamics simulation or other optimization procedure, including, but not limited to, a genetic algorithm, a memetic algorithm, simulated annealing algorithm, etc. As already described, some or all of these energy parameters may be stored within the molecule records for both the lead candidates and the potential reactants in databases 502 and 504.

In another embodiment, the method and apparatus of Prakash I is used to evaluate each new structure in an accurate and efficient manner.

In one embodiment, the newly generated structures from the drug redesign and optimization engine 580 are resubmitted to the lead database 504 and processed again by system 500 for modeling of potential cross-reactions. In some embodiments, the process of modeling cross-reactions, followed by drug redesign and optimization and the generation of new structural variations of the lead may be iteratively repeated until some terminating condition or other criteria is satisfied. This is shown in FIG. 6 by the arrow connecting item 580 and item 504.

In FIG. 10A the possible modified structure 850 to methotrexate removes both carboxyl groups at linkage sites 806 and 807 of the picture 820 of FIG. 9A and replaces them with hydrophobic methyl groups that cannot form hydrogen bonds. Since the two carboxyl groups do not form strong hydrogen bonds to certain surface residues of dihydrofolate reductase, but instead most likely bond with solvent water molecules, their deletion may slightly destabilize methotrexate binding to the desired target dihydrofolate reductase. However, since the new methyl groups are somewhat sterically similar to the removed carboxyl groups the changes should not overly destabilize methotrexate binding to the desired target dihydrofolate reductase. On the other hand, their removal and replacement by hydrophobic groups may greatly destabilize binding to a potential reactant, say, for example, in the human kidneys, and thereby reduce undesired changes in various excretive processes as discussed in regard to the risk assessment analyzer 560.

Molecule records for those new structures that exhibit the desired changes in reactivity with respect to one or more potential reactants and to one or more target biomolecules (e.g., reduction of reactivity to potential adverse cross-reactants, maintenance or increase of high reactivity to desired target(s), etc.) may then be transmitted back for storage in the lead candidate database 504 and annotated appropriately as new redesigned or optimized structures. The new optimized candidate structures can then be resubmitted for a new round of processing by modeling system 500 to ensure that the probability of adverse cross-reactions with potential reactants in database 502 is sufficiently low and thereby improve the likelihood that the new structure(s) are better drug candidates. Using these techniques, a desirable lead might be found that is not in the initial lead candidate database.

One should recognize that this process of screening vs. potential reactants, generating risk assessments for each lead, performing a drug redesign and optimization, and rescreening can be performed multiple times until enough desirable lead candidate structures with high specificity, low toxicity, and other beneficial properties are obtained.

Modeling system 500 may be implemented in software, hardware, firmware or some combination thereof. System 500 may be a local system or a distributed system, may operate on one or more general-purpose computers, and might include various data communication channels such as network connections as needed to convey data around the system.

In one embodiment, modeling system 500 may be implemented on a dedicated microprocessor, ASIC, or FPGA. In another embodiment, modeling system 500 may be implemented on an electronic or system board featuring multiple microprocessors, ASICs, or FPGAs. In yet another embodiment, modeling system 500 may be implemented on or across multiple boards housed in one or more electronic devices. In yet another embodiment, modeling system 500 may be implemented across multiple devices containing one or more microprocessors, ASICs, or FPGAs on one or more electronic boards and the devices connected across a network. The use of dedicated hardware processing units may be intended to speed up various calculation steps such as those associated with the reaction determiner 520 and/or the drug redesign optimization engine 580 and may involve a system similar to that described in Prakash I.

In some embodiments, modeling system 500 may also include one or more storage media devices for the storage of various, required data elements used in or produced by the analysis.

Alternatively, in some other embodiments, some or all of the storage media devices may be externally located but networked or otherwise connected to the modeling system 500. Examples of external storage media devices may include one or more database servers or file systems. In some embodiments involving implementations featuring one or more boards, the modeling system 500 may also include one or more software processing components in order to assist the computational process. Alternatively, in some other embodiments, some or all of the software processing components may be externally located but networked or otherwise connected to the modeling system 500.

As described previously in regard to the reaction determiner 520, the system 500 may operate on one lead candidate and potential cross reactant at a time, i.e., in sequence, or on multiple pairs in parallel. In a typical embodiment, one lead candidate record and multiple potential reactant molecules are presented to the system 500, a risk assessment for the lead candidate is established based on the relevant set of reaction profiles for each lead candidate and potential reactant pair, and then a new lead candidate record and the same set of multiple potential reactant molecules are presented to the system 500 and the process repeated until risk assessments for all relevant lead candidates are created.

Optionally, the drug redesign optimization process of 580 may be initiated after completion of a risk assessment for one lead candidate molecule or after processing is completed for all relevant lead candidate molecules. In another embodiment, results are generated for a set of lead candidates against a set of potential reactant molecules, but as new potential reactant molecules become available, instead of recomputing lead candidates against all potential reactants only those potential reactants involved in recent database updates or even only those potential reactants that are nonhomologous to existing structures in the potential reactant database are presented to system 500 in order to update the reaction profiles and risk assessments for the lead candidates. As already discussed, the entire procedure can be performed multiple times in an iterative procedure as new candidate structures are constructed in the drug redesign and optimization engine 580.

In some embodiments, instead of individually computing reaction measures for each lead and individual potential reactant, the potential reactants may be clustered or grouped according to accepted methods based on various sequence homology, structural or chemical similarity, and/or functional bioinformatics or proteomics classification criteria and representatives from each cluster or group can be used to generate reaction measures against a specific lead. Then only those potential reactant clusters that demonstrate probable reactivity can be individually processed member by member in order to generate detailed individual reaction measures and subsequent reaction profiles with respect to the lead, thereby reducing overall computational cost and time.

Modeling system 500 may also be used to identify possible alternative targets for the lead candidate since some potential cross-reactions may not be adverse but may instead be serendipitous and result in unanticipated benefits.

In summary, a novel system for computational prediction of potentially adverse cross-reactions and selection and optimization of leads and variations thereof has been described. Lead candidates might be selected from a plurality of lead candidate molecules for being known to react with one or more desired target molecules. The target might be a protein in a disease pathway and the lead molecule a potential drug candidate for addressing the disease. The lead molecule might be a component of a small molecule drug, or a component of a protein-based drug. One or more reactivity values for the lead molecule with each of a set of potential reactant molecules are determined and a reaction measure calculated. The potential reactant molecules might be selected from a plurality of reactant molecules present in either human or other organism, from various organs/tissues/cell types, in either the same as or different environment than that associated with the anticipated site of reaction of the lead and the target molecule(s). The reaction measure might be a function of the change in free energy of the system comprised of the molecules and their environment, as a result of a reaction, i.e., the binding affinity between lead and the potential reactant (or target) molecule.

The reaction measure, in conjunction with other reaction data such as source/functional/and homolog annotations for the lead candidate and the potential reactant, as well as other measures such as a corresponding ADME/Tox profile and computed reaction measure(s) for the lead candidate and the desired target molecule(s), are used to establish a reaction profile for the lead candidate—potential reactant pair. A reaction profile for a lead-candidate potential reactant pairing may also involve one or more additional criteria including occurrence and/or biological function of the reactant molecules in a specified cell type, in a specified tissue, in a specified organ, and/or in a specified organism, effects of various delivery, distribution, absorption, excretion, and metabolic mechanisms involving the lead molecule, relevant functional pathway information regarding the potential reactant and target molecule(s), and relevant sequence-based, motif, and/or structural homologs of the reactant molecules.

The set of reaction profiles for each lead candidate for the set of potential reactant molecules are collated and processed further in order to form a risk assessment for each lead. Dependent on the risk assessment of a lead, as well as various user input and other decision criteria, it may be worthwhile for the lead candidate to be chemically and structurally modified in order to increase binding specificity to the desired target(s) and reduce the likelihood of adverse cross-reactions and/or reduce required dosage amounts when used in treatment. For such purposes, the system also provides for the coordinated and efficient redesign or optimization of selected lead candidate structures utilizing addition, substitution, and/or deletion of various non-core molecular groups at one or more linkage sites on the molecule until a one or more structures are obtained that demonstrate desired reactive behavior in terms of the predicted binding mode and binding affinity between the lead and one or more potential reactant and target molecule(s). As discussed, various embodiments encompass both novel and conventional techniques for evaluation of the new potential structures generated in such a redesign process.

The above description is illustrative and not restrictive. Many variations of the invention will become apparent to those of skill in the art upon review of this disclosure. The scope of the invention should, therefore, be determined not with reference to the above description, but instead should be determined with reference to the appended claims along with their full scope of equivalents.

What is claimed is:

1. A method for predicting and modeling potential cross-reactions between a lead candidate biomolecule, known to react with one or more desired target biomolecules, and a plurality of potential reactant biomolecules, the method comprising:

providing a data representation of the lead candidate biomolecule to a computational modeling system, wherein the data representation comprises chemical and structural information of the lead candidate biomolecule;

providing a data representation of each of the potential reactant biomolecules to the computational modeling system, wherein the data representation comprises chemical and structural information of the potential reactant biomolecules;

obtaining, with the computational modeling system, one or more reactivity values for each potential cross-reaction between the lead candidate biomolecule and a respective potential reactant biomolecule in the context of an environment;

constructing, with the computational modeling system, a plurality of reaction measures, each as a function of the reactivity values associated with a respective potential cross-reaction; and constructing, with the computational modeling system, one or more reaction profiles, each profile including a single confidence value that is a function of a respective reaction measure and that is a function of one or more bioinformatics and/or chemical annotations associated with the potential reactant biomolecule corresponding to that reaction measure;

based on at least two of the reaction profiles, evaluating a risk assessment reflecting a likelihood of one or more adverse reactions involving the lead candidate biomolecule; and outputting the risk assessment to a computer recordable medium, wherein the computational sytem for modeling potential cross-reactions comprises one or more of a computer including software to implement the computational platform dedicated hardware, firmware, or a combination thereof.

2. The method of claim 1, wherein the environment is the physical and chemical surroundings of the site of reaction between the lead candidate and the potential reactant.

3. The method of claim 1, wherein the environment is the physical and chemical surroundings of the site of reaction between the lead candidate and a target biomolecule for the lead.

4. The method of claim 1, wherein the environment includes a representation (implicit or explicit) of a solvent medium comprising a plurality of atoms, ions, and/or other molecules and within which the site of reaction is embedded.

5. The method of claim 1, wherein the environment includes one or more components of a human or other mammalian body.

6. The method of claim 1, wherein the potential reactant biomolecule includes a biopolymer or one or more parts of a biopolymer, including one or more active sites.

7. The method of claim 1, wherein the lead candidate includes a synthetic compound, a chemical group, a peptide, a medicinal compound, a protein-based drug, or a carbohydrate.

8. The method of claim 1, wherein one of the reactivity values used in forming a reaction measure associated with the potential cross-reaction is a computational estimation of the binding affinity or free energy of the reaction.

9. The method of claim 1, where some or all of the reactivity values associated with the potential cross-reaction are pre-generated or derived off-line, stored on a computer readable medium in a digital representation, and then retrieved at the time of formation of the reaction measure.

10. The method of claim 9 wherein at least one of the reactivity values used in forming a reaction measure associated with the potential cross-reaction is the result of prior prediction of quantitative structure activity relationships between the two biomolecules.

11. The method of claim 9 wherein at least one of the reactivity values used in forming a reaction measure associated with the potential cross-reaction is a measurement or result obtained from one or more laboratory assays.

12. The method of claim 11 wherein the laboratory assay(s) include screening or other functional assays, whether in vitro, cell-based, or in vivo.

13. The method of claim 1, wherein a reaction measure associated with the potential cross-reaction is a linear combination of multiple reactivity values.

14. The method of claim 1, wherein a reaction measure associated with the potential cross-reaction is a nonlinear function of multiple reactivity values.

15. The method of claim 1, wherein a reaction measure associated with the potential cross-reaction is a score or grade based on one or more reactivity values.

16. The method of claim 1, further comprising:
prior to constructing the reaction profile, removing, with a reaction filter, from further consideration those potential cross-reactions for which the associated reaction measure fails to meet a decision criteria.

17. The method of claim 16 wherein the decision criteria is a numerical threshold applied to the magnitude of the input reaction measure(s).

18. The method of claim 16 wherein the decision criteria is applied dynamically as reaction measures are generated by the system.

19. The method of claim 16 wherein the decision criteria is applied after all reaction measures featuring a particular lead candidate biomolecule have been generated.

20. The method of claim 16 wherein the decision criteria is based on relative comparison to corresponding computed or experimentally obtained reaction measures for the lead candidate biomolecule in reaction with one or more targets.

21. The method of claim 20 wherein the decision criteria is the application of an affinity threshold to the binding affinity (or equivalent reaction measure) associated with a reaction between the lead candidate biomolecule and a potential reactant, wherein the affinity threshold is formulated as a predefined constant multiplied by the computed or measured binding affinity (or equivalent reaction measure) associated with a reaction between the lead candidate biomolecule and a chosen target.

22. The method of claim 6, wherein the bioinformatics and other chemical annotations associated with the potential reactant biopolymer that are used in the construction of the reaction profile include data related to source, functional, homology, and/or family or other classification information associated with the potential reactant.

23. The method of claim 22 wherein the source annotations for the potential reactant include information related to the organism, species, organ, tissue, cell type, mutant or wild type, and/or strain, from which the potential reactant is obtained, expected to originate, or where it is likely to be found.

24. The method of claim 22 wherein the functional annotations for the potential reactant include information related to the biological, or disease, pathways or other reactions and processes involving the potential reactant or a biological function for the potential reactant.

25. The method of claim 22 wherein the homology information for the potential reactant includes links to structure-based and/or sequence-based homologs to other biopolymers of the same or different organisms, wherein the structure-based homology for proteins is established based on similarity of conserved regions, protein motifs, or tertiary structure and the sequence-based homology for biopolymers is based on similarity of the primary amino acid or underlying genomics sequences.

26. The method of claim 25 wherein the homology information for the potential reactant includes structure-based and/or sequence-based homology to one or more targets that react or bind with the lead candidate biomolecule.

27. The method of claim 1, wherein the risk assessment is also based on one or more bioinformatics and/or chemical annotations associated with the lead candidate, and wherein the annotations associated with the lead candidate include data related to chemical and structural composition, reaction chemistry, homology, and/or chemical or structural classification information associated with the lead candidate.

28. The method of claim 27 wherein the chemical and structural composition annotations for the lead candidate include information related to the chemical formula, chemical name, index descriptors related to one or more chemical catalogs, chemical and physical properties of the biomolecule, knowledge of chiral centers and stereochemistry, or structural information in 2-D or 3-D representations.

29. The method of claim 27 wherein the reaction chemistry annotations for the lead candidate include reaction data related to one or more chemical reactions or biological processes that involve the lead candidate.

30. The method of claim 29 wherein the scope of the chemical reactions or biological processes is extended to include those chemical reactions or biological processes that involve other biomolecules of high structural and/or chemical similarity to the lead candidate.

31. The method of claim 29 wherein the reaction data related to one or more chemical reactions or biological processes involving the lead includes links to information for one or more targets to which the lead binds or reacts.

32. The method of claim 29 wherein the reaction data related to one or more chemical reactions or biological processes involving the lead includes one or more information components of an ADME/Tox or other pharmacokinetic profile.

33. The method of claim 29 wherein the reaction data related to one or more chemical reactions or biological processes involving the lead includes one or more measurements obtained from one or more laboratory assays.

34. The method of claim 27 wherein the homology information for the lead candidate includes links to structure-based and/or chemical homologs to other biomolecules, wherein the structure-based and chemical homologies are established based on use of 2-D or 3-D pharmacophore models, various molecular descriptors used in compound clustering and classification, or similarity in quantitative structure activity relationships.

35. The method of claim 16 wherein information regarding the structural or chemical similarity of the potential reactant to one or more targets associated with the lead candidate is considered when applying the reaction filter to or constructing the reaction profile for a potential cross-reaction featuring the potential reactant.

36. The method of claim 16 wherein information regarding the structural or chemical similarity of the lead candidate to one or more binders for the potential reactant is considered when applying the reaction filter to or constructing the reaction profile for a potential cross-reaction featuring the lead.

37. The method of claim 1, wherein the risk assessment for a lead candidate biomolecule is updated, regularly or otherwise, as new potential reactants are identified and made available to the modeling system.

38. The method of claim 1, wherein the risk assessment is a linear combination or other functional composition of multiple quantitative reaction profiles.

39. The method of claim 1, wherein the risk assessment is a qualitative categorization or grade generated based on multiple quantitative reaction profiles.

40. The method of claim 1, wherein the risk assessment is a confidence score or probability or statistical quantity generated based on statistical analysis of multiple quantitative reaction profiles.

41. The method of claim 40 wherein the statistical analysis used in composing the risk assessment for a lead candidate biomolecule utilizes the mean or the median of all of or the top selected range of percentiles of a set of reaction profiles.

42. The method of claim 40 wherein the statistical analysis used in composing the risk assessment for a lead candidate biomolecule is a Bayesian risk analysis.

43. The method of claim 1, wherein the risk assessment represents the output prediction of a computer learning approach.

44. The method of claim 43 wherein the computer learning approach used to generate the risk assessment is based on a neural network.

45. The method of claim 43 wherein the computer learning approach used to generate the risk assessment is based on a support vector machine.

46. The method of claim 1, wherein the selection of a plurality of potential reactant biomolecules is made from the entirety, or a portion of, a 2-D or 3-D structural database.

47. The method of claim 1, wherein the selection of a plurality of potential reactant biomolecules involves prior knowledge of relevant biological and/or pharmacokinetic pathways.

48. The method of claim 1, wherein the potential reactants are biopolymers, and further comprising:
prior to providing a data representation of each of the potential reactant biopolymers, selecting the potential reactant biopolymers based on structural and/or sequence similarity to one or more targets of the lead candidate.

49. The method of claim 48 wherein the selection of a plurality of potential reactant biopolymers include other members of the protein or gene families, or other functional or bioinformatical classifications, of one or more targets of the lead candidate.

50. The method of claim 1, further comprising:
applying a clustering operation to the plurality of potential reactant biomolecules in order to generate a collection of clusters or groups based on a set of clustering criteria that includes consideration of chemical and/or structural similarity between potential reactants;
selecting one potential reactant from each cluster or group to be a cluster representative;
generating a set of reaction measures corresponding to potential cross-reactions between the lead candidate and each cluster representative;
applying a reaction filter to the obtained set of reaction measures to select a subset of cluster representatives that demonstrate high reactivity with the lead;
reselecting each cluster of potential reactants containing a passing cluster representative; and
generating a detailed individual reaction measure, and subsequent reaction profile, for each and every member of the reselected clusters.

51. The method of claim 50 wherein the potential reactants are biopolymers and the clustering criteria involves sequence homology, structural homology, and/or other bioinformatics or proteomics classification criteria.

52. The method of claim 1, wherein a further method for optimization and redesign of the lead candidate is employed in order to improve binding specificity to one or more desired targets and reduce reactivity to one or more potential reactants that are predicted or likely to be involved in a potentially adverse cross-reaction with the lead candidate, the method comprising:
identification of a molecular core or scaffold associated with the lead candidate that is required by the lead in order to bind to one or more desired targets;
identification of molecular groups or other components that may be added or substituted to one or more linkage sites on the scaffold;
analysis of reaction(s) between the lead and one or more desired targets, for which it is desired for the lead to react strongly, in terms of preserving or promoting energetically favorable molecular interactions between chemical groups associated with the lead and with each desired target;
analysis of reaction(s) between the lead and one or more potential reactants, for which it is not desired for the lead to react strongly, in terms of reducing energetically favorable, and/or promoting energetically unfavorable, molecular interactions between chemical groups associated with the lead and with each potential reactant;
selection of one or more linkage sites on the scaffold for addition to or substitution of the local molecular structure in accordance with the analysis of molecular interactions between the lead and one or more desired targets and also in accordance with the analysis of molecular interactions between the lead and one or more potential reactants;

selection of one or more molecular groups or other components to be added to or substituted for the local molecular structure at one or more of the selected linkage sites in accordance with the analysis of molecular interactions between the lead and one or more desired targets and also in accordance with the analysis of molecular interactions between the lead and one or more potential reactants;

construction of a plurality of structural variations of the lead candidate based on combinations of selected linkage sites of the scaffold with the addition or substitution of selected molecular groups; and evaluation of each new structural variant of the lead according to its reactivity to one or more potential reactants and with one or more desired targets.

53. The method of claim 52 wherein the evaluation of each new structural variant of the lead involves resubmission of the newly generated structural variants of the lead candidate as new input lead candidates to a system for modeling potential cross-reactions.

54. The method of claim 52 wherein lead candidates are prioritized for possible redesign and optimization based on evaluation of already constructed reaction profiles and/or an associated risk assessment for the lead candidate.

55. The method of claim 54 wherein a lead candidate is submitted for possible redesign and optimization when the corresponding risk assessment for the lead implies that the risk associated with potential adverse cross-reactions featuring the lead candidate with one or more potential reactants is within a tolerance and does not exceed a predefined limit.

56. The method of claim 52 wherein a plurality of structurally distinct scaffolds are identified for the lead candidate and are used as possible seeds for the generation of a plurality of structural variations of the lead during the possible redesign and optimization of the lead.

57. The method of claim 52 wherein the set of molecular groups identified for possible addition or subtraction to one or more linkage sites on the scaffold, include various chemical groups found in organic chemistry, amino acid side chains, residues, or even individual atoms or ions.

58. The method of claim 52 wherein the analysis of reaction(s) between the lead and one or more potential reactants involves identification of one or more intermolecular hydrogen bonds that if destabilized by alteration of interacting hydrogen bond donor or acceptor groups may reduce reactivity between the lead and the potential reactant yet do not overly compromise the reactivity of the lead with respect to one or more desired targets.

59. The method of claim 52 wherein the analysis of reaction(s) between the lead and one or more potential reactants involves identification of one or more intermolecular hydrophobic contacts that if destabilized by alteration of interacting hydrophobic groups may reduce reactivity between the lead and the potential reactant yet do not overly compromise the reactivity of the lead with respect to one or more desired targets.

60. The method of claim 52 wherein the analysis of reaction(s) between the lead and one or more potential reactants involves identification of one or more intermolecular salt bridges that if destabilized by alteration of interacting electrostatic or ionized groups may reduce reactivity between the lead and the potential reactant yet do not overly compromise the reactivity of the lead with respect to one or more desired targets.

61. The method of claim 52 wherein the analysis of reaction(s) between the lead and one or more potential reactants involves identification of one or more interacting chemical groups on either molecule that demonstrate high local steric complementarity that if chemically or structurally altered may reduce reactivity between the lead and the potential reactant yet do not overly compromise the reactivity of the lead with respect to one or more desired targets.

62. The method of claim 52 wherein the construction of a plurality of structural variations of the lead candidate further involves alteration of stereochemistry associated with one or more groups or components of the lead candidate.

63. The method of claim 52 wherein the construction of a plurality of structural variations of the lead candidate further involves alteration of the ionization state associated with one or more groups or components of the lead candidate.

64. The method of claim 53, wherein the process involving the construction of a plurality of structural variants of the lead candidate, their resubmission as inputs to a system for modeling potential cross-reactions based on the method of claim 1, and the subsequent construction of reaction profiles and/or a risk assessment for each new input structural variant versus one or more potential reactants is iteratively repeated until some terminating condition or other criteria has been met.

65. The method of claim 1, further comprising identifying one or more new potential targets from among the potential reactant molecules based on evaluations of reactivity and analysis of relevant biological and chemical annotations.

66. The method of claim 1, wherein at least one reaction profile includes a confidence value or score that is based on:
   a likelihood of a cross-reaction between the lead candidate and the potential reactant biomolecule provided by the corresponding reaction measure; and
   a likelihood of the cross-reaction being adverse based on the bioinformatics and/or chemical annotations associated with the corresponding potential reactant biomolecule.

67. The method of claim 66 wherein the confidence value or score is further based on a likelihood of the lead candidate encountering the corresponding potential reactant biomolecule in the target organism.

68. The method of claim 1, wherein the likelihood is expressed as a numerical value.

69. A storage media device containing instructions to direct a processor to perform a method for predicting and modeling potential cross-reactions between a lead candidate biomolecule, known to react with one or more desired target biomolecules, and a plurality of potential reactant biomolecules, the method comprising:
   providing a data representation of the lead candidate biomolecule to a computational modeling system, wherein the data representation comprises chemical and structural information of the lead candidate biomolecule;
   providing a data representation of each of the potential reactant biomolecules to the computational modeling system, wherein the data representation comprises chemical and structural information of the potential reactant biomolecules;
   obtaining one or more reactivity values for each potential cross-reaction between the lead candidate biomolecule and a respective potential reactant biomolecule in the context of an environment;
   constructing a plurality of reaction measures, each as a function of the reactivity values associated with a respective potential cross-reaction; and
   constructing one or more reaction profiles, each profile including a single confidence value that is a function of a respective reaction measure and that is a function of one or more bioinformatics and/or chemical annotations associated with the potential reactant biomolecule corresponding to that reaction measure;

based on at least two of the reaction profiles, evaluating a risk assessment reflecting a likelihood of one or more adverse reactions involving the lead candidate biomolecule; and;

outputting the risk assessment to a computer recordable medium.

70. The method of claim 1, further comprising querying a database to obtain the one or more bioinformatics and/or chemical annotations associated with the potential reactant biomolecule corresponding to that reaction measure.

71. The method of claim 1, wherein the single value of a reaction profile is a numerical score, and wherein a reaction measure is increased or decreased based on the annotations to obtain the numerical score.

72. The method of claim 1, further comprising:

providing a result of the risk assessment to a user for review.

73. The method of claim 1, wherein the risk assessment includes a quantitative value that is a function of respective confidence values of the at least two of the reaction profiles.

74. The method of claim 1, wherein the single value of a reaction profile is a qualitative classification.

75. The method of claim 1, further comprising:

based on the risk assessment, identifying the lead candidate biomolecule as not being a viable drug candidate.

* * * * *